(12) United States Patent
Klessig et al.

(10) Patent No.: US 7,169,966 B2
(45) Date of Patent: Jan. 30, 2007

(54) SALICYLIC ACID-BINDING PROTEIN ENCODING NUCLEIC ACID, SABP2, AND METHODS OF USE THEREOF

(75) Inventors: Daniel F. Klessig, Ithaca, NY (US); Dhirendra Kumar, Ithaca, NY (US)

(73) Assignee: Boyce Thompson Institute for Plant Research, Inc., Ithaca, NY (US)

( * ) Notice: Subject to any disclaimer, the term of this patent is extended or adjusted under 35 U.S.C. 154(b) by 30 days.

(21) Appl. No.: 10/780,002

(22) Filed: Feb. 17, 2004

(65) Prior Publication Data
US 2005/0034196 A1    Feb. 10, 2005

Related U.S. Application Data

(63) Continuation-in-part of application No. PCT/US02/26312, filed on Aug. 16, 2002.

(60) Provisional application No. 60/312,863, filed on Aug. 16, 2001.

(51) Int. Cl.
*C12N 15/82* (2006.01)
*C12N 15/29* (2006.01)
*A01H 5/00* (2006.01)

(52) U.S. Cl. .................. 800/279; 800/278; 800/298; 435/320.1; 435/468; 435/419; 536/23.6

(58) Field of Classification Search ............... 800/278, 800/279, 298; 435/320.1, 468; 536/23.2, 536/23.6
See application file for complete search history.

(56) References Cited

U.S. PATENT DOCUMENTS 5,977,442 A * 11/1999 Klessig et al. .............. 800/301

OTHER PUBLICATIONS

Baudouin, E. et al. "Functional expression of a tobacco gene related to the serine hydrolase family—Esterase activity towards short-chain dinitrophenyl acylesters"; Eur. J. biochem., 248: 700-706 (1997).

Dogru, E. et al. "The gene encoding polyneuridine aldehyde esterase of monoterpenoid indole alkaloid biosynthesis in plants is an ortholog of the α/β hydrolase super family"; Eur. J. Biochem., 267: 1397-1406 (2000).

Du, H. et al. "Identification of a Soluble, High-Affinity Salicylic Acid-Binding Protein in Tobacco"; Plant Physiol., 113: 1319-1327 (1997).

Falk, A. et al. "EDS1, an essential component of *R* gene-mediated disease resistance in *Arabidopsis* has homology to eukaryotic lipases"; Proc. natl. Acad. Sci. USA, 96: 3292-3297 (1999).

Hasslacher, M. et al. "Molecular Cloning of the Full-length cDNA of (*S*)-Hydroxynitrile Lyase from *Hevea brasiliensis*"; The Journal of Biological Chemistry, 271(10): 5884-5891 (1996).

Jirage, D. et al. "*Arabidopsis thaliana PAD4* encodes a lipase-like gene that is important for salicylic acid signaling"; PNAS, 96(23): 13583-13588 (1999).

Wäspi, U. et al. "The defense-related rice gene *PIR7b* encodes an α/β hydrolase fold protein exhibiting esterase activity towards naphthol AS-esters"; Eur. J. Biochem., 254: 32-37 (1998).

* cited by examiner

*Primary Examiner*—Medina A. Ibrahim
(74) *Attorney, Agent, or Firm*—Kathleen D. Rigaut; Robert C. Netter, Jr.; Dann Dorfman Herrell & Skillman, P.C.

(57) ABSTRACT

Novel nucleic acid molecules encoding SA-binding proteins involved in SA-mediated disease resistance responses are disclosed. Methods of use of the nucleic acid molecules and proteins of the invention are also provided.

20 Claims, 10 Drawing Sheets

Figure 4

```
  1       acgcgggaagaaagaaactaacaaggcataaattcaa ATG AAG GAA GGA AAA CAC TTT GTT TTA GTA CAT GGT GCA TGC  83
  1                                             M   K   E   G   K   H   F   V   L   V   H   G   A   C   14

84       CAT GGA GGT TGG TAC AAG CTA AAG CCA CTG CTA GAA GCT GCA AAG GTT ACA GCC CTT GAT TTA 158
 15        H   G   G   W   Y   K   L   K   P   L   L   E   A   A   K   V   T   A   L   D   L   39
                                                                          peptide #1 (pk22a, pk23 & pk55*)
159       GCA GCT TCT GGC ACT GAT TTG AGA AAA ATA GAG CTT CGC ACA CTT TAT GAT TAT ACT TTG CCA TTG ATG GAG 233
 40        A   A   S   G   T   D   L   R   K   I   E   L   R   T   L   Y   D   Y   T   L   P   L   M   E   64
           peptide #1 (pk22a, pk23 & pk55*)
234       TTG ATG GAA TCT CTT TCA GCA GAT GAG AAG GTT ATA TTA GCT GTT TTC ATG CCT GAT GGT ATG AAT TTG GGA CTT 308
 65        L   M   E   S   L   S   A   D   E   K   V   I   L   A   V   F   M   P   D   G   M   N   L   G   L   89

309       GCT ATG GAA AAG TAT CCA CAA CAA AAG ATC TAT AAT CAG TTT GCT GTT TTC ATG CCT GAT TCT GTT CAC AAC 383
 90        A   M   E   K   Y   P   Q   Q   K   I   Y   N   Q   F   A   V   F   L   A   F   M   P   D   S   V   H   N  114

384       TCC TCC TTT GTT TTG GAA CAG TAT AAT GAG CGG CCA GCC GAG AAT TGG TTG GAT ACT CAG TTT TTA CCA TAT 458
115        S   S   F   V   L   E   Q   Y   N   E   R   T   P   A   E   N   W   L   D   T   Q   F   L   P   Y  139
                                                           peptide #2 (pk32, 34 & 36)
459       GGT TCC CCT GAA GAG CCA CTG ACA TCC ATG TTT TTT GGC GCT CAC AAG CTC TAC CAG CTA TGC 533
140        G   S   P   E   E   P   L   T   S   M   F   F   G   A   H   K   L   Y   Q   L   C  164
                       peptide #3 (pk29)
534       TCT CCT GAG GAT CTT GCA TTA GCA TCA TCA TTG AGA CCA AGA GTT TAC ATT GTG GAC CTA TCG AAG GCC 608
165        S   P   E   D   L   A   L   A   S   S   L   R   P   R   V   Y   I   V   D   L   S   K   A  189
                                                                                      peptide #4 (pk22b)
609       AAG TAT TTC ACA GAT GAA CGG TTT GGA TCA GTG AAG AGA GTT TAC ACT GAG GAT AAA GGC ATA CCA 683
190        K   Y   F   T   D   E   R   F   G   S   V   K   R   V   Y   T   E   D   K   G   I   P  214
           peptide #5 (pk30 & pkx)
684       GAA GAA TTC CAG CGA TGG CAA ATT GAC AAC ATT GGT GTC ACT GAA GCA ATA GAG ATT AAA GGT GCT GAT CAC ATG 758
215        E   E   F   Q   R   W   Q   I   D   N   I   G   V   T   E   A   I   E   I   K   G   A   D   H   M  239

759       GCA ATG CTA TGC GAG CCC CAA AAA CTT TGC GCC TCT CTC CTC TTG GAA ATT GCC CAT AAA TAC AAC TGA tctctacatt 834
240        A   M   L   C   E   P   Q   K   L   C   A   S   L   L   L   E   I   A   H   K   Y   N   *  261

837       atgtcttcgtccatgtcaagatttcagtgtcatgctgctgtaatttttctatttttcgaccggcgcataactgtctttgcctattttaaggattgcagt 933

937       aatttcactcctctagtgtggaaggcttccacataaggattgttctgttctgtcctccattcaagtgtgtgtgttatgttgagatacttaaaccgtatcaattct 1032

1037      tgtaatgaacttctcttcctttttgaaaaaaaaaaaaaaa 1079
```

```
SABP2-N.tabacum  MKEGK----HFVLVHGACHGGWSWYKLKPLLEAAGHKVTALDLAASGTD-LRKIEELRTL  55
A.thaliana       MSEEKR-KQHFVLVHGSCHGAWCWYKVKPLLEAVGHRVTAVDLAASGIDTTRSITDIPTC  59
M.esculenta      MAVVD-----FVLIHTICHGAWIWYKLKPVLEAAGHKVTALDLAASGVD-PRQIEQINSF  54
H.brasiliensis   MAFAH-----FVLIHTICHGAWIWHKLKPLLEALGHKVTALDLAASGVD-PRQIEEIGSF  54
PIR7B            MEISSSSKKHFILVHGLCHGAWCWYRVVAALRAAGHRATALDMAASGAH-PARVDEVGTF  59
                  *       *:*:*  ***.* *:::  .  *.* **:.**:*:****  .   : ::  :

▼
SABP2-N.tabacum  YDYTLPLMELMESLSA-DEKVILVGHSLGGMNLGLAMEKYPQKIYAAVFLAAFMPDSVHN  114
A.thaliana       EQYSEPLTKLLTSLPN-DEKVVLVGHSFGGLNLAIAMEKFPKKISVAVFLTAFMPDTEHS  118
M.esculenta      DEYSEPLLTFMESLPQ-GEKVILVGESCGGLNIAIAADKYPEKIAAAVFQNSLLPDTKHK  113
H.brasiliensis   DEYSEPLLTFLEALPP-GEKVILVGESCGGLNIAIAADKYCEKIAAAVFHNSVLPDTEHC  113
PIR7B            EEYSRPLLDAVAAAAAPGERLVLVGHSHGGLSVALAMERFPDKVAAAVFVAAAMPCVGKH  119
                  :*:  **      :  :  .*:::***.* **:.:.:* :::  .*: .***   : :*   :

SABP2-N.tabacum  SSFVLEQYN-ERTPAENWLDTQFLPYGS-PEEPLTSMFFGPKFLAHKLYQLCSPEDLALA  172
A.thaliana       PSFVLDKFG-SNMPQEAWMGTEFEPYGS-DNSGLS-MFFSPDFMKLGLYQLSPVEDLELG  175
M.esculenta      PSYVVDKLM-EVFP--DWKDTEYFEFSNSNGETITGMVLGLKLMRENLYTICPPEDYELA  170
H.brasiliensis   PSYVVDKLM-EVFP--DWKDTTYFTYTK-DGKEITGLKLGFTLLRENLYTLCGPEEYELA  169
PIR7B            MGVPTEEFMRRTAPEGLLMDCEMVAINNSQGSGVA-INLGPTFLAQKYYQQSPAEDLALA  178
                  .  ::    *      .      . . .::  :  :.   ::   *  . *:  *.

▼
SABP2-N.tabacum  SSLVRPSSLFMEDLSKAK--YFTDERFGSVKRVYIVCTEDKGIPEEFQRWQIDNIGVTEA  230
A.thaliana       LLLMRPGSLFINDLSKMK--NFSDEGYGSVPRVFIVCKEDKAIPEERQRWMIDNFPVNLV  233
M.esculenta      KMLTRRGSLFQSILAQRE--KFTEKGYGSIKKIYVWTGDDKIFLPEFQLWQIENYKPDLV  228
H.brasiliensis   KMLTRKGSLFQNILAKRP--FFTKEGYGSIKKIYVWTDQDEIFLPEFQLWQIENYKPDKV  227
PIR7B            KMLVRPGNQFMDDPVMKDESLLTNGNYGSVKKVYVIAKADSSSTEEMQRWMVAMSPGTDV  238
                  * *  ..  * .           ::.  :**: ::::    *.   * * * :        .

▼
SABP2-N.tabacum  IEIKGADHMAMLCEPQKLCASLLEIAHKYN  260
A.thaliana       MEMEETDHMPMFCKPQQLSDYFLKIADKFV  263
M.esculenta      FRVMGGDHKLQLTKTNEIAGILQKVADIYA  258
H.brasiliensis   YKVEGGDHKLQLTKTKEIAEILQEVADTYN  257
PIR7B            EEIAGADHAVMNSKPRELCDILIKIANKYE  268
                  .:      **       :...::.    : ::*. :
```

Figure 5

← SABP2

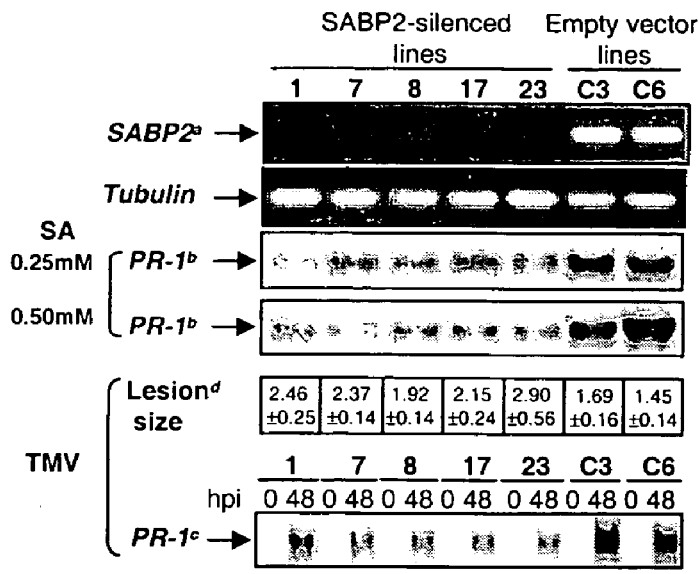
Fig. 8A
Fig. 8B
Fig. 8C
Fig. 8D
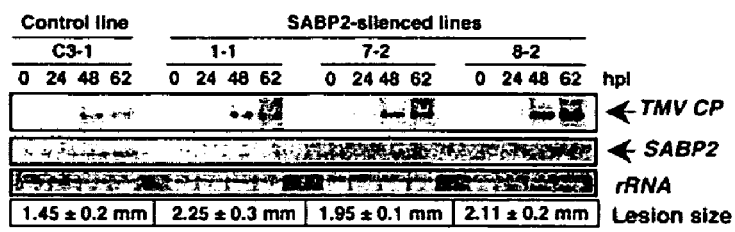
Fig. 8E
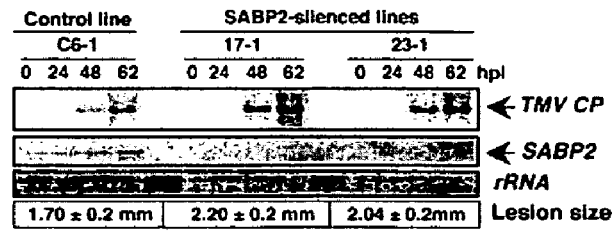
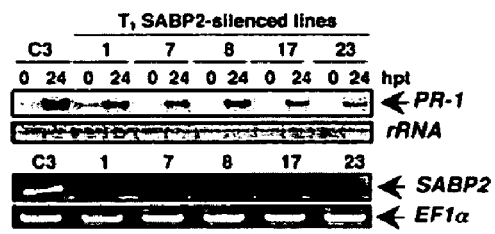
Fig. 8F
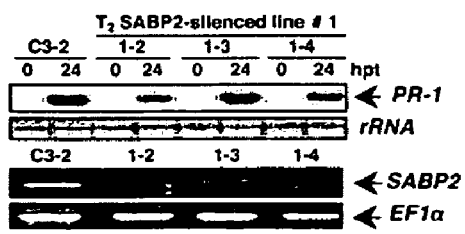
Fig. 8G Fig. 9A
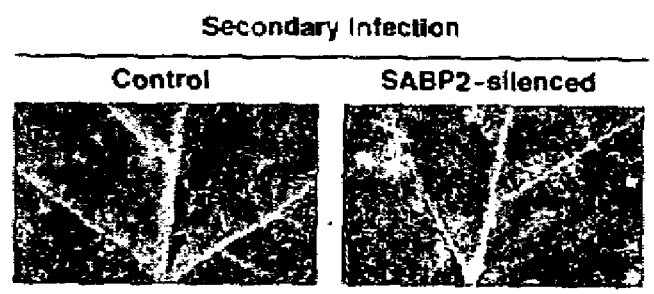
Fig. 9B
Fig. 9C
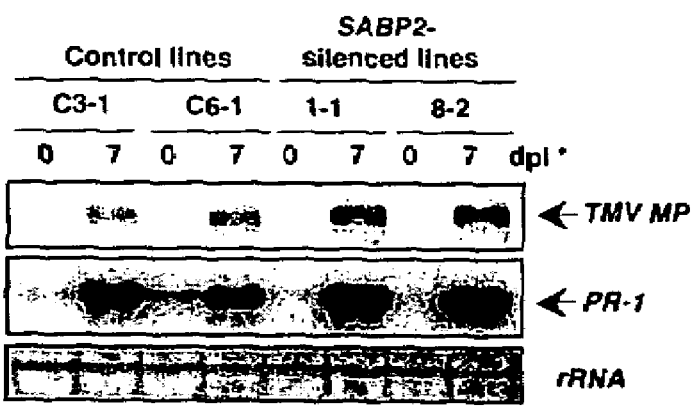

SALICYLIC ACID-BINDING PROTEIN ENCODING NUCLEIC ACID, SABP2, AND METHODS OF USE THEREOF

This application is a continuation in part of international application PCT/US02/26312, filed Aug. 16, 2002, which in turn claims priority to U.S. provisional Application, 60/312,863 filed Aug. 16, 2001, the entire contents of which are incorporated by reference herein.

Pursuant to 35 U.S.C. §202(c), it is acknowledged that the U.S. Government has certain rights in the invention described herein, which was made in part with funds from the National Science Foundation, Grant No. MCB-0196046, IBN-0110272, and IBN-0241531.

FIELD OF THE INVENTION

This invention relates to proteins involved in signal transduction pathways in higher plants. More specifically, the invention provides a novel nucleic acid molecule encoding a protein involved in stress and disease resistance pathways in multicellular plants. The biological molecules of the invention may be used to advantage to (i) create transgenic plants, (ii) identify compounds that induce or enhance disease resistance in plants, and (iii) elucidate the molecular mechanisms responsible for modulation of salicylic acid-mediated disease resistance in plants.

BACKGROUND OF THE INVENTION

Several publications are referenced in this application by author name and year of publication in parentheses in order to more fully describe the state of the art to which this invention pertains. Full citations for these references are found at the end of the specification. Several patent documents are also referenced to facilitate the practice of the present invention. The disclosure of each of these publications and patent documents is incorporated by reference herein.

Plants can respond to infection by microbial pathogens through the activation of a variety of defense responses. At the sites of infection, a hypersensitive response (HR) is often initiated. The hallmark of this response is the formation of necrotic lesions, a process that is likely due to programmed host cell death. In addition, associated with the HR is the restriction of growth and spread of pathogens. Frequently, defense responses are also activated in tissues distal to the sites of infection according to a phenomenon known as systemic acquired resistance (SAR). Development of SAR results in an enhanced and long-lasting resistance to secondary challenge by the same or even unrelated pathogens. Associated both with HR (and associated local resistance) and with SAR is the expression of pathogenesis-related (PR) genes, several of whose products have been shown to have antimicrobial activity (for review, see Klessig and Malamy, 1994; Hammond-Kosach and Jones, 1996; Durner et al., 1997; Dempsey et al., 1999).

A mounting body of evidence indicates that salicylic acid (SA) plays a key role in the activation of certain defense responses in a number of dicotyledonous species. For example, rises in endogenous SA levels correlate with the induction of PR genes and development of resistance in tobacco and cucumber (Malamy et al., 1990 and 1992; Metraux et al., 1990; Rasmussen et al., 1991). In addition, several mutants of Arabidopsis (e.g., cpr's, lsd's, acd's) have been isolated which constitutively express PR genes and show enhanced resistance. They also demonstrate elevated levels of SA (Bowling et al., 1994; Dietrich et al., 1994; Greenberg et al., 1994; Yoshioka et al., 2001). Conversely, Arabidopsis mutants defective in SA signal transduction (e.g., npr1, nim1, sai1) exhibit enhanced susceptibility to pathogens (Cao et al., 1994; Delaney et al., 1995; Shah et al., 1997). Exogenously applied SA also induces PR gene expression and enhanced resistance in tobacco (White, 1979; Antoniw and White, 1980) and a variety of other plants (for review, see Klessig and Malamy, 1994; Durner et al., 1997). Furthermore, transgenic Arabidopsis and tobacco plants that express the bacterial salicylate hydroxylase (nahG) gene, whose product converts SA into biologically inactive catechol, fail to develop SAR and show increased susceptibility to primary infections by both virulent and avirulent pathogens (Gaffney et al., 1993; Delaney et al., 1994).

During the past several years, attempts to elucidate the mechanisms of SA action in plant disease resistance have been made by identifying the cellular components with which SA interacts. Initial studies led to the identification of a SA-binding protein, SABP, that was later shown to be a catalase (CAT) (Chen and Klessig, 1991; Chen et al., 1993a). Further analysis demonstrated that SA inhibited tobacco catalase activity in suspension cells and in crude leaf extracts. SA also inhibited the purified enzyme (Chen et al., 1993b; Conrath et al., 1995; Durner and Klessig, 1996). Thus, it was proposed that increases in SA after pathogen infection might inhibit catalase activity, producing elevated levels of $H_2O_2$ that could activate certain defense responses, including PR gene expression. Supporting this hypothesis was the observation that prooxidants induced PR-1 gene expression (Chen et al., 1993b), while antioxidants suppressed the SA-mediated expression of PR-1 genes (Conrath et al., 1995; Wendehenne et al., 1998). In addition, the other major $H_2O_2$-scavenging enzyme, ascorbate peroxidase (APX), was subsequently shown to be inhibited by SA (Durner and Klessig, 1995).

In contrast, several other studies have questioned the role of $H_2O_2$ and the SA-mediated inhibition of CAT and APX during the activation of defense responses. No detectable increases in $H_2O_2$ levels were found during the establishment of SAR (Neuenschwander et al., 1995) and significant reductions in CAT activity were not observed in tobacco infected with Pseudomonas syringae or in leaf discs pretreated with SA (Bi et al., 1995). In addition, $H_2O_2$ and $H_2O_2$-inducing chemicals were unable to induce PR-1 gene expression in NahG transgenic plants (Bi et al., 1995; Neuenschwander et al., 1995). Moreover, high concentrations of $H_2O_2$ (150 mM–1000 mM) were shown to induce SA accumulation (Neuenschwander et al., 1995; León et al., 1995; Summermatter et al., 1995). Finally, transgenic plants having significantly lower CAT activity via transformation with CAT antisense or cosuppressing sense constructs, did not exhibit constitutive PR-1 gene expression unless there was concurrent development of necrosis (Chamnonpol et al., 1996; Takahashi et al., 1997). From these results, it appears that $H_2O_2$ acts upstream of SA in the signal transduction cascade rather than, or in addition to, acting downstream of SA.

One possible explanation for these conflicting findings is that SA and $H_2O_2$ are involved in a self-amplifying feedback loop (Van Camp, 1998; Draper, 1997; Shirasu et al., 1997). An alternative mechanism through which SA-mediated inhibition of CAT may signal defense responses is via the generation of SA free radicals, which could then activate a lipid peroxidation pathway (Durner and Klessig, 1996, Anderson et al., 1998). However, this possibility remains a topic of debate (Tenhaken and Rübel, 1997).

Taken together, these studies suggest that the activation of defense responses is mediated through the interaction of SA with other cellular factors, rather than, or in addition to interactions with CAT and APX. Thus, the isolation and identification of additional cellular factors associated with SA action in plant disease resistance is essential for elucidating the molecular mechanisms directing SA-mediated defense responses.

SUMMARY OF THE INVENTION

In accordance with the present invention, a novel nucleic acid molecule, SABP2, is provided. SABP2 encodes the novel high-affinity salicylic acid-binding protein 2 (SABP2) which is involved in the SA-mediated signal transduction pathway leading to defense responses to pathogen infection in higher plants.

In one aspect of the invention, an isolated nucleic acid molecule comprising an SABP2-encoding nucleic acid sequence is provided. In a preferred embodiment, the nucleic acid molecule is isolated from a plant and has the SABP2-encoding nucleic acid sequence of SEQ ID NO: 1. The nucleic acid molecules of the invention may be inserted into an expression vector, such as a plasmid or viral vector, and may further be transformed into a host cell or plants. Exemplary host cells and plants include tobacco, Arabidopsis, rice, maize, wheat, tomato, potato, barley, canola, bacteria, yeast, insect and mammalian cells.

According to another aspect of the invention, an isolated SABP2 polypeptide encoded by the nucleic acid sequence of SEQ ID NO: 1 is provided. In a preferred embodiment, the SABP2 polypeptide comprises the amino acid sequence of SEQ ID NOS: 2 and has enzymatic activity. In another embodiment of the invention, antibodies immunologically specific for at least one epitope of an SABP2 polypeptide are also provided.

According to yet another aspect of the invention, methods for identifying agents which modulate SABP2 function are provided. The methods comprise introducing SABP2-encoding nucleic acid molecules into a host cell, treating the cells or resulting plant with agents suspected of modulating SABP2 function and assaying SABP2 function in the presence and absence of the agent. The agents may modulate one or more of SABP2 expression, SABP2 binding affinity, or SABP2 enzymatic activity.

According to a preferred aspect of the invention, a method is provided to enhance resistance of a plant to plant pathogens or other disease causing agents comprising overexpressing a SABP2-encoding nucleic acid molecule having the sequence of SEQ ID NO: 1. In another embodiment of the invention, SABP2 expression is enhanced by the addition of an agent that enhances SABP2 expression in a host cell.

According to yet another aspect of the invention, a method is provided to inhibit SABP2 function in a plant. This method comprises introducing a mutated SABP2-encoding nucleic acid molecule into a plant which encodes a non-functional SABP2 protein. In a preferred embodiment, the SABP2-encoding nucleic acid molecule is an antisense molecule of SEQ ID NO: 1. Alternatively, methods for inhibition of SABP2 expression comprise introduction of nucleic acid constructs effective to cause dsRNA mediated gene silencing of the SABP2 gene (Smith et al., 2000; Wesley et al., 2001).

According to another aspect of the present invention, transgenic plants comprising SEQ ID NO: 1 are provided. The transgenic plants of the invention exhibit enhanced disease resistance. Knock-out plants wherein SABP2 expression has been eliminated are also provided. Also within the scope of the invention are transgenic plants comprising variants of SEQ ID NO: 1 encoding proteins having altered SABP2 function.

In a further embodiment of the invention, the screening methods provided above are performed employing nucleic acids, proteins and antibodies encoded by the SABP2 homologs and functional orthologs identified in *Arabidopsis* (e.g., AtSB2L5) and other species. GenBank Accession numbers of exemplary nucleic acid sequences are provided in Table IV. These functionally equivalent homologs to SABP2 may also be used to modulate disease resistance in higher plants.

BRIEF DESCRIPTION OF THE DRAWINGS

FIG. 4 shows the nucleotide and deduced amino acid sequences of a SABP2 clone isolated from leaves of tobacco (SEQ ID NOS: 1 and 2). The five peptide sequences obtained by microsequencing are underlined in the deduced SABP2 amino acid sequence.

FIG. 5 shows the amino acid sequence homology of SABP2 to hydroxynitrile lyases and eukaryotic esterases. Aligned from top to bottom are the deduced amino acid sequence of SABP2 (SEQ ID NO: 2), alpha-hydroxynitrile lyase (S-acetone-cyanohydrin lyase) from *Manihot esculenta* (SEQ ID NO: 3), S-acetone-cyanohydrin lyase from *Hevea brasiliensis* (SEQ ID NO: 4), a putative S-acetone-cyanohydrin lyase from *Arabidopsis thaliana* (SEQ ID NO: 5) and an esterase from rice, PIR7B (SEQ ID NO: 6). The residues of the catalytic triad are indicated by triangles and the lipase signature sequence of SABP2 is boxed.

FIG. 6A shows an in gel lipase assay of purified recombinant His6-SABP2 fractionated on an SDS-PAGE and then reacted with the synthetic lipase/esterase substrate, MUF butyrate. The fluorescence at the position of SABP2 in the gel is due to the release of MUF by SABP2's lipase/esterase activity. FIG. 6B is a graph which shows that SABP2 lipase activity is stimulated in the presence of salicylic acid. Lipase assays were performed with purified recombinant SABP2 (rSABP2) in either 50 mM bicine, pH 8.0 or 50 mM Tris-Cl, pH 8.0 containing 0.05% Triton-X100 and 1 mM lipase substrate. Results from assays using para-nitrophenol palmitate (pNPP) as the substrate in the presence or absence of SA are presented as an average with three separate preparations of recombinant SABP2, while those using pNP myristate (pNPM) as the substrate were done with one preparation of rSABP2. Lipase activity detected in each sample is presented in relative units and the fold stimulation by SA is shown in parentheses above the bars. One relative unit is the amount of enzyme that releases 0.017 mol/min of p-nitrophenol. Note that when 50 mM bicine is replaced with 50 mM Tris-HCl pH 8.0, SABP2 does not bind SA.

Figure 7A:
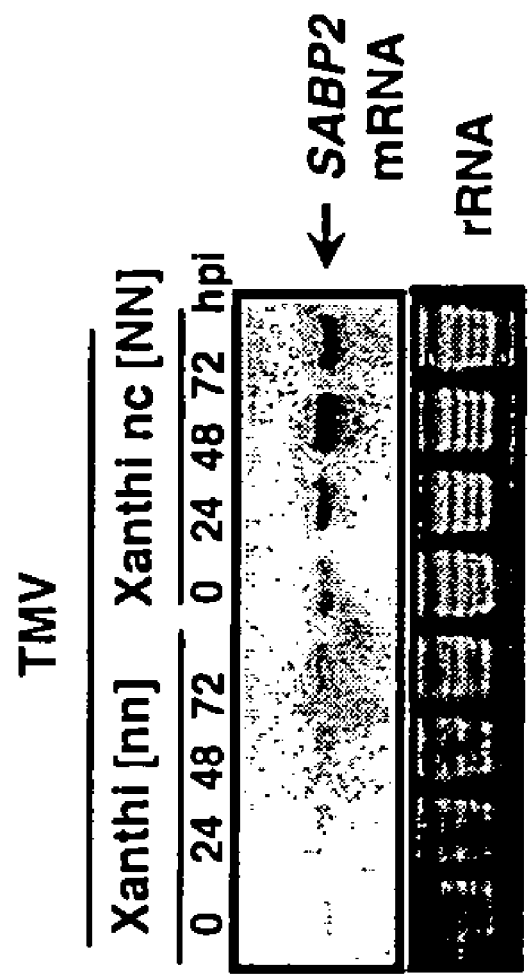
Figure 7B:
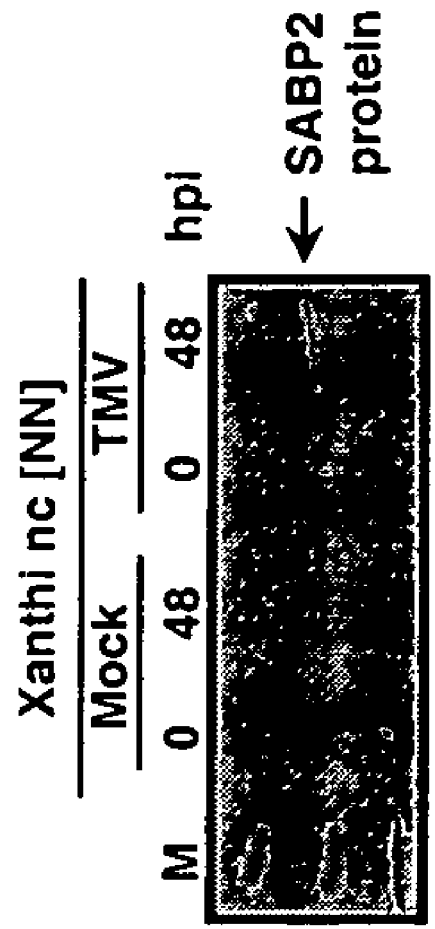

FIGS. 7A and 7B show blots of SABP2 induction at the mRNA [7A] and protein [7B] levels by TMV infection of resistant Xanthi nc [NN], but not susceptible Xanthi [nn], *Nicotiana tabacum*. Antibody against SABP2 was used in the immunoblot shown in FIG. 7B.

FIGS. 8A–8G show that silencing of SABP2 suppresses disease resistance (as measured by tobacco mosaic virus (TMV) lesion size, and level of coat protein (CP) mRNA) and also suppresses PR-1 gene induction by SA and by TMV. FIG. 8A—SABP2 expression was monitored by RT-PCR using beta-tubulin as an internal control. FIG. 8B—24 hours post treatment with SA; induction of PR-1 expression with SA and TMV was monitored by northern (RNA blot) analysis, using EtBr stained rRNA as control for equal loading (not shown). FIG. 8C—TMV-induced lesion size in mm. FIG. 8D—Analysis of 36 hours post infection time point confirmed suppression of PR-1 induction by TMV in SABP2-silenced lines (data not shown). FIG. 8E shows RNA blot analysis of TMV CP and SABP2 transcript accumulation and size of TMV induced lesion in control plants (transformed with empty vector) and various SABP2-silenced lines from the $T_2$ generation. Total RNA was isolated from TMV-inoculated leaves harvested at the indicated time points. Following transfer, the membrane was hybridized with probes for the SABP2 and TMV CP. The size of TMV-induced lesions on these control and SABP2-silenced lines was determined by measuring an average of 50 lesions per line. Lesion diameter is presented +/− standard deviation. FIG. 8F shows a comparison of SA-induced PR-1 expression and SABP2 silencing in the $T_1$ generations of control and SABP2-silenced lines. Total RNA was isolated from all lines at 0 and 24 h post treatment (hpt) with 0.25 mM SA. PR-1 expression was monitored by RNA blot analysis while SABP2 expression was determined by RT-PCR analysis using cDNA generated from untreated plants. The level of EF1α product was monitored as an internal control to normalize the amount of cDNA template. Please note that PR-1 induction by SA was tested at least twice in two independent experiments for both the $T_1$ and $T_2$ generations to confirm the difference in SA responsiveness. FIG. 8G shows a comparison of SA-induced PR-1 expression and SABP2 silencing in three different $T_2$ generation plants for line # 1. See (FIG. 8F) above for details.

FIGS. 9A–C show that silencing SABP2 expression blocks development of systemic acquired resistance (SAR). FIG. 9A shows the size of primary lesions developed by TMV-inoculated control and SABP2-silenced plants ($T_2$ generation), measured at 7 dpi. Seven days after the primary TMV infection, the upper previously uninoculated leaves received a secondary inoculation with TMV. The diameter of the secondary lesions was then measured 7 days after the challenge infection. Each value represents the average size (in mm +/− standard deviation) of 50 lesions per line. FIG. 9B shows morphology of TMV-induced lesions in control and SABP2-silenced tobacco. The leaves were photographed 7 days after a secondary infection with TMV. FIG. 9C shows RNA blot analysis of TMV movement protein (MP) and PR-1 transcript accumulation in control and SABP2-silenced $T_2$ lines. Total RNA was isolated from systemic leaves prior to (0 day) or 7 days after a secondary inoculation with TMV (*). Following transfer, the membrane was hybridized with probes for the TMV MP and PR-1.

Figure 10:
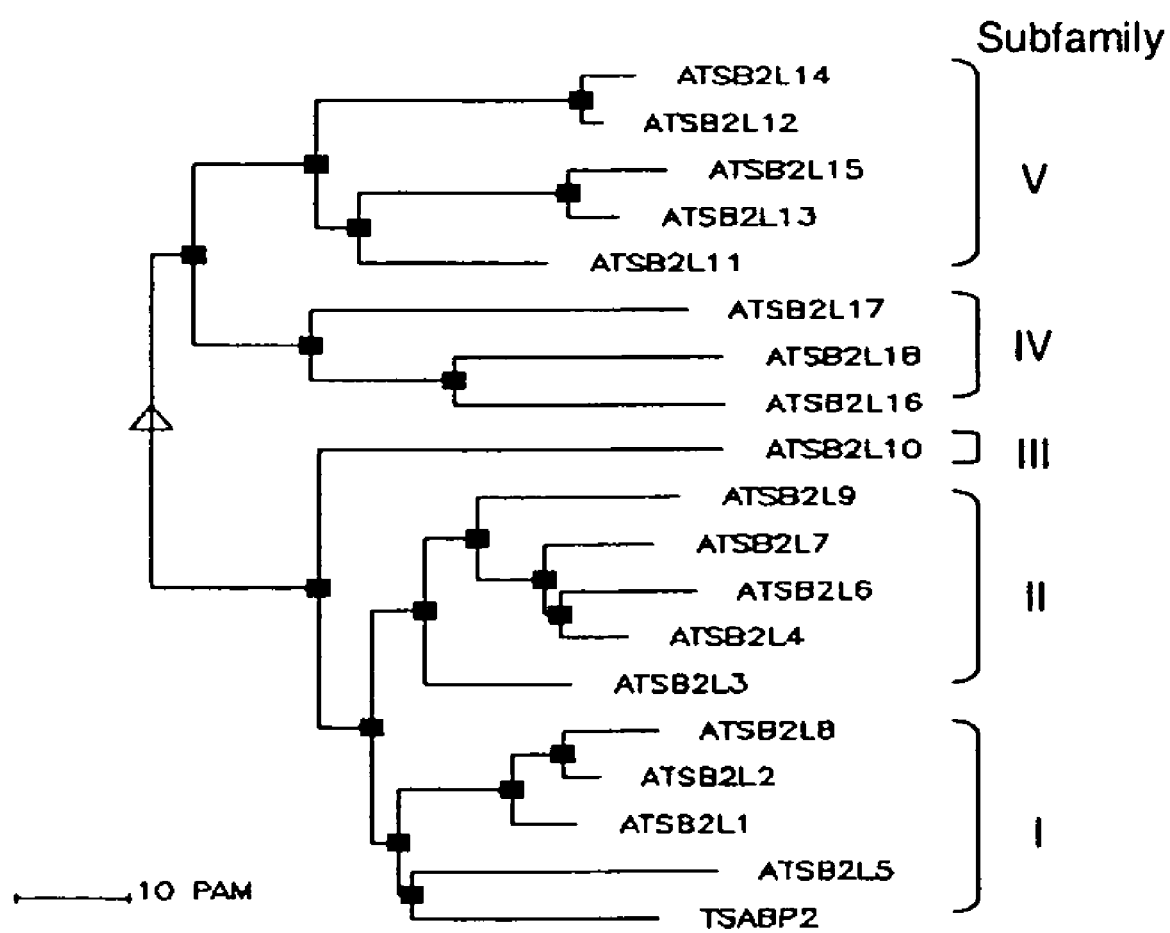

FIG. 10 shows the relationship of *Arabidopsis thaliana* SABP2-like (AtSB2L) proteins to each other and to tobacco SABP2 (TSABP2)

DETAILED DESCRIPTION OF THE INVENTION

SA is a key component in the signal transduction pathway(s) leading to activation of certain defense responses in plants after pathogen attack. Previous studies have identified several proteins, including catalase and ascorbate peroxidase, through which the SA signal might act. A novel nucleic acid molecule encoding the SA-binding protein 2, SABP2, is described herein. SABP2 was identified through the use of a high specific activity ligand, [$^3$H]-SA (15–30 Ci/mmole). SABP2, which is soluble, differs significantly from a previously-described SABP, which was subsequently shown to be a catalase. For example, SABP2 is much less abundant in leaf tissue than the catalase, and has an apparent native mass ($M_r$) of between about 20 and 40 kDa, as compared with the native molecular mass of catalase, which is approximately 240 kDa. The SABP2 from tobacco reversibly binds SA with an apparent $K_d$ of approximately 90 nM, an affinity that is 100–150 fold higher than that between SA and tobacco catalase. Strikingly, SABP2, isolated from plant extracts, exhibits an even greater affinity (approximately 15-fold) for the synthetic functional SA analog, benzothiadiazole (BTH), which is a more effective inducer than SA of PR gene expression and disease resistance in monocots as well as dicots (Görlach, et al., 1996; Lawton et al., 1996; Morris et al, 1998; Benhamou and Bélanger, 1998).

SABP2 preferentially binds SA and active analogs that induce PR gene expression and enhanced disease resistance. Exemplary analogs include without limitation 5-chlorosalicylic acid (5-CSA) and 2,6-dihydroxybenzoic acid 2,6-DHBA). SABP2 shows only minimal binding to inactive analogs such as 4-hydroxybenzoic acid (4-HBA). See Table IV. Unexpectedly, the recombinant, purified SABP2 did not bind BTH. This likely reflects the fact that synthetic BTH is an S-methyl ester which is converted by plant esterases into the active acid form (Kaji, M., et al., 1997; Ishii, H., et al., 1999; Pillonel, C. 2001). Presumably esterases in the partially purified SABP2 preparations convert BTH to its active form before it is bound by SABP2, while such esterases are not present in the purified SABP2 produced in *E. coli*.

The novel SABP2 encoding nucleic acid molecules of the invention may be used to advantage for expression of SABP2 in large quantities. They may also be used to generate transgenic plants having altered expression levels of SABP2. Such transgenic plants may be genetically engineered to overexpress or underexpress SABP2. Alternatively, knockout plants may be created wherein endogenous SABP2 gene expression is abolished. In yet another aspect, plant expression vectors can be generated wherein expression of SABP2 is under the control of an inducible promoter.

In yet another embodiment of the invention, methods are provided for identifying agents or compounds which have binding affinity for SABP2. Such agents may be used in methods for controlled modulation of plant defense responses. Exemplary agents may alter SABP2 enzymatic activity (e.g. stimulate or inhibit) and/or bind tightly to SABP2 and compete for SA binding.

Although the SABP2 encoding nucleic acid from tobacco is described and exemplified herein, this invention is intended to encompass nucleic acid molecules from other plant species that are sufficiently similar to be used interchangeably with tobacco SABP2 encoding nucleic acids for the purposes described below. For example, *Arabidopsis*, like tobacco, have a SABP2-like activity (Du and Klessig, 1997). *Arabidopsis* contains 18 full-length homologs of SABP2, two of which (AtSB2L5 and AtSB2L9) bind SA (Table IV) and appear to be functional equivalents (orthologs) of SABP2. Thus, using the primers described herein, one may successfully isolate and utilize SABP2 homologs and possible orthologs from other plant species using the methods provided herein.

Finally, given the homology of human nucleic acids encoding proteins having function comparable to SABP2, identification and characterization of such molecules is encompassed within the present invention. For example, lecithin (phosphatidylcholine) cholesterol acetyl transferase (LCAT, GenBank Accession No. XO4981; SEQ ID NO: 31), an enzyme found in mammals, including humans, may also be regulated by SA and analogs thereof.

Exemplary methods for assessing the activity of molecules such as LCAT include SA-binding assays, such as the assay set forth in Example II herein. Additionally, SA or aspirin's effect on the enzymatic activity of human LCAT can be determined by pre-treating purified LCAT protein or extracts containing LCAT with 0.001 mM–1 mM of SA or aspirin for 30–180 minutes at 22–37° C. before adding this pre-treated protein to the standard assay for LCAT esterase activity described by Nakayama et al., 1984. The concentration of SA or aspirin in the pre-treatment will be maintained in the enzyme assay reaction.

It is known that aspirin (acetyl SA: ASA) and SA reduces the risk of heart disease and stroke. It is also believed that this protective effect of aspirin/SA is due to its ability to inhibit the aggregation of neutrophils and platelets (Weissman et al., 1991; Abramson et al., 1985). However, it is also likely that aspirin/SA exerts its protective effects by stimulating the activity of LCAT. The finding that the critical SA-binding protein for plant disease resistance responses, namely SABP2, shares both esterase/lipase activity and sequence homology with LCAT, as well as membership in the same super family of α/β fold hydrolases suggests that aspirin/SA binds LCATs. Furthermore, SA and aspirin were shown to elevate LCAT activity and reduce serum cholesterol in rats (Nakayama et al. 1984) while over expression of LCAT in rabbits (Hoeg et al., 1996) or overexpression of the combination of LCAT and cholesterol ester transfer protein in mice (Foeger et al., 1999) were shown to protect these transgenic mammals against atherosclerosis. Therefore, it is suspected that aspirin/SA bind mammalian (e.g. human) LCATs and thereby enhance their enzymatic activity. This enhanced activity reduces the risk of atherosclerosis and associated heart disease and strokes. Thus, in accordance with the present invention, LCAT encoding sequences will also be assessed for SA binding function and enzymatic activity.

I. Definitions

The following definitions are provided to facilitate an understanding of the present invention:

The term "SABP2 function" is used herein to refer to any SABP2 activity, including without limitation expression levels of SABP2, enzymatic activity, and salicylic acid or analog binding.

An SABP2 homolog is any protein or DNA encoding the same which has similar structural properties (such as sequence identity and folding) to SABP2. An SABP2 ortholog is any protein or DNA encoding the same which has similar structural properties, and similar function (such as expression, enzymatic activity, and binding) to SABP2.

The term "pathogen-inoculated" refers to the inoculation of a plant with a pathogen.

The term "disease defense response" refers to a change in metabolism, biosynthetic activity or gene expression that enhances a plant's ability to suppress the replication and spread of a microbial pathogen (i.e., to resist the microbial pathogen). Examples of plant disease defense responses include, but are not limited to, production of low molecular weight compounds with antimicrobial activity (referred to as phytoalexins) and induction of expression of defense (or defense-related) genes, whose products include, for example, peroxidases, cell wall proteins, proteinase inhibitors, hydrolytic enzymes, pathogenesis-related (PR) proteins and phytoalexin biosynthetic enzymes, such as phenylalanine ammonia lyase and chalcone synthase (Dempsey and Klessig, 1995; Dempsey et al., 1999). Such defense responses appear to be induced in plants by several signal transduction pathways involving secondary defense signaling molecules produced in plants. Certain of these defense response pathways are SA dependent, while others are partially SA dependent and still others are SA independent. Agents that induce disease defense responses in plants include, but are not limited to: (1) microbial pathogens, such as fungi, oomycetes, bacteria and viruses; (2) microbial components and other defense response elicitors, such as proteins and protein fragments, small peptides, β-glucans, elicitins, harpins and oligosaccharides; and (3) secondary defense signaling molecules produced by the plant, such as SA, $H_2O_2$, ethylene, jasmonates, and nitric oxide.

The terms "defense-related genes" and "defense-related proteins" refer to genes or their encoded proteins whose expression or synthesis is associated with or induced after infection with a pathogen to which the plant is usually resistant.

A "transgenic plant" refers to a plant whose genome has been altered by the introduction of at least one heterologous nucleic acid molecule.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it would be associated in its natural state (i.e., in cells or tissues). An "isolated nucleic acid" (either DNA or RNA) may further represent a molecule produced directly by biological or synthetic means and separated from other components present during its production.

The terms "percent similarity", "percent identity" and "percent homology" when referring to a particular sequence are used as set forth in the University of Wisconsin GCG software program.

The term "substantially pure" refers to a preparation comprising at least 50–60% by weight of a given material (e.g., nucleic acid, oligonucleotide, protein, etc.). More preferably, the preparation comprises at least 75% by weight, and most preferably 90–95% by weight of the given compound. Purity is measured by methods appropriate for the given compound (e.g. chromatographic methods, agarose or polyacrylamide gel electrophoresis, HPLC analysis, and the like).

A "replicon" is any genetic element, for example, a plasmid, cosmid, bacmid, phage or virus, that is capable of replication largely under its own control. A replicon may be either RNA or DNA and may be single or double stranded.

A "vector" is any vehicle to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide," as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and method of use. For example, for diagnostic applications, depending on the complexity of the target sequence, the oligonucleotide probe typically contains 15–25 or more nucleotides, although it may contain fewer nucleotides. The probes herein are selected to be "substantially" complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically. The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as appropriate temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15–25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "promoter region" refers to the 5' regulatory regions of a gene (e.g., CaMV 35S promoters and/or tetracycline repressor/operator gene promoters).

As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by calorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "DNA construct" refers to a genetic sequence used to transform plants and generate progeny transgenic plants. These constructs may be administered to plants in a viral or plasmid vector. Other methods of delivery such as *Agrobacterium* T-DNA mediated transformation and transformation using the biolistic process are also contemplated to be within the scope of the present invention. The transforming DNA may be prepared according to standard protocols such as those set forth in "Current Protocols in Molecular Biology", eds. Frederick M. Ausubel et al., John Wiley & Sons, 1995.

The phrase "double-stranded RNA mediated gene silencing" refers to a process whereby target gene expression is suppressed in a plant cell via the introduction of nucleic acid constructs encoding molecules which form double-stranded RNA structures with target gene encoding mRNA which are then degraded.

The term "co-suppression" refers to a process whereby expression of a gene, which has been transformed into a cell or plant (transgene), causes silencing of the expression of endogenous genes that share sequence identity with the transgene. Silencing of the transgene also occurs.

Amino acid residues are identified in the present application according to the three-letter or one-letter abbreviations in the following Table:

TABLE I

| Amino Acid | 3-letter Abbreviation | 1-letter Abbreviation |
|---|---|---|
| L-Alanine | Ala | A |
| L-Arginine | Arg | R |

TABLE I-continued

| Amino Acid | 3-letter Abbreviation | 1-letter Abbreviation |
|---|---|---|
| L-Asparagine | Asn | N |
| L-Aspartic Acid | Asp | D |
| L-Cysteine | Cys | C |
| L-Glutamine | Gln | Q |
| L-Glutamic Acid | Glu | E |
| Glycine | Gly | G |
| L-Histidine | His | H |
| L-Isoleucine | Ile | I |
| L-Leucine | Leu | L |
| L-Methionine | Met | M |
| L-Phenylalanine | Phe | F |
| L-Proline | Pro | P |
| L-Serine | Ser | S |
| L-Threonine | Thr | T |
| L-Tryptophan | Trp | W |
| L-Tyrosine | Tyr | Y |
| L-Valine | Val | V |
| L-Lysine | Lys | K |

Amino acid residues described herein are preferred to be in the "L" isomeric form. However, residues in the "D" isomeric form may be substituted for any L-amino acid residue, provided the desired properties of the polypeptide are retained. All amino-acid residue sequences represented herein conform to the conventional left-to-right amino-terminus to carboxy-terminus orientation.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, or the addition of stabilizers.

"Mature protein" or "mature polypeptide" shall mean a polypeptide possessing the sequence of the polypeptide after any processing events that normally occur to the polypeptide during the course of its genesis, such as proteolytic processing from a polyprotein precursor. In designating the sequence or boundaries of a mature protein, the first amino acid of the mature protein sequence is designated as amino acid residue 1. As used herein, any amino acid residues associated with a mature protein not naturally found associated with that protein that precedes amino acid 1 are designated amino acid −1, −2, −3 and so on. For recombinant expression systems, a methionine initiator codon is often utilized for purposes of efficient translation. This methionine residue in the resulting polypeptide, as used herein, would be positioned at −1 relative to the mature SABP2 protein sequence.

A low molecular weight "peptide analog" shall mean a natural or mutant (mutated) analog of a protein, comprising a linear or discontinuous series of fragments of that protein and which may have one or more amino acids replaced with other amino acids and which has altered, enhanced or diminished biological activity when compared with the parent or nonmutated protein.

The present invention also includes active portions, fragments, derivatives and functional or non-functional mimetics of SABP2-related polypeptides, or proteins of the invention. An "active portion" of such a polypeptide means a peptide that is less than the full length polypeptide, but which retains measurable biological activity.

A "fragment" or "portion" of an SABP2-related polypeptide means a stretch of amino acid residues of at least about five to seven contiguous amino acids, often at least about seven to nine contiguous amino acids, typically at least about nine to thirteen contiguous amino acids and, most preferably, at least about twenty to thirty or more contiguous amino acids. Fragments of the SABP2-related polypeptide sequence, antigenic determinants, or epitopes are useful for eliciting immune responses to a portion of the SABP2-related protein amino acid sequence for the effective production of immunospecific anti-SABP2 antibodies.

Different "variants" of the SABP2-related polypeptides exist in nature. These variants may be alleles characterized by differences in the nucleotide sequences of the gene coding for the protein such as homologs and orthologs, or may involve different RNA processing or post-translational modifications. The skilled person can produce variants having single or multiple amino acid substitutions, deletions, additions or replacements. These variants may include but are not limited to: (a) variants in which one or more amino acids residues are substituted with conservative or non-conservative amino acids, (b) variants in which one or more amino acids are added to the polypeptide, (c) variants in which one or more amino acids include a substituent group, and (d) variants in which the polypeptide is fused with another peptide or polypeptide such as a fusion partner, a protein tag or other chemical moiety, that may confer useful properties to the SABP2-related polypeptide, such as, for example, an epitope for an antibody, a polyhistidine sequence, a biotin moiety and the like. Other SABP2-related polypeptides of the invention include variants in which amino acid residues from one species are substituted for the corresponding residue in another species, either at the conserved or non-conserved positions. In another embodiment, amino acid residues at non-conserved positions are substituted with conservative or non-conservative residues. The techniques for obtaining these variants, including genetic (suppressions, deletions, mutations, etc.), chemical, and enzymatic techniques are known to the person having ordinary skill in the art. To the extent such allelic variations, analogues, fragments, derivatives, mutants, and modifications, including alternative nucleic acid processing forms and alternative post-translational modification forms, result in derivatives of the SABP2-related polypeptide that retain any of the functions of the SABP2-related polypeptide, they are included within the scope of this invention.

The term "functional" as used herein implies that the nucleic or amino acid sequence is functional for the recited assay or purpose.

The phrase "consisting essentially of" when referring to a particular nucleotide or amino acid means a sequence having the properties of a given SEQ ID NO. For example, when used in reference to an amino acid sequence, the phrase includes the sequence per se and molecular modifications that would not affect the basic and novel characteristics of the sequence.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "clone" or "clonal cell population" is a population of cells derived from a single cell or common ancestor by mitosis.

A "cell line" is a clone of a primary cell or cell population that is capable of stable growth in vitro for many generations.

An "immune response" signifies any reaction produced by an antigen, such as a viral or plant antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "antibody" or "antibody molecule" is any immunoglobulin, including antibodies and fragments thereof, that binds to a specific antigen, such as epitopes of an SABP2 binding protein. The term includes polyclonal, monoclonal, chimeric, and bispecific antibodies. As used herein, antibody or antibody molecule contemplates both an intact immunoglobulin molecule and an immunologically active portion of an immunoglobulin molecule such as those portions known in the art as Fab, Fab', F(ab')2 and F(v).

The following description sets forth the general procedures involved in practicing the present invention. To the extent that specific materials are mentioned, it is merely for purposes of illustration and is not intended to limit the invention. Unless otherwise specified, general biochemical and molecular biological procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1997) (hereinafter "Ausubel et al.") are used.

II. Preparation of SABP2 Encoding Nucleic Acid Molecules:

Nucleic acid molecules of the invention encoding SABP2 polypeptides may be prepared by two general methods: (1) synthesis from appropriate nucleotide triphosphates, or (2) isolation from biological sources. Both methods utilize protocols well known in the art. The availability of nucleotide sequence information, such as the DNA sequences encoding SABP2, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be used directly or purified according to methods known in the art, such as high performance liquid chromatography (HPLC).

Specific probes for identifying such sequences as the SABP2 encoding sequence may be between 15 and 40 nucleotides in length. For probes longer than those described above, the additional contiguous nucleotides are provided within SEQ ID NO: 1.

Additionally, cDNA or genomic clones having homology with SABP2 may be isolated from other species using oligonucleotide probes corresponding to predetermined sequences within the SABP2 nucleic acids of the invention. Such homologous sequences encoding SABP2 may be identified by using hybridization and washing conditions of appropriate stringency. For example, hybridizations may be performed, according to the method of Sambrook et al., *Molecular Cloning*, Cold Spring Harbor Laboratory (1989), using a hybridization solution comprising: 5×SSC, 5× Denhardt's reagent, 1.0% SDS, 100 µg/ml denatured, fragmented salmon sperm DNA, 0.05% sodium pyrophosphate and up to 50% formamide. Hybridization is carried out at 37–42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes–1 hour at 37° C. in 1×SSC and 1% SDS; (4) 2 hours at 42–65° C. in 1×SSC and 1% SDS, changing the solution every 30 minutes.

One common formula for calculating the stringency conditions required to achieve hybridization between nucleic acid molecules of a specified sequence homology (Sambrook et al., 1989) is as follows:

$$T_m = 81.5° C. + 16.6 \text{Log } [Na+] + 0.41(\% \ G+C) - 0.63(\% \text{ formamide}) - 600/\#bp \text{ in duplex}$$

As an illustration of the above formula, using [Na+]=[0.368] and 50% formamide, with GC content of 42% and an average probe size of 200 bases, the $T_m$ is 57° C. The $T_m$ of a DNA duplex decreases by 1–1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20–25° C. below the calculated $T_m$ of the hybrid. Wash conditions should be as stringent as possible for the degree of identity of the probe for the target. In general, wash conditions are selected to be approximately 12–20° C. below the $T_m$ of the hybrid. In regards to the nucleic acids of the current invention, a moderate stringency hybridization is defined as hybridization in 6×SSC, 5× Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5× Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5× Denhardt's solution, 0.5% SDS and 100 µg/ml denatured salmon sperm DNA at 42° C., and washed in 0.1×SSC and 0.5% SDS at 65° C. for 15 minutes.

The nucleic acid molecules described herein include cDNA, genomic DNA, RNA, and fragments thereof which may be single- or double-stranded. Thus, nucleic acids are provided having sequences capable of hybridizing with at least one sequence of a nucleic acid sequence, such as selected segments of the sequences encoding SABP2. Also contemplated in the scope of the present invention are methods of use for oligonucleotide probes which specifically hybridize with the DNA from the sequences encoding SABP2 under high stringency conditions. Primers capable of specifically amplifying the sequences encoding SABP2 are also provided. As mentioned previously, such oligonucleotides are useful as primers for detecting, isolating and amplifying sequences encoding SABP2.

Antisense nucleic acid molecules which may be targeted to translation initiation sites and/or splice sites to inhibit the expression of the SABP2 gene or production of its encoded protein are also provided. Such antisense molecules are typically between 15 and 30 nucleotides in length and often span the translational start site of SABP2 mRNA molecules. Antisense constructs may also be generated which contain the entire SABP2 cDNA in reverse orientation. Alternatively, the SABP2 gene may be silenced using a construct that contains both sense and complementary antisense sequences separated by an intron sequence. This "intron-spliced hairpin RNA" approach results in total silencing of the targeted gene by forming double stranded RNA (dsRNA) structures which are degraded by the host cell machinery (Smith et al., 2000; Wesley et al., 2001).

Also provided in accordance with the present invention are transgenic plants containing the aforementioned SABP2-encoding nucleic acids, or fragments or derivatives thereof. Such transgenic plants exhibiting enhanced disease resistance are described in greater detail below.

III. Preparation of SABP2 Proteins and Antibodies:

The SABP2 protein of the present invention may be prepared in a variety of ways, according to known methods. The protein may be purified from appropriate sources, e.g., plant cells or tissues as described in detail in Example 1. Example 1 describes the isolation of SABP2 from tobacco leaves, followed by purification by ammonium sulfate fractionation, ion-exchange, hydrophobic-interaction, and gel filtration chromatography.

Once nucleic acid molecules encoding SABP2 have been obtained, the SABP2 protein can be produced using in vitro expression methods known in the art. For example, a cDNA or gene may be cloned into an appropriate in vitro transcription vector, such a pSP64 or pSP65 vector for in vitro transcription, followed by cell-free translation in a suitable cell-free translation system, such as wheat germ or rabbit reticulocytes. In vitro transcription and translation systems are commercially available, e.g., from Promega Biotech, Madison, Wis. or BRL, Rockville, Md.

According to a preferred embodiment, larger quantities of SABP2 may be produced by expression in a suitable procaryotic or eucaryotic system. For example, part or all of a DNA molecule may be inserted into a plasmid vector adapted for expression in a bacterial cell (such as *E. coli*) or a yeast cell (such as *Saccharomyces cerevisiae*), or into a baculovirus vector for expression in an insect cell. Such vectors comprise the regulatory elements necessary for expression of the DNA in the host cell, positioned in such a manner as to permit expression of the DNA in the host cell.

Such regulatory elements required for expression include promoter sequences, translation control sequences and, optionally, enhancer sequences.

The SABP2 protein produced by gene expression in a recombinant procaryotic or eucaryotic system may be purified according to methods known in the art. In a preferred embodiment, the recombinant protein contains several (e.g., 6–8) histidine residues on the amino or carboxyl termini, which allows the protein to be affinity purified on a nickel column. If histidine tag-vectors are not used, an alternative approach involves purifying the recombinant protein by affinity separation, such as by immunological interaction with antibodies that bind specifically to the recombinant protein. Such methods are commonly used by skilled practitioners.

SABP2 protein, prepared by the aforementioned methods, may be analyzed according to standard procedures. Methods for analyzing the physical characteristics and biological activity of SABP2 are set forth in U.S. Pat. No. 6,136,552, the disclosure of which is incorporated by reference herein.

The present invention also provides antibodies capable of immunospecifically binding to proteins of the invention. Polyclonal or monoclonal antibodies directed toward SABP2 may be prepared according to standard methods. Monoclonal antibodies may be prepared according to general methods of Köhler and Milstein, following standard protocols. In a preferred embodiment, antibodies are prepared, which react immunospecifically with various epitopes of SABP2.

Polyclonal or monoclonal antibodies that immunospecifically interact with SABP2 may be utilized for identifying and purifying such proteins. For example, antibodies may be utilized for affinity separation of proteins with which they immunospecifically interact. Antibodies may also be used to immunoprecipitate proteins from a sample containing a mixture of proteins and other biological molecules.

IV. Uses of SABP2 Nucleic Acid Molecules and Proteins:

A. Nucleic Acids Encoding SABP2-related Proteins

Nucleic acids encoding SABP2 proteins may be used for a variety of purposes in accordance with the present invention. DNA, RNA, or fragments thereof encoding SABP2 proteins may be used as probes to detect the presence of and/or expression of such genes. Methods in which nucleic acids encoding SABP2 proteins may be utilized as probes for such assays include, but are not limited to: (1) in situ hybridization; (2) Southern hybridization (3) Northern hybridization; and (4) assorted amplification reactions such as polymerase chain reactions (PCR).

The nucleic acids of the invention may also be utilized as probes to identify related genes from other plant species, animals and microbes. As is well known in the art, hybridization stringencies may be adjusted to allow hybridization of nucleic acid probes with complementary sequences of varying degrees of homology. Thus, nucleic acids encoding SABP2 proteins may be used to advantage to identify and characterize other genes of varying degrees of relation to the genes of the invention thereby enabling further characterization of the molecular mechanisms controlling SA-mediated disease response in higher plants. Additionally, the nucleic acids of the invention may be used to identify genes encoding proteins that interact with SABP2 (e.g., by the "interaction trap" technique), which should further accelerate identification of the molecular components involved in the SA-mediated disease response. A new yeast two-hybrid screen (Cytotrap) available from Stratagene, which is based on the SOS-Ras signaling pathway, is complementary to the Gal4 or LexA interaction trap system which identifies protein-protein interactions in the nucleus. In contrast, the Stratagene Cytotrap system monitors interaction in the cytoplasm, hence its name. This system, which appears to have several advantages, may be the preferred screen for SABP2-interacting proteins, particularly if SABP2 is tethered to the plasma membrane via myristoylation.

Nucleic acid molecules, or fragments thereof, encoding SABP2 genes, for example, may also be utilized to control the production of SABP2 proteins, thereby regulating the amount of protein available to participate in the induction or maintenance of disease resistance in plants. As mentioned above, antisense oligonucleotides corresponding to essential processing sites in SABP2-related mRNA molecules or other gene silencing approaches may be utilized to inhibit SABP2 protein production in targeted cells. Yet another approach entails the use of double-stranded RNA mediated gene silencing. Alterations in the physiological amount of SABP2 proteins may dramatically affect the activity of other protein factors involved in the induction or maintenance of disease resistance.

The nucleic acid molecules of the invention may also be used to advantage to identify mutations in SABP2 encoding nucleic acids from plant samples. Nucleic acids may be isolated from plant samples and contacted with the sequences of the invention under conditions where hybridization occurs between sequences of sufficient complementarity. Such duplexes may then be assessed for the presence of mismatched DNA. Mismatches may be due to the presence of a point mutation, insertion or deletion of nucleotide molecules. Detection of such mismatches may be performed using methods well known to those of skill in the art.

Nucleic acids encoding the SABP2 proteins of the invention may also be introduced into host cells. In a preferred embodiment, plant cells are provided which comprise an SABP2 protein encoding nucleic acid such as SEQ ID NO: 1 or a variant thereof. Host cells contemplated for use include, but are not limited to, tobacco, *Arabidopsis*, rice, maize, wheat, tomato, potato, barley, canola, bacteria, yeast, insect and other animal cells including human cells. The nucleic acids may be operably linked to appropriate regulatory expression elements suitable for the particular host cell to be utilized. Methods for introducing nucleic acids into host cells are well known in the art. Such methods include, but are not limited to, transfection, transformation, calcium phosphate precipitation, electroporation, lipofection and biolistic methods.

The host cells described above or extracts prepared from them containing SABP2 may be used as screening tools to identify compounds which modulate SABP2 protein function. Modulation of SABP2 activity, for example, may be assessed by measuring alterations in SABP2-SA binding activities, SABP2 enzymatic activities, or SABP2 expression levels in the presence and absence of a test compound. Test compounds may also be assessed for the induction and/or suppression of expression of genes regulated by SABP2 proteins.

The availability of SABP2 protein encoding nucleic acids enables the production of plant species carrying part or all of an SABP2-related gene or mutated sequences thereof, in single or amplified copies. Transgenic plants comprising any one of the SABP2-related sequences described herein are contemplated for use in the present invention. Such plants provide an in vivo model for examining SA-mediated defense responses, and may be particularly useful in elucidating the molecular mechanisms that modulate SA-mediated defense responses. Such plants may also facilitate the identification of other endogenously expressed gene products which play a role in SA-mediated defense responses. Methods of introducing transgenes and making knockouts in plants are known to those of skill in the art.

The alterations to the SABP2-related genes envisioned herein include modifications, deletions, and substitutions. Such modifications, deletions or substitutions can result in an SABP2 having altered characteristics or functions. Alternatively, modifications and deletions can render the naturally occurring gene nonfunctional, producing a "knock out" plant. In this context, a "targeted gene" or "knock-out" is a DNA sequence introduced into the plant by way of human intervention, including but not limited to, the methods described herein. The targeted genes of the invention include DNA sequences which are designed to specifically alter SA-mediated defense responses. Substitutions of a naturally occurring gene for a gene from a second species results in a plant which produces an SABP2-related gene from the second species. Substitution of the naturally occurring gene for a gene having a mutation results in a plant with a mutated SABP2 protein. A transgenic plant carrying a SABP2 gene is generated by direct replacement of the first plant's SABP2 gene with the second SABP2 gene. These transgenic plants are valuable for use in in vivo assays for elucidation of molecular mechanisms associated with local and systemic defense response systems.

Methods of use for the transgenic plants of the invention are also provided herein. Knockout plants of the invention may be treated with agents that induce local or systemic plants defense responses. Such plants provide a biological system for assessing the protective role played by SABP2. For example, agents which modulate the action or expression of SABP2 proteins may be screened in studies using SABP2 knock out plants.

In another embodiment of the invention, transgenic plants are provided that have enhanced disease resistance. Such transgenic plants may have altered SABP2 activity due to the overexpression or underexpression of SABP2-related genes.

As described above, the SABP2-related protein-encoding nucleic acids are also used to advantage to produce large quantities of substantially pure proteins, or selected portions thereof.

B. SABP2 Proteins and Antibodies

SA is a physiologically active compound in plants, animals and microbes. SABP2 almost certainly plays a role in one or more of the physiological effects mediated by SA in plants (see Cutt and Klessig, 1992). SABP2, encoded by the nucleic acid molecules of the invention, can be used in biochemical assays for screening for novel, biologically active analogues of SA. As used herein, the term "SA analogue" is intended broadly to refer to functional analogues, instead of or in addition to structural analogues of SA, which can substitute for SA to induce SA-mediated disease defense responses in plants, or other SA-mediated responses (e.g., induction of the alternative oxidase gene or flowering, as described below).

As one example, assays for SA analogues may be based on the ability of analogues to bind SABP2 or to compete with SA for binding to SABP2. A good correlation between binding to SABP2 (measured by competition with labeled SA for binding to SABP2) and biological activity of seven SA analogues for induction of defense responses to microbial pathogens has been demonstrated, as described in U.S. Pat. No. 6,136,552. One such previously identified agent, BTH, a commercially available synthetic activator of plant defense responses that is more active than SA in inducing defense responses such as PR-1 gene expression, binds SABP2 in partially purified plant extracts about 15 fold more avidly than SA (Du and Klessig, 1997). Since SABP2 is part of the signal transduction pathway leading to disease resistance, it may be possible to enhance induction of disease resistance using analogues of SA which are not readily metabolized by the plants. It has previously been demonstrated that SA is rapidly conjugated to glucose to form SA β-glucoside (Malamy et al., 1992). This glucoside is not active for induction of disease resistance. Thus a derivative, or analogue of SA that is not readily metabolized, yet binds SABP2 and stimulates the disease resistance response, would be a superior inducer of resistance.

SABP2 likely plays a role in the numerous biological processes shown to be affected by the addition of exogenous SA, including plant disease resistance, thermogenesis, floral development, and senescence (Morris et al., 2000). Thus, these processes may be affected by altering expression levels and/or characteristics of SABP2. Current technologies of genetic engineering make both readily available. In plants, altering the level of SABP2 within the organism can be readily achieved by making transgenic plants that express SABP2 gene under a strong constitutive or inducible promoter in the sense orientation to overproduce SABP2 or in an antisense orientation or intron-spliced hairpin RNA approach to disrupt expression of endogenous SABP2 gene(s). For example, if SA and SABP2 are both involved in flower induction, then it is feasible to inhibit flowering by blocking expression of the endogenous SABP2 gene using antisense technology or by blocking function of the endogenous SABP2 by production of a dominant negative mutant form of SABP2. In addition, if SA is a signal for this (or other) process(es), but the signal is not mediated by SABP2, then overexpression of SABP2 gene could also block this process, since SABP2 may act to sequester the SA signal, given it's high affinity for SA.

Two complementary approaches can be employed to regulate SABP2 gene expression levels. The first approach involves potato virus X (PVX)- or tobacco rattle virus (TRV)-based gene silencing, pioneered by David Baulcombe's group (Ratcliff, F. et al., 1997; Ruiz, M. T. et al., 1998). The second involves construction of transgenic tobacco in which the SABP2 gene is overexpressed (sense constructs) or underexpressed (dsRNA-mediated gene silencing). Underexpression is most effectively accomplished with constructs encoding intron-spliced RNAs with a "loopless" hairpin structure (dsRNA) that then induces gene silencing (Smith et al., 2000; Wesley et al., 2001).

The PVX-based (or TRV-based) gene silencing approach, also called virus-induced gene silencing (VIGS), has several advantages. First, it is very rapid as construction of transgenic plants is not required. Second, since VIGS can be done on adult plants, it eliminates the potential problem that the silenced gene may be required for normal plant development and/or regeneration, in which case construction of the appropriate transgenic plants might not be feasible. Since VIGS is more effective in *Nicotiana benthamiana*, most of the silencing experiments are being done in this host or N.b. transgenic lines expressing the N gene of N. tabacum or Pto of tomato.

The transgenic approach is complementary to VIGS; although slow, it allows one to look at the effect of overexpression as well as underexpression. Moreover, in addition to facilitating more complete silencing of SABP2 and its potential ortholog(s), because the lines are stably transformed, they can be readily propagated and utilized for many generations in large number. Furthermore, some of the defense responses to be tested (e.g. ion fluxes, cell death) are more readily carried out in suspension culture which can be easily prepared from the transgenic plants.

In yet another embodiment of the invention, new response systems may be developed in plants, animals and microbes. Introduction of the SABP2 gene under control of an appropriate promoter should facilitate its expression in organisms or tissues in which SABP2 is not normally expressed. These organisms or tissues could then become responsive to SA that is either generated endogenously or applied exogenously. For example, it is possible to genetically engineer the synthesis of SABP2 in specific types of plant tissue (or animal tissue) by using tissue-specific promoters to drive (control) the expression of the SABP2 gene. Some of the tissues may not normally express an endogenous copy of the SABP2 gene or may express the gene at a very low level. Increasing synthesis of SABP2 in this way may affect the host tissue by making the tissue more responsive to SA, without affecting other tissues in which the engineered gene is not expressed. For example, if the amount of SABP2 is a limiting factor in a physiological process such as flower development, then an enhanced production of SABP2 in tissue or cells responsible for flower development could result in greater flower production (and subsequent seed production), without affecting other physiological processes. In another example, the gene encoding SABP2 can be introduced under appropriate control elements into an organism together with a second gene under the control of a promoter which contains a SA responsive element (SARE) that makes it inducible by SA. Such an SARE from the PR-2d and PR-1 genes has recently been characterized (Shah and Klessig, 1996; Lebel et al., 1998). The expression of this second gene should then be inducible by application of exogenously applied SA. This simple strategy should be feasible if the SA-SABP2 complex directly activates the SARE-containing promoter. However, if there are other components downstream of SABP2 in the signal transduction pathway, then their presence in the tissue or organism of interest will also be necessary for the system to work. Since SA is relatively innocuous in many systems, particularly animals, and several genes in plants (from which SAREs would be obtained) are highly induced by SA (>100×), this would be an excellent system for inducible high level expression of foreign genes in transformed cells, tissues, or organisms. There is precedence for transfer of inducible gene expression systems between very divergent organisms. For example, the GAL4 system found in yeast has been shown to function in both plants and animals (Ma et al, 1988; Kakidani and Ptashne, 1988).

In another embodiment of the invention, it may be advantageous to alter the binding properties of SABP2 through genetic engineering so that it recognizes and responds to novel SA analogues. For example, an SA-like pathway could be developed including analogues of SA and modified complementary SABP2. This system would parallel the naturally occurring SA signal transduction pathway but will be based on discrete and non-competitively binding analogues. In this way, the normal SA-based cellular functions of a plant will continue undisturbed. However, an increase in newly introduced functions may be induced. The engineered plant, containing the modified complementary SABP2 and other downstream mechanisms necessary for SA-induced expression, may be activated by the application of the non-competitive SA analogue. In this embodiment, plant functions would be influenced by two discrete signal transduction systems.

The following examples are provided to illustrate particular embodiments of the invention. They are not intended to limit the scope of the invention in any way.

EXAMPLE I

Purification and Cloning of SABP2-Encoding Nucleic Acid Molecules

In order to elucidate the molecular mechanism(s) that modulate SA-mediated defense responses in plants, identify novel defense-inducing molecules and construct transgenic plants with enhanced disease/stress resistance, proteins associated with SA binding activity were identified. One such protein, SABP2, has been purified and cloned as described hereinbelow.

I. Materials and Methods:

The following protocols are provided to facilitate the practice of the present invention.

Leaf extraction: Tobacco (*Nicotiana tabacum* cv Xanthi nc [NN]) plants were grown in a greenhouse at 22° C. during a 16 hour light period. 7.5 kg of fully expanded leaves from 7–8 week old plants were harvested, de-ribbed, weighed and rapidly frozen in liquid nitrogen. The tissue was stored at −80° C. until further use. [All subsequent steps were carried out at 4° C. unless specified otherwise.] The frozen leaves (in batches of 1.5 kg each) were ground into a fine powder using a pestle mortar and homogenized in a mixer grinder with 3 vol(w/v) of Buffer A (20 mM sodium citrate, 5 mM MgSO$_4$, 1 mM EDTA, pH 6.3, 14 mM β-mercaptoethanol supplemented with 0.1 mM phenylmethylsulfonylflouride (PMSF), 1 mM benzamidine-HCl and 1.5% (w/w) polyvinylpolypyrrolidone (PVPP). The homogenate was filtered through 2 layers of muslin cloth and 2 layers of miracloth (Calbiochem). The filtrate was centrifuged at 11,000 g in a GS-3 rotor (Sorvall) for 30 minutes, and the supernatant was collected and used for further purification.

[$^3$H] Salicylic acid-binding assay: The protein extracts/fractions were mixed with 0.1 µM [$^3$H]-SA (23.6 Ci/mmol) (custom synthesized by NEN Life Science Products) in Buffer A to bring the total volume of the reaction mixture to 150 µl. The extracts were then incubated on ice for 60 minutes. Spin columns were prepared by packing Sephadex G-25 fine (Pharmacia) equilibrated with Buffer A into 1 ml disposable syringe barrels. The G-25 was packed to 1 ml and equilibrated by centrifuging at 1000 g for 4 minutes in a H-1000B rotor (Sorvall) at 4° C. The entire binding mixture was loaded onto the column and centrifuged under similar conditions. Bound [$^3$H]-SA which is present in the flow through, was mixed with 4 ml scintillation cocktail (Ecolite, ICN) and measured in a liquid scintillation counter. Appropriate controls were also assayed. Since it was found that the chloride interferes with SA binding, care was taken to avoid its use in any form in the purification process.

Protein Determination: Identification of protein in the fractions was determined using Bradford reagent (BioRad). BSA was used as standard protein.

Ammonium Sulfate Fractionation: Powdered ammonium sulfate [(NH$_4$)$_2$SO$_4$] was slowly added to a final concentration of 50% saturation to a continuously stirring sample of leaf extract supernatant. The slurry was incubated for an additional 30 minutes after the final addition of (NH$_4$)$_2$SO$_4$ followed by centrifugation at 11,000 g in a GS-3 rotor (Sorvall) for 40 minutes at 4° C. The supernatant was brought to 75% saturation by slowly adding additional (NH$_4$)$_2$SO$_4$. After complete dissolution of the (NH$_4$)$_2$SO$_4$, the slurry was incubated for additional 30 minutes followed by centrifugation at 11,000 g for 30 minutes. The pellet was resuspended in a minimum volume of Buffer A and retained for further purification.

Sephadex G-100 Chromatography: Sephadex G-100 was equilibrated in Buffer A and packed into a 500 ml (C26/100, Pharmacia) column. The resuspended $(NH_4)_2SO_4$ pellet was loaded on to this Sephadex G-100 column and eluted overnight in Buffer A. Fractions of 7 ml were collected and assayed for SA-binding activity. The fractions with high [$^3$H]-SA binding activity were pooled together and precipitated with 75% $(NH_4)_2SO_4$ saturation. Further chromatographic steps were carried out using Fast Protein Liquid Chromatography system (FPLC, Pharmacia).

Q Sepharose anion exchange chromatography: The Sephadex G-100 purified $(NH_4)_2SO_4$ pellet from two, 1.5 kg preparations were resuspended in Buffer B (10 mM Bicine, pH 8.5, 14 mM β-mercaptoethanol, 0.1 mM PMSF, and 1 mM benzamidine-HCl) and desalted on a desalting column (HiPrep, 26/10, Pharmacia) equilibrated in Buffer B. The desalted protein preparation was loaded at flow rate of 1 ml/min on to a 25 ml Q Sepharose Fast Flow column (XK16/20, Pharmacia) pre-equilibrated with Buffer B. The loaded column was washed with 400 ml of 15 mM $(NH_4)_2SO_4$ in Buffer B. The bound proteins were eluted at a flow rate of 0.5 ml/min with a 125 ml×125 ml linear gradient of 15–180 mM $(NH_4)_2SO_4$ in Buffer B. Fractions of 4 ml were collected and only the fractions with high [$^3$H]-SA binding activity were pooled. Solid $(NH_4)_2SO_4$ was slowly added to a concentration of 1 M to the pooled fractions for further purification by Butyl Sepharose chromatography.

Butyl Sepharose: The total pooled protein fractions (from 7.5 kg) from Q Sepharose chromatography containing 1 $M(NH_4)_2SO_4$ was applied at a flow rate of 0.5 ml/min to a 15 ml Butyl Sepharose 4 Fast Flow column (XK16/20, Pharmacia) pre-equilibrated with 1.2 M $(NH_4)_2SO_4$ in Buffer B. After washing with 150 ml of 1 M $(NH_4)_2SO_4$ in Buffer B, the bound proteins were fractionated with a 75 ml×75 ml linear gradient of decreasing $(NH_4)_2SO_4$ (1 to 0 M) in Buffer B. The 4 ml fractions were collected and assayed for [$^3$H]-SA binding. The fractions with high binding activity were pooled and precipitated with 75% $(NH_4)_2SO_4$ saturation. The pellet was resuspended in Buffer B and desalted on a desalting column (HiPrep, 26×10, Pharmacia).

Mono Q anion exchange: The desalted protein preparations from Butyl Sepharose were applied to a Mono Q HR column (5/5, Pharmacia) at a flow rate of 0.25 ml/min. After washing with 20 ml of 15 mM $(NH_4)_2SO_4$ in Buffer B, the bound proteins were eluted with a 10 ml×10 ml linear gradient of 15–180 mM $(NH_4)_2SO_4$ in Buffer B at a flow rate of 0.25 ml/min. Fractions of 0.5 ml were collected and fractions containing high [$^3$H]-SA binding were pooled. The protein solution was precipitated with 75% $(NH_4)_2SO_4$ saturation and desalted using a HiTrap desalting column (5 ml, Pharmacia) equilibrated with Buffer C (Buffer B+150 mM $[NH_4]_2SO_4$).

Superdex-75: The desalted protein preparation from the previous mono Q purification step was loaded at a flow rate of 0.25 ml/min on to a Superdex 75 column (HR 10/30, Pharmacia), pre-equilibrated with Buffer C. The column was eluted with 25 ml Buffer C. Fractions of 0.25 ml were collected and the fractions containing high [$^3$H]-SA binding activity were pooled. The pooled fractions were precipitated with 75% $(NH_4)_2SO_4$ and desalted using a HiTrap desalting column (5 ml, Pharmacia) in Buffer B.

Mono Q anion exchange: The desalted protein preparations from the Superdex 75 purification step were applied to a second mono Q column. After washing with 20 ml of 15 mM $(NH_4)_2SO_4$ in Buffer B, the bound proteins were eluted with a 10 ml×10 ml linear gradient of 15–180 mM $(NH_4)_2SO_4$ in Buffer B. Fractions of 0.5 ml were collected and assayed for [$^3$H]-SA binding activity.

Preparative Polyacrylamide Gel Electrophoresis: The fractions with high binding activity were desalted individually with NAP-5 columns (Pharmacia) pre-equilibrated with 5 mM Bicine, pH 8.5. The samples were concentrated by speed-vac, and then electrophoresed on a 12.5% SDS-polyacrylamide gel (16 cm×20 cm, BioRad) as described by Laemmli (1970). After staining with 0.1% coomassie blue R-250 and destaining, the protein bands which co-purified with SA-binding activity, were cut out and sequenced at the Cornell University Protein Sequencing Facility.

Protein Sequencing: The protein samples were subjected to in-gel digestion with trypsin, and the tryptic fragments were eluted and subjected to matrix-assisted laser desorption ionization (MALDI) mass spectrometry or further purification by reverse phase HPLC. Several HPLC peaks were subjected to sequencing by Edman degradation.

Estimation of Apparent Molecular Mass: The apparent molecular mass of the native SABP2 protein was estimated by means of gel-filtration chromatography on a Superdex 75 column. The purified SABP2 (0.2 ml) from a mono Q column was loaded onto the Superdex 75 column at a flow rate of 0.25 ml/min and eluted at the same flow rate with Buffer C. The column was calibrated with the following standards: ovalbumin (43 kDa), chymotrypsinogen A (25 kDa) and ribonuclease A (13.7 kDa) (Pharmacia).

Cloning: Based on the amino acid sequence from the SABP2 protein, several degenerate oligonucleotides, both in forward and reverse directions were custom synthesized (Invitrogen) using the preferred codon usage for tobacco. Total RNA was isolated from the young tobacco leaves using Trizol (Invitrogen) following the manufacturer's instructions. The total RNA was treated with RNase-free DNase (Promega) to remove any contaminating genomic DNA. This purified sample of RNA was used to reverse transcribe cDNA using Superscript II Reverse Transcriptase (Invitrogen) and universal oligo-dT$_{(14)}$ with an adapter sequence.

A combination of degenerate primers (5'-ACWCART-TYTTRCCHTAYGG-3' (SEQ ID NO: 7; where W is A or T; R is A or G; Y is C or T; and H is A, C or T) encoding the sequence TQFLPYG (SEQ ID NO: 8) of peptides pk32, 34 and 36 and universal adapter primer (5'-GACTCGAGTC-GACATCGA-3'; SEQ ID NO: 9) were used to PCR amplify part of the SABP2 cDNA. A small fraction of the PCR amplification products were used as a template for a second round of PCR amplification using the same set of primers. The amplified products were fractionated on a 1.5% agarose gel using 1×TAE buffer. The DNA bands were visualized by ethidium bromide staining. The amplified DNA bands were excised out of the gel and the DNA was purified using a gel extraction kit (Qiagen). The purified DNA was then ligated into a PCR cloning vector pGEMT (Promega). DNA was prepared from the clones containing the inserts. The purified DNA was sequenced by cycle sequencing using the BigDye Terminator and analyzed on a Perkin Elmer Automatic DNA sequencer.

To isolate the 5' half of the SABP2 gene, 5' RACE ready cDNA was prepared from the total RNA isolated from tobacco leaves using the SMART RACE cDNA amplification kit (Clontech). PCR amplification was first performed with the SABP2 specific primer, E-6 (5'-AGAGATCAGT-TGTATTTATG-3'; SEQ ID NO: 10) and the Universal Primer Mix (Clontech) using the 5' RACE ready cDNA as template. A second PCR amplification was performed using the E-6 primer and the Nested Universal Primer (NUP, Clontech). The amplified products were analyzed on a 1.2% agarose gel and purified as described earlier. The fragments were then cloned into pGEMT vectors and sequenced. All PCR amplifications were carried out using the Advantage 2 PCR kit (Clontech) following manufacturer's instructions.

Expression of Recombinant SABP2 in E. coli. Full-length tobacco SABP2 was PCR amplified to introduce BamH1 enzyme sites at both ends using the primers F2 (CGCG-GATCCATGAAGGAAGGAAAACACTTTG) (SEQ ID NO:51) and F3 (GCGGGATCCAGATCAGTTGTATT-TATGGC) (SEQ ID NO:52). The amplified product was cloned into the BamH1 site of pET28a (Novagen) and sequenced. Recombinant SABP2 (rSABP2) was synthesized as a soluble protein in E. coli strain BL21 (DE3) and affinity purified by Ni-NTA agarose chromatography (Novagen) as described by the manufacturer. rSABP2 was further purified on a Mono Q column as described earlier.

Figure 1:
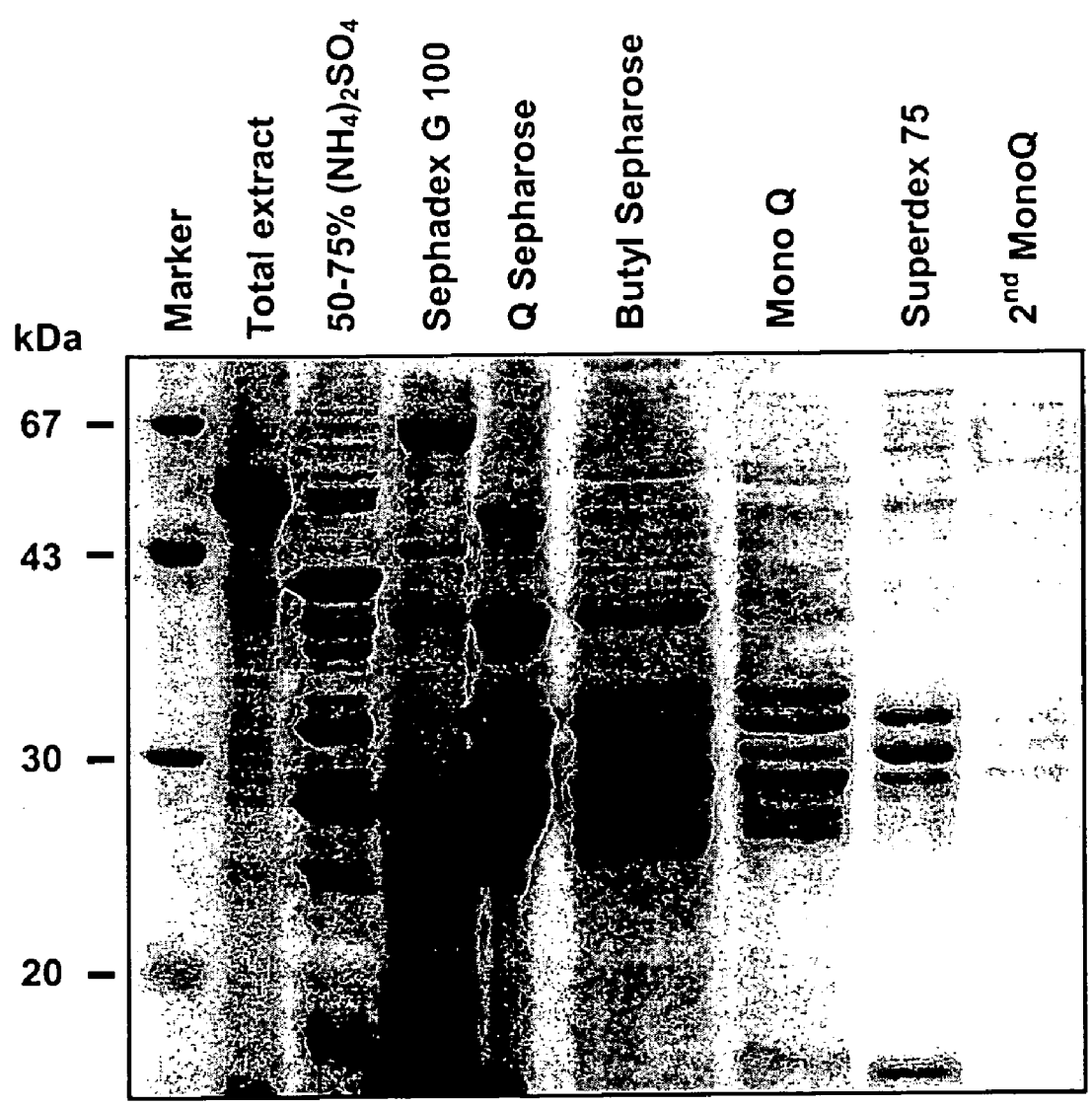
FIG. 1 shows the resolution of the protein composition from pooled protein fractions containing the highest levels of SA-binding activity from each step in the purification of SABP2 on a 12.5% SDS-polyacrylamide gel. The right lane shows the resolution of an aliquot of fraction #16 of the second Mono Q column which contained the highest amount of SA-binding activity. The molecular size markers are in the left-most lane.

II. Results:

A. SABP2 Purification:

The initial attempts to purify SABP2 from tobacco leaves indicated that it is present in very low amounts. Therefore, a large amount of tissue was used as the starting material for isolation of sufficient amounts of purified SABP2 for amino acid sequencing. The soluble proteins from 7.5 kg of tobacco leaves were fractionated with ammonium sulfate, and the 50–75% saturation $(NH_4)_2SO4$ fractions were further purified using the following purification scheme involving Sephadex G-100 gel filtration (desalting and size fractionation), Q Sepharose (anion exchanger), Butyl Sepharose (hydrophobic interaction), mono Q (strong anion exchanger), Superdex 75 (size fractionation) and a second mono Q. This scheme lead to an approximately 24,000 fold purification of SA-binding activity (Table II). Analysis of the pooled fractions containing the SA-binding activity from the various chromatographic steps by SDS-PAGE shows the purification of SABP2 (FIG. 1).

TABLE II

PURIFICATION OF SABP2 FROM TOBACCO LEAVES

| Fractionation steps | Total activity (dpm) | Percent (%) | Total protein (mg) | Specific activity (dpm mg$^{-1}$) | Purification (fold) |
|---|---|---|---|---|---|
| Crude | 7509343 | 100 | 31626.2 | 237 | 1.0 |
| 50–75% | 1892720 | 25 | 4723.25 | 400 | 1.7 |
| Sephadex G- | 1385625 | 18.4 | 2216.82 | 625 | 2.6 |
| Q Sepharose | 1023300 | 13.6 | 56.925 | 17976 | 75.8 |
| Butyl | 123840 | 1.6 | 4.398 | 28158 | 118.8 |
| Mono Q | 1386700 | 18.4 | 0.368 | 3762930 | 15877.3 |
| Superdex 75 | 55460 | 0.7 | 0.013 | 4160420 | 17554.5 |
| Mono Q | 45515 | 0.6 | 0.008 | 5689375 | 24005.8 |

The presence of SA-binding proteins was monitored using a very efficient [$^3$H]-SA binding assay. Extraction of the leaf proteins at low pH (6.3) helped in precipitating out many proteins, while the SABP2 remained soluble. Most of the non-specific SA-binding activity was removed in the 0–50% $(NH_4)_2SO_4$ fractions, and the 50–75% fraction contained most of the specific SA-binding activity (as determined by competition with unlabeled SA). Most of the high molecular weight SA-binding activity co-purifying with the carbonic anhydrase activity (e.g., SABP3, Slaymaker et al. 2002) was in the early fractions collected from the Sephadex G-100 column. The later fractions, which contained SABP2 but did not contain any detectable carbonic anhydrase activity, were pooled and retained for further purification.

Washing of the Q Sepharose column with 400 ml of Buffer B containing 15 mM $(NH_4)_2SO_4$ removed protein lacking SA-binding activity. The presence of high concentrations of $(NH_4)_2SO_4$ in the protein fractions did not interfere with the [$^3$H]-SA binding assay.

Figure 2:
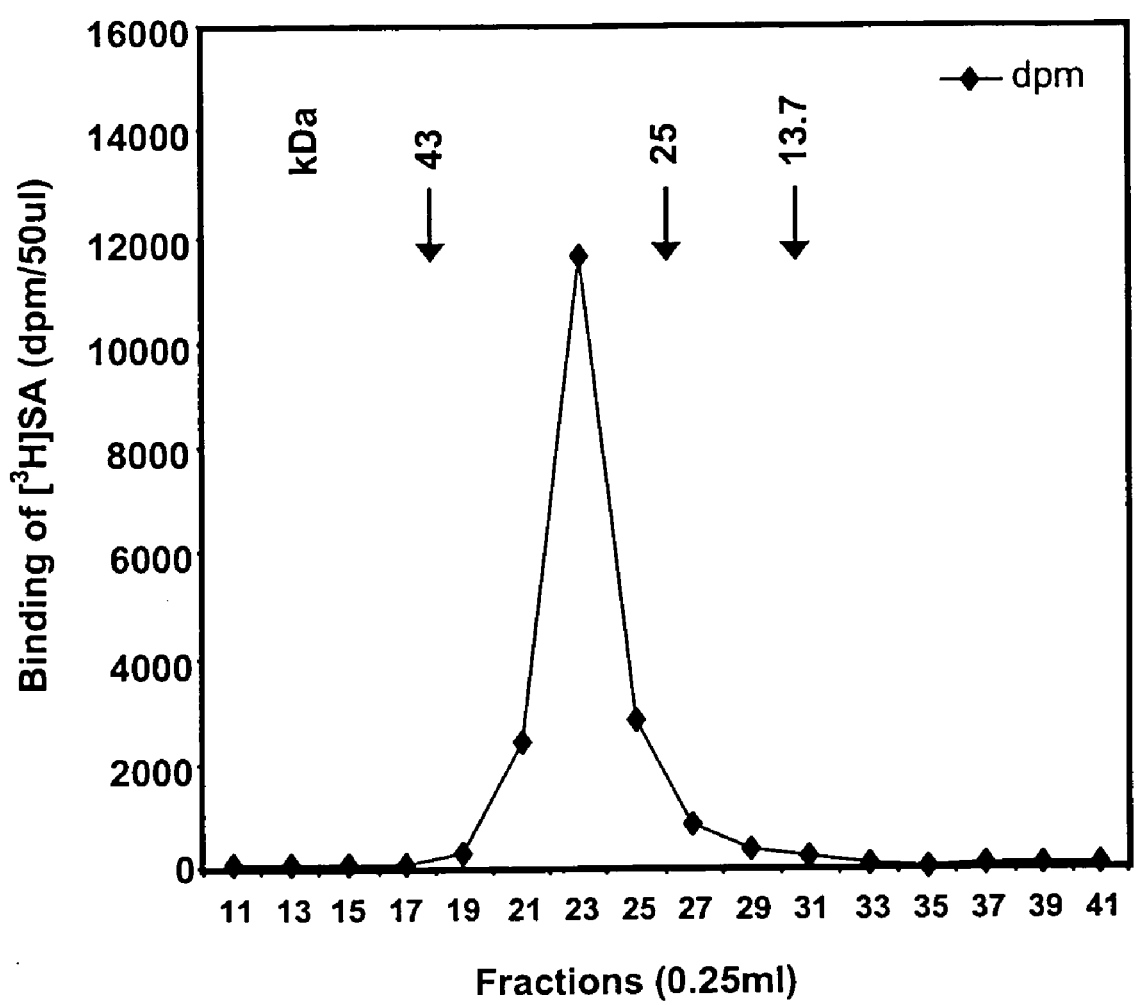
FIG. 2 shows a graph depicting the elution profile of SA-binding activity from the Superdex G75 HR 10/30 gel filtration FPLC column. The position of the molecular mass markers in kiloDaltons are indicated by the arrows. The SA-binding activity of each fraction was determined using [$^3$H-SA].
Figure 3:
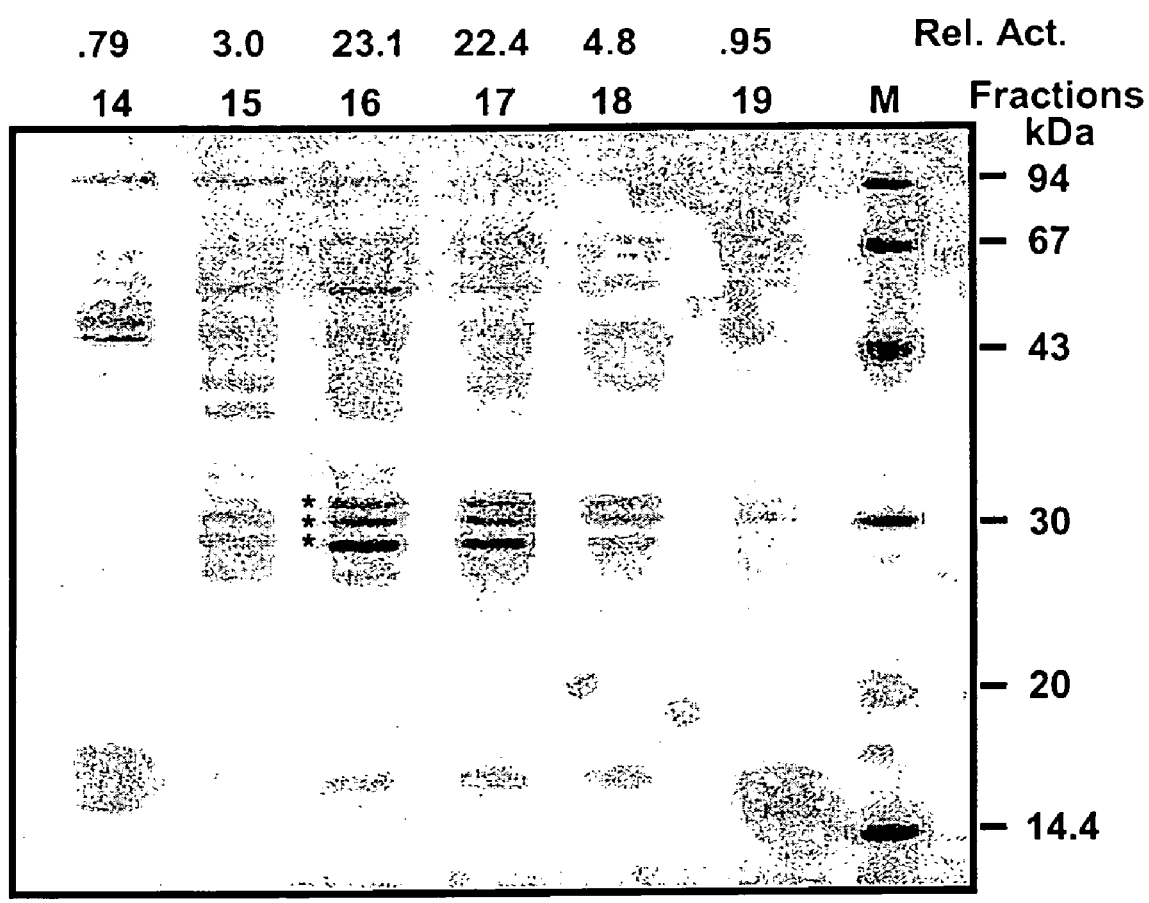
FIG. 3 shows the resolution of three proteins (28–32 kDa) on a 12.5% SDS-polyacrylamide gel that co-purify with SA-binding activity. The molecular size markers are in lane M. Lanes 14–19 are fractions eluted from the second mono Q column. The relative SA-binding activity is given in arbitrary units above each fraction.

Analysis of the SDS-polyacrylamide gel electrophoresis of the fractions from the second mono Q column indicated that three proteins (28, 30 and 32 kDa) co-purified with [$^3$H]-SA binding activity (FIG. 3). The amount of the 28 kDa protein most closely tracked with level of SA binding activity, which strongly suggested that this protein was SABP2. The native molecular mass of the SABP2 was estimated to be ~28 to 30 kDa by chromatography on the Superdex 75 column (FIG. 2). This estimate was in good agreement with the ~28 kDa weight estimated by SDS-PAGE. These results indicated that SABP2 is a monomeric protein. The sequences from the three proteins (28, 30 and 32 kDa) were determined and are provided in Table III, sequence identification numbers 11–27 are shown in parentheses.

TABLE III

Amino Acid Sequences From 28, 30 and 32 kDa Proteins

| Peptide | Peptide Designation | Peak# | Sequence |
|---|---|---|---|
| 28 kDa | Peptide #1 | pk22a | VTALDLAASGTDLR (11) |
| " | " | pk23 | XTALDLAASGTD (12) |
| " | " | pk55 | VXALDLAASGIDLR (13) |
| " | Peptide #2 | pk36 | TPAENW/ILDTQFLPYG (14) |
| " | " | pk34 | TPAENTLDTQF/ELM/PYG (15) |
| " | " | pk32 | XPAENWLDTQFLPY (16) |
| " | Peptide #3 | pk29 | YPEe/nPL/gTS/tMF (17) |
| " | Peptide #4 | pk22b | hYALFMEDLHK (18) |
| " | Peptide #5 | pk30 | AQ/KYFTDER (19) |
| " | " | pkx | YFQDER (20) |
| 30 kDa | Peptide #1 | pk16a | LVPVDVSIDP (21) |
| " | Peptide #2 | pk16b | i/yhfyiyplns (22) |
| " | Peptide #3 | pk17 | F/s/aLYDFVD/fG/fHK (23) |
| " | Peptide #4 | pk25a | YVTPENNLYF (24) |
| " | Peptide #5 | pk25b | i/sdyhis/qf/ieel (25) |
| 32 kDa | Peptide #1 | pk11 | NSIQPDFYANK (26) |
| " | Peptide #2 | pk26 | DIDGVPETLDLR (27) |

* Sequences obtained from SABP2 purified and sequenced using a different purification scheme
"x" means any amino acid.
"/" means the amino acid at that position is either the amino acid shown before or after the '/'
Amino acids in lower case means that data was only clear enough to make a tentative assignment.

The 28 kDa protein is SABP2 because (1) it most closely co-purified with the SA-binding and (2) in an earlier purification scheme the 28 kDa protein co-purified with SA binding activity, while the presence of the 30 kDa and 32 kDa proteins were not evident in those fractions. In addition, partial amino acid sequence analysis of tryptic peptides of the 28 kDa protein obtained in the earlier purification scheme indicated that it is the same 28 kDa protein obtained by the purification scheme described above. Further, expression of the cloned cDNA in E. coli produces a protein of the correct molecular weight and very high SA specific binding activity, with correct specificity for SA analogs (see Table IV).

B. Features of the SABP2 cDNA Clone:

PCR amplification was performed using a degenerate primer (5'-ACWCARTTYTTRCCHTAYGG-3'; where W is A or T; R is A or G; Y is C or T; and H is A, C or T; SEQ ID NO: 7) encoding the sequence TQFLPYG (SEQ ID NO: 8) of peptides pk32, 34 and 36 and universal adapter primer (5'-GACTCGAGTCGACATCGA-3'; SEQ ID NO: 9). The template used for PCR was the cDNA reverse transcribed from total RNA isolated from tobacco leaves. Agarose gel analysis of the PCR products did not result in any discrete bands. Thus, a second round of PCR amplification was performed using a small fraction of the PCR amplification product as the template with the same set of primers. This resulted in amplification of a ~650 bp fragment which was gel purified and cloned into a pGEMT cloning vector. The clone, sequenced using plasmid specific primers, was 639 bp long with a complete 3' UTR and a polyA tail.

Analysis of the deduced amino acid sequence indicated that the clone encoded four of the five peptides (peptides #2–#5 of the 28 kDa protein in Table III) identified by partial amino acid sequence determination of SABP2. For several of these peptides, the match to the deduced amino acid sequence is close, but not exact. This may be due to sequencing errors or may indicate that SABP2 is encoded by a gene family with the difference between peptide sequence and deduced amino acid sequence resulting from them coming from different family members.

large open reading frame that encodes a 260 amino acid protein with a calculated molecular mass of 29.3 kDa and an estimated pI of 5.45.

The sequences corresponding to all five peptides obtained from the sequencing of the tryptic fragments of the purified SABP2 protein are underlined in the deduced amino acid sequence presented in FIG. 4. This result indicates that the clone corresponds to the purified SABP2 protein. The alignment of the deduced amino acid sequence of the open reading frame along with the homologous proteins (FIG. 5) indicates that the clone encompasses the full length SABP2 cDNA.

C. Proof That the 28 KDa Protein is SABP2

To rigorously establish that the 28 KDa protein from plant extract was SABP2, the cloned cDNA was expressed in *E. coli* as His$_6$-tagged fusion protein and the recombinant protein was purified on a Ni column and tested for SA-binding activity (Table IV). The recombinant protein exhibited very high $^3$H-SA binding activity, and this binding was inhibited effectively by addition of a large molar excess of unlabeled SA or it's biologically active (for induction of PR genes or enhanced disease resistance) analogs but not it's inactive analogs (e.g. 4-HBA).

TABLE IV

TOBACCO SABP2 AND TWO *ARABIDOPSIS* HOMOLOGS PRODUCED IN *E. COLI* HAVE SA-BINDING ACTIVITY WHICH IS SPECIFIC FOR SA AND ITS BIOLOGICALLY ACTIVE ANALOGS

| ASSAY | Bound [$^3$H] SA SABP2 | Bound [$^3$H] SA AtSB2L9* | Bound [$^3$H] SA AtSB2L5* | Bound [$^3$H] SA AtSB2L1* | Biological Activity of competitor |
|---|---|---|---|---|---|
| No competitor | 140206** | 16486 | 12927 | 70 | — |
| 1 mM unlabeled SA | 160 | 36 | 121 | 42 | active |
| 1 mM unlabeled 5-CSA | 260 | 42 | 64 | 38 | active |
| 1 mM unlabeled 2, 6-DHBA | 924 | 1072 | 1742 | 36 | active |
| 1 mM unlabeled 4-HBA | 95634 | 3620 | 4757 | 65 | inactive |

*AtSB2L1 is Genbank Accession NM_127926 (SEQ ID NO: 32); AtSB2L5 is Genbank Accession NM_121068 (SEQ ID NO: 36); AtSB2L9 is Genbank Accession NM_119878 (SEQ ID NO: 40).
**Radioactivity is measured in dpm.

The DNA sequence did not show significant homology to any known sequence in the NCBI database. However, the corresponding protein exhibited significant homology to several known plant proteins (FIG. 5). This comparison also suggested that the cDNA clone corresponds to the C-terminal half (127 residues) of a 28–30 kDa protein.

In order to isolate the missing 5' half of the SABP2 gene, 5' RACE was carried out using tobacco cDNA as the template. The first round of 5' RACE resulted in the amplification of a very faint DNA band identified by agarose gel analysis. PCR amplification was then repeated using the E-6 (5'-AGAGATCAGTTGTATTTATG-3'; SEQ ID NO: 10) primer, a Nested Universal Primer (Clontech) and a small fraction of the first PCR product as the template. This second round of PCR amplification yielded a ~850 bp fragment which was further cloned and sequenced.

Analysis of the sequence confirmed that the amplified product from 5'RACE contained the missing 5'portion of the SABP2 gene as well as the portion of the gene 5' to the E-6 primer that was present in the original 3' end clone. Further analysis of the 5' RACE product, together with the original 3' end clone of the SABP2 gene, revealed that the SABP2 mRNA is at least 1079 nucleotides in length and contains a III. Discussion:

SABP2 is a member of the super family of alpha/beta fold hydrolases. This gene has not previously been identified in tobacco. However, *Arabidopsis*, which has SABP2-like activity (Du and Klessig, 1997), contains a large gene family with 18 full-length members that encode proteins with 32%–57% identity and 46–71% similarity to the tobacco SABP2. They are referred to as A.t.SABP2 like (AtSB2L) with AtSB2L1 having the highest percentage identity over the entire 260 a.a. of tobacco SABP2 and AtSB2L18 the lowest. See Example IV. This *Arabidopsis* family of hypothetical/putative proteins shows high homology to alpha-hydroxynitrile lyases/(S)-acetone-cyanohydrin lyases (hnl or acl) isolated from cassava *Manihot esculenta* and rubber plants (*Hevea brasilienses*)(FIG. 5). This enzyme, together with a β-glycosidase, releases hydrogen cyanide (HCN) through a process termed cyanogenesis, from cyanogenic glycosides (Hickel et al., 1996). HCN acts as a repellent to herbivores including insects (Kakes, 1990; Poulton, 1990). HCN may also play a role in resistance to pathogens (Hickel et al., 1996; Murphy et al., 1999).

Chivasa and Carr (1998) have also shown that KCN induces resistance to tobacco mosaic virus (TMV) in tobacco. Potassium cyanide (KCN) also induces expression of an alternative oxidase, which Carr and coworkers suggest plays a role in resistance to viruses (movement and/or replication) such as TMV, but not to bacterial or fungal pathogens (Chivasa et al., 1997; Murphy et al., 1999).

In contrast to some plants, which release large quantities of HCN from their cyanogenic glycoside reserves upon predation (Conn, 1981), most plants, including *Arabidopsis* contain little or no cyanogenic glycosides (Wäspi, et al., 1998). Perhaps in these low or non-cyanogenic plant species, SABP2/AtSB2Ls releases small quantities of HCN from previously undetected small reserves, which are sufficient to activate a very local response(s), perhaps through induction of an alternative oxidase.

Alternatively, SABP2 may not possess hnl activity, but may have another function. Rice, for example, which lacks readily detectable levels of cyanogenic glycosides (Wäspi, et al., 1998), contains a gene termed Pir7b whose expression is induced following infection with the avirulent *Pseudomonas syringae* pv. syringae. Infection with avirulent P. s. s. also induces acquired resistance to the rice blast fungus, *Pyricularia oryzae* (Smith and Métraux, 1991). Pir7b is homologous (35% identity, 56% similarity) to the cassava and rubber plant hnl (and to SABP2; 42% identity, 61% similarity), but has no hnl activity. Rather it exhibits esterase activity towards naphthol AS-esters (Wäspi, et al., 1998).

Figure 6A:
FIGS. 6A and 6B show that SABP2 has lipase activity which is stimulated by salicylic acid.

Interestingly, Pir7b contains a conserved catalytic triad of serine, aspartate and histidine and a lipase signature sequence (Wäspi, et al., 1998). The N-terminal regions of lipase/esterases, like Pir7b, contain the serine residue of the catalytic triad and the lipase signature sequence while its aspartate and histidine reside in the C-terminal half. The serine, aspartate and histidine residues of the triad are also present and appropriately positioned within SABP2. SABP2 also contains the lipase signature sequence. This protein appears to have a functional esterase/lipase, based on its ability to release MUF (4-Methyl umbelliferone) from MUF butyrate (FIG. 6). There is considerable evidence for the involvement of lipids and lipases in cellular signaling. For example, diacylglycerol activates protein kinase C which then modulates many $Ca^{2+}$-dependent cellular processes (Niskizuka, 1986).

Moreover, two additional *Arabidopsis* genes encoding lipase-like proteins, EDS1 and PAD4, when mutated, result in increased susceptibility to pathogens. The products of both genes are thought to function upstream of SA (Falk et. al., 1999; Zhou et. al., 1998) and may form part of a signal-amplification loop with SA (Jirage et. al., 1999). However, lipase activity has not yet been demonstrated for either protein (Falk et. al., 1999; Jirage et. al., 1999). SABP2 also has strong homology to several esterases such as the ethylene-induced esterase from *Citrus sinensis* (58% identity and 72% homology, Zhong et al., 2001) and polyneurideine aldehyde esterase from *Rauvolfia serpentina* (57% identity and 75% homology) (Dogru et al., 2000).

In addition to SABP2's activity on MUF butyrate, sequence comparisons and structural analyses suggest that this protein is a lipase. Supporting this hypothesis SABP2's N-terminal sequence contains a domain (a.a. 15–127) present in mammalian lecithin (phosphatidylcholine) cholesterol acyltransferase (LCATs) and similar proteins found in mammals, yeast, *C. elegans* and *Arabidopsis*. In mammals, LCAT, which has a role in cholesterol transport and metabolism, converts phosphatidylcholine and cholesterol to lysophosphatidylcholine and cholesteryl esters in a sequential reaction on the surface of high density lipoproteins (Jones, A., 2000). LCAT can also use additional acyl donors besides phosphatidylcholine, such as phosphatidylethanolamine, and other acyl acceptors in addition to cholesterol including water. Thus, based on its homology to LCAT and other alpha/beta fold hydrolases, SABP2 may be a phospholipase involved in lipid metabolism and signaling in plants.

Taken together, these sequence analyses strongly implicate SABP2 as a critical signaling component in SA-mediated disease resistance, perhaps by acting as an esterase/lipase.

EXAMPLE II

Analysis of Sabp2 Gene Copy Number, Expression Patterns and Enzymatic Activity

Determination of SABP2 distribution and expression patterns provides valuable insight into the mechanisms and nature of plant pathogen resistance. Accordingly, experiments were performed to assess the effects of altering SABP2 expression levels on pathogen resistance.

The following materials and methods are provided to facilitate the practice of Example II. Distribution and copy number can be determined by Southern analysis and expression of SABP2 can be determined by Northern analysis, according to the methods of Sambrook et al., 1989.

SABP2 Gene Expression, Distribution, and Copy Number

Southern hybridization can be utilized to determine the distribution and copy number of SABP2 in different plant species. Homologs in humans, mouse, *Drosophila* and *S. cerevisiae* may also be identified using sequence information in the cDNA clone set forth herein. Database analysis already indicates that homologs are present in a diverse group of plants including *Arabidopsis*, rice, cassava and rubber tree. The cassava and rubber tree proteins are ACLs that may play a role in cyanogenesis while the rice protein, termed PIR7b, does not have lyase activity but is an esterase. As mentioned previously, expression of Pir7b is induced, in parallel with acquired resistance to the rice blast fungus *Pyricularia oryzae*, by infection with avirulent P.s. pv syringae (Waspi, U. et al., 1998).

Southern blot analysis done at both low and high stringency identified only 2–4 bands with restriction enzymes that do not have recognition sequences in the SABP2 coding region. Since tobacco is amphidiploid, this result suggests that SABP2 is encoded by a single gene (but two alleles) or by a very small gene family. Slight variation in the deduced a.a. sequence of the cloned SABP2 from the a.a. sequence obtained from the purified protein for three of the five tryptic peptides also suggests the presence of at least two genes or alleles of a single gene. In contrast, *Arabidopsis* contains 18 AtSBP2Ls, most of which are expressed and two have been shown to have SA-binding activity (Table IV).

Expression studies have been initiated and already indicate that the tobacco SABP2 and one of its putative *Arabidopsis* ortholog, AtSB2L9, are induced in plants resisting infection by viral [tobacco mosaic virus(TMV) or turnip crinkle virus (TCV)] or bacterial (P. s.) pathogens. See FIG. 7. These studies can be extended to other plant-pathogen interactions, e.g. P. s. pv tabaci, and P.s. pv tomato with or without AvrPto in tomato or Pto-transformed *Nicotiana benthamiana*, for SABP2 and P. s. and *Peronospora parasitica* for AtSB2L5, AtSB2L9, and other putative orthologs in *Arabidopsis*. While TMV induction of SABP2 expression is SA dependent, SA (or BTH) treatment alone is insufficient for this induction, suggesting the involvement of another factor. A likely candidate is ethylene since its synthesis is induced by TMV (de Laat, A. M. M. et al., 1982) and ethylene has recently been shown to induce an esterase in citrus which is highly homologous to SABP2 and the AtSB2Ls (Zhong, G. Y. et al., 2001). Therefore, induction of SABP2 and its *Arabidopsis* ortholog(s) by ethylene can be tested in a similar fashion.

A general picture of the temporal and spatial expression of the two (or more) tobacco SABP2 genes/alleles is obtained by cloning the second gene/allele and designing member/allele-specific probes (usually corresponding to the divergent 3'UTR). In situ hybridization can then be used to determine a more refined expression pattern.

Localization

A better understanding of SABP2's function is facilitated by determining its subcellular location. Subcellular location can be determined by immunofluorescence microscopy, which has been used extensively, for example, to determine the subcellular locations of other proteins, including the adenovirus DBP (Voelkerding, K. V. et al., 1986) and tobacco PR-1 proteins (Carr, J. P. et al., 1989; Dixon, D. C. et al., 1991). An alternative and complementary approach is subcellular fractionation followed by western analysis using anti-SABP2 antibodies. Subcellular fractionation techniques used to identify SABP3 (Slaymaker, D. H., et al., 2002) and SABP4 and characterize NO-sensitive aconitases (Navarre, R., et al., 2000), can be readily modified for western analysis of SABP2. High affinity antibodies (Ab) have been prepared in rabbits to native and SDS-denatured SABP2. The strongest Ab is to the native SABP2 and is highly specific, reacting only with SABP2 in western analysis of total protein extracts from mock- or TMV-infected tobacco (see FIG. 7B). Thus, this Ab is very suitable for immunofluorescence microscopy.

Initial localization is done in TMV-infected plants or in a transgenic line overexpressing SABP2. Alternatively, analysis may be conducted of plants overexpressing SABP2 tagged at its C-terminus with the HA epitope, for which highly specific, high affinity Ab are commercially available. Others have used a similar approach to localize bacterial avr factors/effectors to the plant plasma membrane (PM) (Nimchuk, Z. et al., 2000; Shan, L., et al., 2000). Interestingly, SABP2 possesses a myristoylation site near its N-terminus (12GACHGG17; SEQ ID NO:28), in addition to potential glycosylation (114NSSF117; SEQ ID NO: 50) and PKC and CK2 phosphorylation sites. Since myristoylation frequently directs proteins to the plasma membrane and many receptors and other signaling components are associated with the plasma membrane, SABP2's putative myristoylation sequence will be mutated to determine if it is necessary for fatty acylation, membrane association or function of SABP2. AtSB2L5 and AtSB2L9, SABP2 related genes in *Arabidopsis*, also have myristoylation sites near their N-terminus.

Enyzmatic Activity

SABP2 and its ortholog(s) possess enzymatic activity. A comparison of amino acid sequence and/or enzyme activity(s) for SABP2 and its *Arabidopsis* ortholog(s) (which have SA-binding activity and whose silencing suppresses certain defense responses) will facilitate the identification of SABP2's biochemical activity that is relevant to SA-mediated defense responses.

Figure 6B:
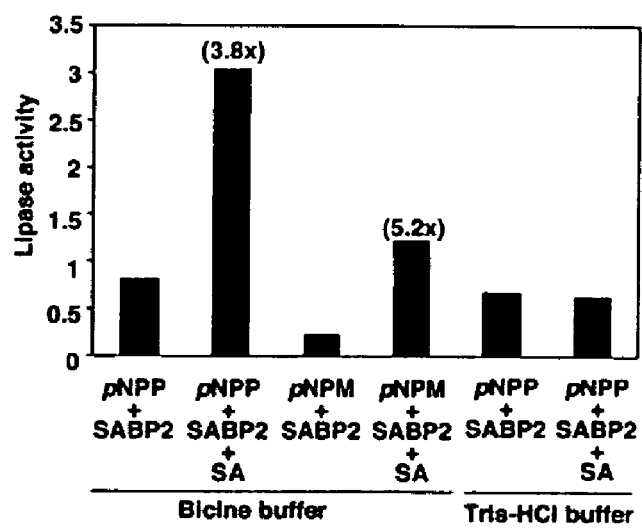

Since SABP2 contains the catalytic triad and the lipase signature sequence, the recombinant protein was tested for lipase activity. Highly purified recombinant SABP2 (rSABP2) exhibited lipase/esterase activity with 4-methylumbelliferone butyrate in an in gel assay, and with para-nitrophenyl (pNP) butyrate in a solution assay (FIG. 6A). rSABP2 also cleaved esters containing long carbon chains such as pNP palmitate (C-16) and pNP myristate (C-14) (FIG. 6B), thereby demonstrating true lipase activity. Addition of SA to the reaction stimulated lipase activity 3–6 fold (FIG. 6B). This stimulation required SA binding to SABP2, since it was abolished in reaction conditions that prevented SA binding. In contrast to SABP2, the lipase from Mucor meihei did not exhibit stimulation by SA, indicating that SA stimulation of lipase activity is not a general phenomenon (data not shown). The lipase activity assay was performed as described by Yang et al. with modifications to allow SA binding to SABP2. The standard 1 ml assay mixture consisted of 1 mM substrate in 50 mM Bicine pH 8.0, 0.05% Triton-X100. Following a 60 min preincubation on ice in absence or presence of 1 mM SA, the reaction was allowed to proceed at 24° C. for 60 min. A 100 mM stock solution of p-NPM or p-NPP was prepared in acetonitrile. Lipase activity was estimated colorimetrically (Unicom UV1, Spectronic Unicom, UK) by measuring the liberation of para-nitrophenol from p-NPP or p-NPM at 410 nm. Measurements from control reactions without SABP2 were subtracted from each reaction. For non SA-binding conditions, Tris-HCl pH 8.0 (50 mM) was used in placed of Bicine buffer.

To further assess whether SABP2 has an additional enzymatic activity, a set of model substrates are employed in a systematic approach to identify the enzyme activity(s) of SABP2 and its *Arabidopsis* ortholog(s). This set has previously been employed by Waspi et al. (Waspi, U. et al., 1998) and Baudouin et al (Baudouin et al., 1997) to characterize two other α/β fold hydrolases, Pir7b of rice and Hsr203J of tobacco, the first of which is closely related by sequence to SABP2 and the AtSB2Ls. Like SABP2 they contain the catalytic triad and lipase signature sequence and are induced at the transcription level during defense responses to pathogens. Pir7b's preferred substrate is naphthol AS-esters while Hsr203J prefers short-chain dinitrophenyl acyl esters. For esterase activity the following potential substrates, p-nitrophenyl butyrate, acetylcholine, 2-naphthol butyrate/acetate and 2-naphthol AS-acetate are employed. Amidase activity is monitored with acetanilide and nitro-acetanilide, while epoxide hydrolase activity analysis utilizes 9R-10S-epoxystearic acid. Protease activity is assayed with casein as the substrate.

Sequence comparisons have revealed that SABP2 is closely related to several proteins with hydroxynitrile lyase (Hnl) activity; these proteins also contain the catalytic triad and a lipase signature sequence. Based on sequence homology, the AtSB2Ls also have been designated Hnls. To test if SABP2 and the AtSB2Ls with SA-binding activity exhibit Hnl activity, the decomposition of cyanohydrins is monitored as described by Selmar et al. (1987) and Hasslacher et al. (1996) in the absence or presence of SA. If SABP2 exhibits SA-stimulated Hnl activity, it is possible that SABP2 signals defenses via HCN production. In contrast to some plants that release large quantities of HCN from large cyanogenic glycoside reserves upon predation, most plants, including tobacco and *Arabidopsis*, contain little or no cyanogenic glycosides. Perhaps in these non-cyanogenic plant species, SABP2/AtSB2Ls release small quantities of HCN from previously undetected small reserves, and these are sufficient to activate a local response(s). Consistent with this possibility, treating tobacco with KCN induces resistance to TMV, possibly due to increased expression of alternative oxidase (Murphy et al., 1999).

The data described above (FIGS. 6A and 6B) indicate that SABP2 (and its *Arabidopsis* ortholog[s]) is a lipase, whose activity is stimulated by SA binding. SABP2's lipase activity and SA's ability to alter this activity suggests a link between SA and lipids/fatty acids. While the nature of this connection is presently unclear, it is intriguing that not only do two other proteins involved in disease resistance (EDS1 and PAD4) have a putative lipase activity and interface with SA (perhaps through a positive feedback loop), but several more recent reports provide further evidence for a role of lipids/FAs in SA-mediated defense signaling. Work on the *Arabidopsis* mutant ssi2 suggests that oleic acid or its derivative suppresses SA-mediated defense responses such as PR-1 induction and resistance to P.s. and *P. parasitica*, while in contrast it acts in conjunction with JA to induce PDF1.2 expression and resistance to *Botrytis cinerea* (Kachroo et al., 2001). Lamb and colleagues (Maldonado et al., 2002) recently described another *Arabidopsis* mutant dir1 which is defective in induction of systemic resistance. DIR1 is a putative lipid transfer protein, which is required for the production or transmission of the mobile signal that moves from infected tissue through the phloem to induce SAR in uninoculated parts of the plant.

EXAMPLE III

Sabp2 is Important for Resistance to Pathogens

The present inventors have demonstrated that SABP2 silencing in plants gives rise to decreased resistance to TMV and also repressed induction of the PR-1 gene by TMV infection or by SA treatment.

Materials and Methods

Plasmid Construction and Plant Transformation. The RNAi-SABP2 construct was made in the pHANNIBAL vector by (Smith et al. 2000) inserting a 404 bp fragment corresponding to the 5' portion of SABP2. The fragment corresponding to the sense arm of the hairpin loop was generated using the primers F6 (CCGCTCGAGATGAAG-GAAGGAAAACACTTG) (SEQ ID NO: 53) and F7 (GGGGTACCAGATCAGTTGTATTTATGGGC) (SEQ ID NO:54) and cloned in the Xho1-Kpn1 site. The fragment for the anti-sense arm was generated using the primers F2 (described above) and G2 (GCGGGATCCCTGAGTATC-CAACCAATTCTCGG) (SEQ ID NO:55) and was cloned into the BamH1 site. The Not1 fragment from pHANNIBAL containing SABP2 was then subcloned into binary vector pART27. The sequences of these constructs were confirmed by DNA sequencing. *Agrobacterium* strain LBA4404 was transformed with the silencing construct by electroporation. Plant transformations, regeneration and maintenance of the transgenic lines were carried out as described by Shah and Klessig (Shah et al., 1996).

RNA Blot Analysis and RT-PCR Analysis. Total RNA was extracted from tobacco leaves as described by Kumar et al. (1997). Ten μg total RNA per lane was used for RNA blot analyses. Blots were hybridized with desired probes. Hybridizations were carried out as described by Tang et al. (1999) and exposed to phosphorimager screen or X-ray film.

First strand cDNA was synthesized using 2 μg total RNA isolated from control and silenced plants as described above. Semi-quantitative RT-PCR analysis was performed using 1 μl of the cDNA in a 20 μl reaction mixture containing primers G6 (TGGCCCAAAGTTCTTGGC) (SEQ ID NO: 56) and E6 (AGAGATCAGTTGTATTTATG) (SEQ ID NO:10) which anneal outside the region used for silencing SABP2 expression. Control reactions to normalize RT-PCR amplifications were run with the primers derived from constitutively expressed translation elongation factor 1. (EF1α) (forward, TCACATCAACATTGTGGTCATTGGC (SEQ ID NO:57); reverse, TTGATCTGGTCAAGAGCCT-CAAG (SEQ ID NO:58)). PCR was performed for 30 cycles at 55° C. annealing temperature.

Results

SABP2 Expression is Required for Complete Local and Systemic Resistance to TMV. To assess the role of SABP2 in defense signaling, SABP2 expression was silenced using RNA interference (RNAi) (Wesley et al., 2001). RNA blot analysis of 16 independently generated $T_1$ lines expressing the RNAi-SABP2 construct revealed that SABP2 expression was suppressed more than 75% as compared with the empty vector control plants (FIG. 8A). These 16 lines develop TMV lesions which on average were 41% larger than on the empty vector lines (FIG. 8B), as predicted if SABP2 plays a positive role in resisting TMV infection. Note that in the SA-deficient, NahG transgenic tobacco lines TMV lesion size was on average 23% larger (Gaffney, T. et al., 1993). Thus, suppression of SABP2 expression appears to be at least as disruptive to TMV resistance as destruction of the SA signal.

RNA blot analysis of 5 independent $T_2$ lines similarly revealed little SABP2 transcript accumulation before or after TMV infection, and the lesions were on average 34% larger than those on the control lines (FIG. 8E). Moreover, transcripts for the TMV coat protein (CP) accumulated to higher levels in the inoculated leaves of SABP2-suppressed lines as compared with control plants.

SA induction of PR-1 expression, which is associated with local resistance to TMV, was also affected in SABP2-silenced plants. Suppression of SA-induced PR-1 expression was readily detected in the $T_1$, generation of the five lines SABP2-silenced plants in which little, if any, SABP2 transcripts could be detected by RT-PCR under the conditions used (FIGS. 8B and 8F). In the $T_2$ generation of these five lines the level of SABP2-silencing was more variable (FIG. 8G). In plants in which SABP2 transcript was undetectable SA induction of PR-1 expression was suppressed (see FIG. 8G, e.g. transgenic 1-2). However, in plants in which silencing was less effective, suppression of PR-1 induction was poor (e.g. transgenic 1-3 and 1-4). These results suggest that silencing was less effective in the $T_2$ generation and that suppression of SA-induction of PR-1 expression was dependent on the level of SABP2 silencing.

Whether SAR development also is suppressed in the SABP2-silenced lines was then assessed. In control plants, the lesions formed after a secondary infection were ~50% smaller than those produced after a primary infection (FIG. 9A and 9B); this reduction in secondary lesion size is a common marker for SAR. By contrast, the lesions formed on secondarily inoculated SABP2-silenced plants were as large as those formed after a primary infection and 2.5-fold larger than those exhibited by control plants. SABP2-silenced plants also exhibited increased viral replication, as indicated by higher levels of TMV movement protein (MP) transcript in the systemic leaves of SABP2-silenced plants than control plants after secondary inoculation (FIG. 9C). In addition, systemic expression of the PR-1 gene, another common marker for SAR, was reduced in SABP2-silenced plants. Unlike control plants, whose uninoculated leaves accumulated low to moderate levels of PR-1 transcript following a primary infection (FIG. 9C), the systemic leaves of SABP2-silenced plants contained little to no PR-1 mRNA. Following a secondary infection with TMV, however, the challenge-inoculated leaves of SABP2-silenced plants accumulated more PR-1 transcripts than those of control plants. Taken together, these results suggest that SABP2 plays a role(s) in restricting viral replication/spread in TMV-inoculated leaves, as evidenced by increased lesion size and greater accumulation of transcripts for TMV CP. They also indicate that SABP2 expression is required for systemic PR-1 expression and the characteristic reduction in lesion size and viral replication associated with SAR.

Discussion

The combined observations that SABP2 binds SA with high affinity, is present in exceedingly low concentrations, and displays SA-stimulated enzymatic activity, provide evidence that SABP2 is a receptor for SA. Further supporting this hypothesis, local and systemic resistance in SABP2-silenced plants was disrupted at least as effectively as in SA-deficient tobacco expressing the nahG transgene. Following a primary infection with TMV, the lesions formed on $T_1$, and $T_2$ generations of SABP2-silenced plants were on average 41% and 34% larger, respectively, than those of control plants, while those formed on NahG tobacco were only 23% larger on average (Gaffney et al. 1993). In addition, neither SABP2-silenced nor nahG-expressing plants developed SAR. Further evidence that SABP2 is an SA receptor is the reduced ability of SA to induce PR-1 expression in plants effectively silenced for SABP2. Interestingly SABP2 silencing was more variable and generally less effective in $T_2$ versus $T_1$ plants. Less effective silencing of SABP2 correlated with poor suppression of PR-1 induction, suggesting that the residual SABP2 level in these $T_2$ plants is at or above a threshold required for SA induction of PR-1, while in the $T_1$ plants and a minority of $T_2$ plants (e.g. transgenic 1-2 in FIG. 8G), it is below this level. Since local and systemic resistance were impaired in all $T_2$ plants tested, the level of SABP2 required for resistance appears to be higher than that needed for PR-1 gene activation. The efficiency of SABP2 silencing did appear to influence how severely resistance was impaired, however, because the primary TMV lesions on $T_2$ plants were not as large as those on $T_1$ plants.

The reduction in local resistance, inability to activate SAR and loss of SA responsiveness exhibited by SABP2-silenced plants is very similar to the phenotype of SA-insensitive, SAR-defective npr1/nim1/sai1 Arabidopsis mutants (Cao et al., 1994; Delaney et al., 1995; Glazebrook, 1996; Shah, 1997). NPR1 is an important signal transducer that functions downstream of SA in the defense signaling pathway. This protein contains ankyrin repeats and shares limited homology with the IκBα subclass of transcription factors/inhibitors in animals, which regulate immune and inflammatory responses (Cao et al., 1997; Ryals, 1997). Recent studies have revealed that NPR1 is maintained in the cytoplasm as an oligomer formed through intermolecular disulfide bonds (Mou et al. 2003). Treatment with SA (or its analog 2,6-dichloro isonicotinic acid) or infection with pathogens alters the cellular reduction potential, thereby promoting monomerization of NPR1; these monomers then are translocated to the nucleus, a prerequisite for PR-1 gene activation (Mou et al., 2003; Kinkema et al. 2000). While these findings provide one mechanism of action for SA, an additional mechanism(s) also must exist to account for the poorer induction of PR-1 expression and disease resistance in transgenic npr1-1 mutant Arabidopsis that constitutively accumulate monomeric, nuclear-localized NPR1 than in 2,6-dichloro isonicotinic acid-treated wt plants (Mou et al., 2003). Furthermore, NPR1 was recently shown to regulate SA-mediated suppression of jasmonic acid signaling via a mechanism that does not require nuclear localization (Spoel et al., 2003). Thus the similarities between SABP2-silenced and npr1/nim1/sai1 plants strongly argue that SABP2 is an important component of this pathway that functions at a point downstream of SA.

The discovery that SABP2 displays SA-stimulated lipase activity and SABP2 is required for local and systemic resistance, suggests SABP2's lipase is required to signal resistance. One possible mechanism for resistance-specific SABP2 activation is via direct stimulation of its lipase activity by SA. This might be mediated by SA-facilitated displacement of the lid, a surface loop found on many lipases and other α/β fold hydrolases that covers the active site and regulates substrate selection and binding (Nardini et al., 1999). SABP2 activity also may be increased by enhanced gene expression since SABP2 transcript levels increased in TMV-infected tobacco plants (FIG. 8E).

The mechanism through which SABP2's lipase activity transduces the defense signal is not known. However, there is growing evidence that lipids play an important role in signaling disease resistance. The EDS1 and PAD4 proteins of Arabidopsis, which are putative lipases, are required to transduce the resistance signal following pathogen recognition by a specific class of resistance (R) genes. While these proteins share little homology with SABP2, all three contain the catalytic triad and the lipase signature sequence (Falk et al., 1999; Jirage et al., 1999). A fatty acid (FA) desaturase also has been linked with resistance signaling. The ssi2 mutation in Arabidopsis, which impairs stearoyl desaturase activity and thereby alters cellular FA content, confers constitutive activation of several SA-associated defense responses and suppression of certain JA-dependent defenses (Kachroo et al., 2001; Shah et al., 2001). More recently, a defect in a putative apoplastic lipid transfer protein caused by the dir1-1 mutation was shown to impair systemic, but not local, resistance in pathogen-infected Arabidopsis (Maldonado et al., 2002). DIR1 therefore appears to play a role in generating or translocating the SAR signal that moves from inoculated leaves to other parts of the plant. Given that both dir1-1 mutant and SABP2-silenced plants are defective in developing SAR, it is tempting to speculate that SABP2's SA-stimulated lipase activity generates a SAR-inducing lipid (or lipid derivative) that is translocated by the DIR1-encoded lipid transfer protein to the uninoculated parts of the plant. Since some AtSB2L (also referred to as SABP2L) proteins do not bind SA, these may bind other ligands, such as stress-associated hormones like JA or abscisic acid. Indeed, these proteins may comprise a family of receptors that, upon binding their cognate ligand, exhibit enhanced hydrolase (lipase/esterase) activity. Different members, or sets of members, would likely display distinct substrate specificities, thereby ensuring that the proper response is signaled. Alternatively, sequence similarity between SABP2 and other known proteins, including several plant hydroxynitrile lyases (Hnls) and lecithin (phosphatidylcholine) cholesterol acyl transferase (Jonas et al., 2000) from animals, raises the possibility that some SABP2/AtSB2L family members have other enzymatic activities. For example, some SABP2/AtSB2L members might catalyze the release of toxic hydrogen cyanide (HCN) from cyanogenic glycosides, perhaps for defense against herbivorous insects and pathogens (Hickel et al., 1996). Tobacco and Arabidopsis contain very low to undetectable levels of cyanogenic glycosides; however, an SABP2/AtSB2L Hnl might be able to release small quantities of HCN from a previously undetected store of cyanogenic glycoside and thereby activate local defense responses. In support of this possibility, KCN treatment induces TMV resistance in tobacco, possibly by increasing expression of alternative oxidase (Chivasa et al., 1998). Alternatively, it is possible that one or more members of the SABP2/SABP2L family has JA-stimulated protease activity which releases systemin and other peptide hormones from a common precursor for systemic activation of plant defenses against herbivorous insects (Pearce et al., 2003).

In summary, the results presented herein provide evidence that SABP2 is a resistance signaling receptor for SA. The steps activated downstream of this SA effector protein are not yet known. However, the ability of SA to regulate SABP2's lipase activity suggests a mechanism through which lipids/FA are linked to the SA-dependent defense signaling pathway.

EXAMPLE IV

Identification and Characterization of *Arabidopsis* SB2LS

The extensive collection of mutants affecting disease resistance and SA-mediated defense responses and the availability of its genomic sequence make *Arabidopsis* an ideal plant to study disease resistance. Moreover, *Arabidopsis* contains an SABP2-like activity (Du, H. et al., 1997) and has a large gene family (18 full-length members) which encode proteins with 32–57% identity and 46–71% similarity to SABP2, two of which have already been shown to have specific SA-binding activity (see Table IV), one of which is induced by infection. Note that while at least 15 are expressed (ESTs available) and have sequences suggesting they are esterases, lipases or lyases, none have a known function. Thus, characterization of this family to determine which has SA-binding activity and of these, what affect does silencing (knock out (KO) or dsRNA mediated) have on the plant's phenotype, particularly with respect to disease resistance, will help further understanding of the disease resistance pathway.

Two parallel types of experimentation are performed initially. First, select members of this family continue to be cloned, expressed, and analyzed for the SA-binding. A dendrogram of SB2Ls (FIG. 10) suggests that they can be grouped into five subfamilies. To date several members of subfamily I and II, the subfamilies most closely related to tobacco SABP2, have been tested for SA-binding activity. All members of subfamilies I and II and select members of the more distant subfamilies III–V can also be analyzed.

In parallel two approaches are used to obtain transgenic or mutant *Arabidopsis* with altered expression of one or more members of the AtSB2L family. If a limited number have SA-binding activity, then T-DNA derived KO or activation-tagged mutants for these family members will be obtained from the UW *Arabidopsis* KO Facility (α and β populations) and from the Salk Institute Genomic Analysis Lab's libraries. KOs have been obtained for five AtSB2Ls from the Salk Institute collection that correspond to two SA-binding AtSB2Ls, AtSB2L5 (subfamily I) and AtSB2L9 (subfamily II), another member of subfamily I (AtSB2L1), one member of subfamily IV (AtSB2L16), and one of subfamily V (AtSB2L14). These five KO lines can initially be screened for altered defense responses to avirulent P. s. (e.g. HR, pathogen growth) or to SA treatment (e.g. induction of PR-1, PR-2, and PR-5), as well as SA-binding activity for AtSB2L7, AtSB2L14 and AtSB2L15. (If, as anticipated, one or more of these three latter KOs do not have SA-binding activity, it will serve as a good negative control). A secondary screen of the more interesting KOs would include resistance to an avirulent pathovar of *P. parasitica* and expression of other defense genes such as GSTs, PR-3, PR-4 and defensin (PDF1.2).

Knockout of a single AtSB2L may not alter defense response because of possible redundancy. If there are only a small number of AtSB2Ls with SA-binding activity, then one approach will be to cross the different KO lines to generate lines with 2, 3, or more of the SA-binding AtSB2Ls silenced. This approach is less likely to be successful if a significant number (e.g. >5) of the AtSB2Ls bind SA. The better approach then will be dsRNA-mediated gene silencing in stable transgenics as outlined above for SABP2. Because of sequence divergence among the family members, particularly at the DNA level, silencing of all members with one construct is not possible. Initially and in parallel with initial screening of the readily available KOs, all members of subfamily II will be silenced with one construct and most subfamily I members using sequences that are highly conserved within that subfamily. Effective silencing requires a minimum of 50 nucleotides with 80% or more identity. In subfamily II there is a 65 nucleotide region with 80% identity among all five members located between 678 and 742, with the A of the initiation codon of AtSB2L9 designated 1. No such conserved region is present in all four subfamily I members; however, there is a 153n region with 79% identity for AtSB2L1, 2, and 8 located between 3 and 155 with the A of AtSB2L1's ATG as 1. This sequence will be used to silence these three members in the Salk line in which the fourth member, AtSB2L5, is knocked out. Also the number of AtSB2Ls that bind SA are determined, careful analysis of sequences of these genes may identify a highly conserved region against which the dsRNA could be targeted for silencing of all, or at least most, of the SA-binding AtSB2Ls.

Construction and characterization of transgenic lines that overexpress one of the SA-binding AtSB2Ls may also be informative and will be done for a limited number of these AtSB2Ls, particularly if silencing of that AtSB2L alters defense responses. The expression of SA-binding AtSB2Ls will also be monitored to see if they are induced by infection with avirulent or virulent pathogens (e.g. TCV, P. s., *P. parasitica*) or treatment with SA (or BTH).

This large family of AtSB2Ls may provide an opportunity to identify a region of these proteins which is required for SA binding. Comparison of the a.a. sequences of these AtSB2Ls with SA-binding activity (and SABP2) versus those of non-binding homologues may reveal a region (and possibly even critical a.a.'s) that is likely involved in SA binding. This will be confirmed by swapping of this putative domain between closely related binding and non-binding homologues, preferably within the same subfamily. Site-directed mutagenesis could then be used to confirm or dispel the involvement of a.a.'s predicted to be important based on sequence analysis. Once the enzymatic activity involved in transmitting the SA signal by SABP2 and its *Arabidopsis* ortholog(s) has been defined, then the effects of these mutations on it, as well as SA binding, will be determined.

The *Arabidopsis thaliana* SABP2-like gene family members are referred to herein as follows:

AtSB2L1, Genbank Accession No NM_127926 (SEQ ID NO:32),

AtSB2L2 Genbank Accession No NM_127924 (SEQ ID NO:33),

AtSB2L3 Genbank Accession No NM_127925 (SEQ ID NO:34),

AtSB2L4 Genbank Accession No NM_127922 (SEQ ID NO:35),
AtSB2L5, Genbank Accession No NM_121068 (SEQ ID NO:36),
AtSB2L6 Genbank Accession No NM_127919 (SEQ ID NO:37),
AtSB2L7 Locus At2g23560 Accession No NM_127920 (SEQ ID NO:38),
AtSB2L8 Genbank Accession No NM_127923 (SEQ ID NO:39),
AtSB2L9 Genbank Accession No NM_119878 (SEQ ID NO:40),
AtSB2L10 Genbank Accession No NM_114904 (SEQ ID NO: 41),
AtSB2L11 Genbank Accession No NM_113902 (SEQ ID NO:42),
AtSB2L12 Genbank Accession No NM_117058 (SEQ ID NO:43),
AtSB2L13 Genbank Accession No NM_102400 (SEQ ID NO:44),
AtSB2L14 Genbank Accession No NM_103121 (SEQ ID NO:45),
AtSB2L15 Genbank Accession No NM_105591(SEQ ID NO:46),
AtSB2L16 Genbank Accession No NM_117770 (SEQ ID NO:47),
AtSB2L17 Genbank Accession No NM_111924 (SEQ ID NO:48), and
AtSB2L18 Genbank Accession No NM_125216 (SEQ ID NO:49).

References

Aarts, N., Metz, M., Holub, E., Staskawicz, B. J., Daniels, M. J. and Parker, J. E. 1998. Different requirements for EDS1 and NDR1 by disease resistance genes define at least two R gene-mediated signaling pathways in *Arabidopsis*. Proc. Natl. Acad. Sci. USA 95: 10306–10311.

Abramson, S., Korchak, H., Ludewig, R., Edelson, H., Haines, K., Levin, R. I., Herman, R., Rider, L., Kimmel, S. and Weissmann, G. 1985. Models of action of aspirin-like drugs. Proc. Natl. Acad. Sci. USA, 82: 7227–7231.

Anderson, M., Chen, Z., and Klessig, D. F., 1998. Possible involvement of lipid peroxidation in salicylic acid-mediated induction of PR-1 gene expression. Phytochemistry 47: 555–566.

Antoniw, J. F., White, R. F., 1980. The effects of aspirin and polyacrylic acid on soluble leaf proteins and resistance to virus infection in five cultivars of tobacco. Phytopathol. Z. 98: 331–341.

Aoyama, T. and Chua, N. H. 1997. A glucocorticoid-mediated transcriptional induction system in transgenic plants. Plant J. 11: 605–612.

Aronheim, A., Zandi, E., Henneman, H., Elledge, S. J. and Karin, M. 1997. Isolation of an AP-1 repressor by a novel method for detecting protein-protein interactions. Mol. Cell. Biol. 17: 3094–3102.

Austin, M. J., Muskett, P., Kahn, K., Feys, B. J., Jones, J. D. G. and Parker, J. E. 2002. Regulatory role of SGT1 in early R gene-mediated plant defenses. Science 295: 2077–2080.

Baudouin, E., Charpenteau, M., Roby, D., Marco, Y., Ranjeva, R. and Ranty, B. 1997. Functional expression of a tobacco gene related to the serine hydrolase family; Esterase activity towards short-chain dinitrophenyl acylesters. Eur. J. Biochem. 248: 700–706.

Benhamou, N. and Belanger, R. R., 1998. Benzothiadiazole-mediated induced resistance to *fusarium oxysporum f.* sp. radicis-lycopersici in tomato. Plant Physiol. 118:1203–1212.

Bowling, S. A., Guo, A., Cao, H., Gordon, A. S., Klessig, D. F., Dong, X., 1994. A mutation in *Arabidopsis* that leads to constitutive expression of systemic acquired resistance. Plant Cell 6: 1845–1857.

Bi, Y. M., Kenton, P., Mur, L., Darby, R., and Draper, J., 1995. Hydrogen peroxide does not function downstream of salicylic acid in the induction of PR protein expression. Plant J. 8: 235–245.

Buchanan, B. B., Gruissem, W. and Jones, R. L. (editors) 2000 In Biochemistry and Molecular Biology of Plants. pp. 956–960.

Cao, H., Bowling, S. A., Gordon, A. S., Dong, X., 1994. Characterization of an *Arabidopsis* mutant that is nonresponsive to inducers of systemic acquired resistance. Plant Cell 6: 1583–1592.

Cao, H., Li, X., and Dong, X. 1998. Generation of broad-spectrum disease resistance by overexpression of an essential regulatory gene in systemic acquired resistance. Proc. Natl. Acad. Sci. USA 95: 6531–6536. Cao, H., Glazebrook, J., Clark, J. D., Volko, S. & Dong, X. (1997) Cell 88, 57–64.

Carr, J. P., Dixon, D. C., Nikolau, B. J., Voelkerding, K. V. and Klessig, D. F. 1989. Synthesis and localization of pathogenesis-related proteins in tobacco. Mol. Cell Biol. 7: 1580–1583.

Chamnongpol, S., Willekens, H., Langebartels, C., Van Montagu, M., Inze, D., Van Camp, W., 1996. Transgenic tobacco with a reduced catalase activity develops necrotic lesions and induces pathogenesis-related expression under high light. Plant J. 10: 491–503.

Chandra, S., Heinstein, P. F. and Low, P. S. 1996. Activation of phospholipase A by plant defense elicitors. Plant Physiol. 110: 979–986.

Chen, Z., and Klessig, D. F., 1991. Identification of a soluble salicylic acid-binding protein that may function in signal transduction in the plant disease-resistance response. Proc. Natl. Acad. Sci. USA 88: 8179–8183.

Chen, Z., Ricigliano, J. W., and Klessig, D. F., 1993a. Purification and characterization of a soluble salicylic acid-binding protein from tobacco. Proc. Natl. Acad. Sci. USA 90: 9533–9537.

Chen, Z., Silva, H., and Klessig, D. F., 1993b. Active oxygen species in the induction of plant systemic acquired resistance by salicylic acid. Science 262: 1883–1886.

Chivasa, S. and Carr, J. P., 1998. Cyanide restores N gene-mediated resistance to tobacco mosaic virus in transgenic tobacco expressing salicylic acid hydrolase. Plant Cell 10: 1489–1498.

Chivasa, S., Murphy, A. M., Naylor, M., and Carr, J. P., 1997. Salicylic acid interferes with tobacco mosaic virus replication via a novel salicylhydroxamic acid-sensitive mechanism. Plant Cell 9: 547–557.

Conn, E. E., 1981. Cyanogenic glycosides. In *The Biochemistry of Plants: A complete Treastise*. Edited by Stump P. K., Conn, E. E., New York: Academic Press 7: 479–500.

Conrath, U., Chen, Z., Ricigliano, J. W., and Klessig, D. F., 1995. Two inducers of plant defense responses, 2,4-dichloroisonicotinic acid and salicylic acid, inhibit catalase activity in tobacco. Proc. Natl. Acad. Sci. USA 92: 7134–7147. Cutt, J. R. and Klessig D. F. 1992. Salicylic Acid, A Changing Perspective. Pharmaceutical Technology 16: 26–34.

de Laat, A. M. M. and van Loon, L. C. 1982. Regulation of ethylene biosynthesis in virus-infected tobacco leaves: II. Time course of levels of intermediates and in vivo conversion rates. Plant Physiol. 69: 240–245.

Delaney, T. P., Uknes, S., Vernooij, B., Friedrich, L., Weymann, K., Negrotto, D., Gaffney, T., Gut-Rella, M., Kessmann, H., Ward, E. and Ryals, J. 1994. A central role of salicylic acid in plant disease resistance. Science 266: 1247–1250.

Delaney, T. P., Friedrich, L., Ryals, J. A., 1995. *Arabidopsis* signal transduction mutant defective in chemically and biologically induced disease resistance. Proc. Natl. Acad. Sci. USA 92: 6602–6606.

Dempsey, D., Shah, J. and Klessig, D. F., 1999. Salicylic acid and disease resistance in plants. Critical Reviews in Plant Sciences 18: 547–575.

Dempsey, D. A., and Klessig, D. F., 1995. Signals in Plant Disease Resistance. Bulletin de l' institute Pasteur 93: 167–186.

Dietrich, R. A., Delaney, T. P., Uknes, S. J., Ward, E. R., Ryals, J. A., Dangl, J. L., 1994. *Arabidopsis* mutants simulating disease resistance response. Cell 77: 565–577.

Dixon, D. C., Cutt, J. R. and Klessig, D. F. 1991. Differential targeting of the tobacco PR-1 pathogenesis-related proteins to the extracellular space and vacuoles of crystal idioblasts. EMBO J. 10: 1317–1324.

Dogru, E., Warzecha, H., Seibel, F., Haebel, S., Lottspeich, F. and Söckigt, J., 2000. The gene encoding polyneuridine aldehyde esterase of monoterpenoid indole alkaloid in plants is an ortholog of the a/b hydrolase superfamily. Eur. J. Biochem 267: 1397–1406.

Draper, J. 1997. Salicylate, superoxide synthesis and cell suicide in plant defense. Trends in Plant Sci. 2: 162–165.

Du, H. and Klessig, D. F., 1997. Identification of a salicylic acid-binding protein in tobacco. Plant Physiol. 113: 1319–1327.

Durner, J. and Klessig, D. F., 1995. Inhibition of ascorbate peroxidase by salicylic acid and 2,6-dichloroisonicotinic acid, two inducers of plant defense. Proc. Natl. Acad. Sci. USA 92: 11312–11316.

Durner, J. and Klessig, D. F., 1996. Salicylic acid is a modulator of tobacco and mammalian catalases. J. Biol. Chem. 271: 28492–28501.

Durner, J., Shah, J., and Klessig, D. F. 1997. Salicylic acid and disease resistance in plants. *Trends Plant Sci.* 2: 266–274.

Durner, J., Wendehenne, D. and Klessig, D. F. 1998. Defense gene induction in tobacco by nitric oxide, cyclic GMP and cyclic ADP ribose. Proc. Natl. Acad. Sci. USA 95: 10328–10333.

Falk, A., Feys, B. J., Frost, L. N., Jones, J. D. G., Daniels, M. J. and Parker, J. E. 1999. EDS1, an essential component of R gene-mediated disease resistance in *Arabidopsis* has homology to eukaryotic lipases. Proc. Natl. Acad. Sci. USA 96:3292–3297.

Fields, S. and Song, O. K. 1989. A novel genetic system to detect protein-protein interactions. Nature 340: 245–246.

Foger, B., Chase, M., Amar, M. J., Vaisman, B. L., Shamburek, R. D., Paigen, B., Furchart-Najib, J., Paiz, J. A., Koch, C. A., Hoyt Jr., R. F., Brewer Jr., H. B., and Santamarina-Fojo, S. 1999. Chloesteryl ester transfer protein corrects dysfunctional high density lipoproteins and reduces aortic atherosclerosis in lecithin cholesterol acyltransferase transgenic mice. J. Biol. Chem. 274: 36912–36920

Gaffney, T., Friedrich, L., Vernooij, B., Negrotto, D., Nye, G., Uknes, S., Ward, E., Kessmann, H., and Ryals, J. 1993. Requirement of salicylic acid for the induction of systemic acquired resistance. Science 261: 754–756.

Glazebrook, J., Rogers, E. E. and Ausubel, F. M. 1996. Isolation of *Arabidopsis* mutants with enhanced disease susceptibility by direct screening. Genetics 143: 973–982.

Görlach J. Volrath, S., Knauf-Beiter, G., Hengy, G., Beckhove, U., Kogel, K-H., Oostendrop, M., Staub, T., Ward, E., Kessmann, H., and Ryals, J. 1996. Benzothiadiazole, a novel class of inducers of systemic acquired resistance, activates gene expression and disease resistance in wheat. Plant Cell 8: 629–643.

Greenberg, J. T., Guo, A., Klessig, D. F., Ausubel, F. M., 1994. Programmed cell death in plants: a pathogen-triggered response activated coordinately with multiple defense functions. Cell 77: 551–563.

Hammond-Kosack, K. E. and J. D. G. Jones 1996. Resistance gene-dependent plant defense responses. Plant Cell 8: 1773–1791.

Hasslacher, M., Schall, M., Hayn, M., Griengl, H. Kohlwein, S. D. and Schwab, H. 1996. Molecular cloning of the full-length cDNA of (S)-hydroxynitrile lyase from *Hevea brasiliensis*. J. Biol. Chem. 271: 5884–5891.

Hickel, A., Hasslacher, M. and Griengl, H., 1996. Hydroxynitrile lyases: Functions and properties. Physiologia Plantarum 98: 891–898.

Hoeg, J. M., Santamarina-Fogo, S., Berard, A. M., Cornhill, J. F., Herderick, E. E., Feldman, S. H., Haudenschild, C. C., Vaisman, B. L., Hoyt Jr., R. F., Demosky Jr., S. J., Kauffman, R. D., Hazel, C. M., Marcovina, S. M. and Brewer Jr., H. B. 1996. Overexpression of lecithin:cholesterol acyltransferase in transgenic rabbits prevents diet-induced atherosclerosis. Proc. Natl. Acad. Sci. USA, 93: 11448–11453

Ishii, H., Tomita Y., Horio T., Narusaka, Y., Nishimura K. and Iwamoto, S. 1999. Induced resistance of acibenzolar-S-methyl (CGA 245 704) to cucumber and Japanese pear diseases. Eur. J. Plant Pathol. 105: 77–85.

Jirage, D., Tootle, T. L., Reuber, T. L., Frost, L. N., Feys, B. J., Parker, J. E.,Ausubel, F. M. and Glazebrook, J. 1999. *Arabidopsis* thaliana PAD4 encodes a lipase-like gene that is important for salicylic acid signaling.

Proc. Natl. Acad. Sci. USA 96:13583–13588.

Jonas, A., 2000. Lecithin cholesterol acyltransferase. Biochim. Biophys. Acta 1529: 245–256.

Kachroo, P., Shanklin, J., Shah, J., Whittle, E. J. and Klessig, D. F. 2001. A fatty acid desaturase modulates the activation of defense signaling pathways in plants. Proc. Natl. Acad. Sci. USA. 98: 9448–9453.

Kaji, M., Hirata, A., Nakajima, Y., Sugii, S. and Tsujimoto, K. 1997. Control mechanism of new plant activator, CGA245704 against rice blast. Annals of the Phytopathological Society of Japan 63: 222–223.

Kakes, P., 1990. Properties and functions of the cyanogenic system in higher plants. Euphytica 48: 25–43. Kauss, H. and Jeblick, W., 1995. Pretreatment of parsley suspension cultures with salicylic acid enhances spontaneous and elicited production of $H_2O_2$. Plant Physiol 108: 1171–1178.

Kakidani and Ptashne, 1988. GAL4 activates gene expression in mammalian cells. Cell 52:161–167.

Kimber, M. S. and Pai, E. F. 2000. The active site architecture of *Pisum sativum* (-carbonic anhydrase is a mirror image of that of (-carbonic anhydrase. EMBO J. 19: 1407–1418.

Kinkema, M., Fan, W. & Dong, X. (2000) Plant Cell 12, 2339–2350. Klessig, D. F., Malamy, J., 1994. The salicylic acid signal in plants. Plant Mol. Biol. 26: 1439–1458.

Kumar, D., Verma, H. N., Tuteja, N. & Tewari, K. K. (1997) Plant Mol. Biol. 33, 745–751.

Laemmli, U. K., 1970. Cleavage of structural proteins during the assembly of the head of bacteriophage T4. Nature 227:680–685.

Lawton, K. A., Friedrich, L., Hunt, M., Weymann, K., Delaney, T., Kessmann, H., Staub, T. and Ryals, J., 1996. Benzothiadiazole induces disease resistance in *Arabidopsis* by activation of the systemic acquired resistance signal transduction pathway. Plant J. 10: 71–82.

Lebel, E., Heifetz, P., Thorne, L., Uknes, S., Ryals, J., and Ward, E., 1998. Functional analysis of regulatory sequences controlling PR-1 gene expression in *Arabidopsis*. Plant J. 16: 23–233. León, J., Lawton, M. A., Raskin, I., 1995. Hydrogen peroxide stimulates salicylic acid biosynthesis in tobacco. Plant Physiol. 108: 1673–1678.

Lin, D. and Pawson, T. 1997. Protein molecules in signal transduction, pull-out centrefold. Trends In Cell Biol. 7: 316a–f.

Liu, Y., Zhang, S. and Klessig, D. F. 2000. Molecular cloning and characterization of a tobacco MAP kinase kinase that interacts with SIPK. Mol. Plant-Microbe Interact. 13: 118–124.

Ma, J., Przibilla, E., Hu, J., Bogorad, L., Ptashne, M., 1988. Yeast activators stimulate plant gene expression. Nature 334:631–633.

Malamy, J., Carr, J. P., Klessig, D. F., Raskin, I., 1990. Salicylic acid: a likely endogenous signal in the resistance response of tobacco to viral infection. Science 250: 1002–1004.

Malamy, J., Hennig, J., and Klessig, D. F., 1992. Temperature dependent induction of salicylic acid and its conjugates during the resistance response to tobacco mosaic virus infection. Plant Cell 4: 359–366.

Maldonado, A. M., Cameron, R. K., Doernert, P., Dixon, R. A. and Lamb, C. 2002. DIR1 encodes a putative lipid transfer protein involved in signaling during systemic acquired resistance in *Arabidopsis* thaliana. (2002) Nature 419, 399–403.

McDowell, J. M., Cuzick, A., Can, C., Beynon, J., Dangl, J. L. and Holub, E. B. 2000. Downy mildew *Peronospora parasitica* resistance genes in *Arabidopsis* vary in functional requirements for NDR1, EDS1, NPR1 and salicylic acid accumulation. Plant J. 22: 523–529.

Menke, F. and Klessig, D. F. 2001. Molecular cloning and characterization of a tobacco nuclear-encoded chloroplast protein that interacts with salicylic acid-induced protein kinase (SIPK). 10th Intl. Conf. on MPMI. Abstract 154.

Métraux, J-P., Signer, H., Ryals, J. A., Ward, E., Wyss-Benz, M., Gaudin, J., Raschdorf, K., Schmid, E., Blum, W., Inverardi, B., 1990. Increase in salicylic acid at the onset of systemic acquired resistance in cucumber. Science 250: 1004–1006.

Morris, K., Mackerness, S. A.-H.-, Page, T., John, C. F., Murphy, A. M., Carr, J. P., and Buchanan-Wollaston, V. 2000. Salicylic acid has a role in regulating gene expression during leaf senescence. Plant J 23:677–685.

Morris, S. W., Vernooij, B., Titatarn, S., Starrett, M., Thomas, S., Wiltse, C. C., Frederiksen, R. A., Bhandhufalck, A., Hulbert, S. and Uknes, S., 1998. Induced resistance responses in maize. Mol. Plant Microbe Interact. 11:643–658.

Mou, Z., Fan, W. & Dong, X. (2003) Cell 113, 935–944.

Mur, L. A. J., Naylor, G., Warner, S. A. J., Sugars, J. M., White, R. F. and Draper, J. 1996. Salicylic acid potentiates defence gene expression in tissue exhibiting acquired resistance to pathogen attack. Plant J. 9: 559–571.

Murphy, A. M., Chivasa, S., Singh, D. P. and Carr, J. P., 1999. Salicylic acid-induced resistance to viruses and other pathogens: a parting of the ways? Trends Plant Sci. 4:155–160.

Nakayama, M., Takahashi, R., Johsaki, S., Honda, T., Kiyozumi, M. and Kojima, S. 1984. Effects of aspirin and salicylic acid on lecithin-cholesterol acyltransferase and cholesterol content in rat serum. Biochem. Pharma. 33: 2815–2817.

Nardini, M. and Dijkstra, B. W. 1999. ($\alpha/\beta$ (Hydrolase fold enzymes: the family keeps growing. Curr. Opin. Struct. Biol. 9: 732–737.

Navarre, R., Wendehenne, D., Durner, J., Noad, R. and Klessig, D. F. 2000. Nitric oxide modulates the activity of tobacco aconitase. Plant Physiol. 122: 573–582.

Neuenschwander, U., Vernooij, B., Friedrich, L., Uknes, S., Kessmann, H., and Ryals, J., 1995. Is hydrogen peroxide a second messenger of salicylic acid in systemic acquired resistance. Plant J. 8: 227–233.

Nimchuk, Z., Marois, E., Kjemtrup S., Leister, R. T., Katagiri, F. and Dangl, J. L. 2000. Eukaryotic fatty acylation drives plasma membrane targeting and enhances function of several type III effector proteins from *Pseudomonas syringae*. Cell. 101: 353–363.

Nishizuka, Y., 1986. Studies and perspectives of protein kinase C. Science 233: 305–312.

Oldroyd G. E., and Staskawicz, B. J. 1998. Genetically engineered broad-spectrum disease resistance in tomato. Proc. Natl. Acad. Sci. USA 95: 10300–10305.

Pearce, G. & Ryan, C. A. (2003) J. Biol. Chem. 278, 30044–30050.

Pena-Cortes, H., Albrecht, T., Prat, S., Weiler, E. W., and Willmitzer, L., 1993. Aspirin prevents wound-induced gene-expression in tomato leaves by blocking jasmonic acid. Planta 191: 123–128.

Pillonel, C. 2001. Identification of a 2,6-dichloroisonicotinic-acid-sensitive protein kinase from tobacco by affinity chromatography on benzothiadiazole-sepharose and NIM-metal chelate absorbent. Pest Manag. Sci. 57: 676–682.

Poulton, J. E., 1990. Cyanogenesis in plants. Plant Physiol. 94: 401–405.

Rairdan, G. J. and Delaney, T. P. 2002. Role of salicylic acid and NIM1/NPR1 in race-specific resistance in *Arabidopsis*. Genetics 161: 803–811.

Rasmussen, J. B., Hammerschmidt, R., Zook, M. N., 1991. Systemic induction of salicylic acid accumulation in cucumber after inoculation with *Pseudomonas syringae* pv. syringae. Plant Physiol. 97: 1342–1347.

Ratcliff, F., Harrison, B. D. and Baulcombe, D. C. 1997. A similarity between viral defense and gene silencing in plants. Science 276: 1558–1560.

Ruiz, M. T., Voinnet, O. and Baulcombe, D. C. 1998. Initiation and maintenance of virus-induced gene silencing. Plant Cell 10: 937–946.

Ryals, J., Weymann, K., Lawton, K., Friedrich, L., Ellis, D., Steiner, H.-Y., Johnson, J., Delaney, T. P., Jesse, T., Vos, P. & Uknes, S. (1997) Plant Cell 9, 425–439.

Selmar, D., Carvalho, F. J. and Conn, E. E. 1987. A colorimetric assay for alpha-hydroxynitrile lyase. Anal. Biochem. 166: 208–211.

Shah, J., Kachroo, P. and Klessig, D. F. 1999. The *Arabidopsis* ssi1 mutation restores pathogenesis-related gene expression in npr1 plants and renders defensin gene expression SA dependent. Plant Cell 11: 191–206.

Shah, J., Klessig, D. F., 1996. Identification of a salicylic acid-responsive element in the promoter of the tobacco pathogenisis-related -1,3 glucanase gene, PR-2d. Plant J. 10: 1089–1101.

Shah, J., Tsui, F. and Klessig, D. F. 1997. Characterization of a salicylic acid-insensitive mutant (sai1) of *Arabidopsis thaliana*, identified in a selective screen utilizing the SA-inducible expression of the tms2 gene. Mol. Plant Microbe Interact. 10: 69–78.

Shah, J., Kachroo, P., Nandi, A. & Klessig, D. F. (2001) Plant J. 25, 563–574.

Shan, L, Thara, V. K., Martin, G. B., Zhou, J.-M. and Tang, X. 2000. *Pseudomonas* AvrPto protein is differentially recognized by tomato and tobacco and is localized to the plant plasma membrane. Plant Cell 12: 2323–2338.

Shirano, Y., Kachroo, P., Shah, J. and Klessig, D. F. 2002. A gain-of-function mutation in an *Arabidopsis* TIR-NBS-LRR type R gene triggers defense responses and results in enhanced disease resistance. Plant Cell In review.

Shirasu, K., Nakajima, H., Rajasekhar, V. K., Dixon, R. A., and Lamb, C., 1997. Salicylic acid potentiates an agonist-dependent gain control that amplifies pathogen signals in the activation of defense mechanisms. Plant Cell 9: 261–270.

Silva, H., Yoshioka, K., Dooner, H. K. and Klessig, D. F. 1999. Characterization of a new *Arabidopsis* mutant exhibiting enhanced disease resistance. Mol. Plant-Microbe Interact. 12: 1053–1063.

Slaymaker, D. H., Navarre, D. A. Clark, D., del Poza, O., Martin, G. B. and Klessig, D. F. 2002. The tobacco salicylic acid-binding protein (SABP) 3 is the chloroplast carbonic anhydrase, which exhibits antioxidant activity and plays a role in the hypersensitive defense response. Proc. Natl Acad. Sci. USA. In press.

Smith, N. A., Singh, S. P., Wang, M., Stoutjesdijk, P. A., Green, A. G., and Waterhouse, P. M., 2000. Total splicing by intron-spliced hairpin RNAs. Nature 407: 319–320.

Smith, J. A. and Metraux, J. P., 1991. *Pseudomanas syringae* pv. syringae induces systemic resistance to *Pyricularia oryzae* in rice. Physiol. Molec. Plant Pathol. 39: 451–461.

Spoel, S. H., Koornneef, A., Claessens, S. M. C., Korzelius, J. P., Van Pelt, J. A., Mueller, M. J., Buchala, A. J., Métraux, J. -P., Brown, R., Kazan, K., Van Loon, L. C., Dong, X. & Pieterse, C. M. J. (2003) Plant Cell 15, 760–770.

Summermatter, K., Sticher, L., Métraux, J-P., 1995. Systemic responses in *Arabidopsis thaliana* infected and challenged with *Pseudomonas syringae* pv syringae. Plant Physiol. 108: 1379–1385.

Takahashi, H., Chen, Z., Du, H., Liu, Y., Klessig, D. F., 1997. Development of necrosis and activation of disease resistance in transgenic tobacco plants with severely reduced catalase levels. Plant J. 11: 993–1005.

Tang, X., Xie, M., Kim, Y. J., Zhou, J., Klessig, D. F. & Martin, G. B. (1999) Plant Cell 11, 15–29.

Taniyama, Y., Shibata, S., Kita, S., Horikoshi, K., Fuse, H., Shirafuji, H., Sumino, Y. and Fujino, M. 1999. Cloning and expression of a novel lysophospholipase which structurally resembles lecithin cholesterol acyltransferase. Biochem. Biophys. Res. Comm. 257: 50–56.

Tenhaken, R. and Rübel, C., 1997 Salicylic acid is needed in hypersensitive cell death in soybean but does not act as a catalase inhibitor. Plant Physiol 115 : 291–298.

Van Camp, W., Van Montagu, M., and Inzé, D., 1998. $H_2O_2$ and NO: redox signals in disease resistance. Trends in Plant Sci. 3: 330–334.

Voelkerding, K. V. and Klessig, D. F. 1986. Identification of two nuclear subclasses of the adenovirus type 5 encoded DNA binding protein. J. Virol. 60: 353–362.

Wäspi, U., Misteli, B., Hasslacher, M., Jandrositz, A., Kohlwein, S. D., Schwab, H., and Dudler, R., 1998. The defense-related rice gene Pir7b encodes an alpha/beta hydrolase fold protein exhibiting esterase activity towards naphthol AS-esters. Eur. J. Biochem. 254: 32–37.

Weissmann, G. 1991. Aspirin. Scientific American 264: 84–90.

Wendehenne, D., Durner, J., Chen, Z., and Klessig, D. F. 1998. Benzothiadiazole, an inducer of plant defenses, inhibits catalase and ascorbate peroxidase. Phytochemistry 47: 651–657.

Wesley, S. V., Helliwell, C. A., Smith, N. A., Wang, M. B., Rouse, D. T., Liu, Q., Gooding, P. S., Singh, S. P., Abbott, D., SToutjesdijk, P. A., Robinson, S. P., Gleave, A. P., Green, A. G., and Waterhouse, P. M., 2001. construct design for efficient, effective and high throughput gene silencing n plants. Plant J. 27:581–590.

White, R. F., 1979. Acetylsalicylic acid (aspirin) induces resistance to tobacco mosaic virus in tobacco. Virology 99: 410–412.

Yang J., Koga, Y., Nakano, H. & Yamane, T. (2002) Protein Eng. 15, 147–152.

Yoshioka, K., Kachroo, P., Tsui, F., Sharma, S. B., Shah, J., and Klessig, D. F., 2001. Environmentally-sensitive, SA-dependent defense response in the cpr22 mutant of *Arabidopsis*. Plant J. 26: 447–459.

Zhang, S. and Klessig, D. F. 1997. Salicylic acid activates a 48-kD MAP kinase in tobacco. Plant Cell 9: 809–824.

Zhang, S., and Klessig, D. F. 1998. Resistance gene N-mediated de novo synthesis and activation of a tobacco mitogen-activated protein kinase by tobacco mosaic virus infection. Proc. Natl. Acad. Sci. USA 95: 7433–7438.

Zhong, G. Y., Goren, R., Riov, j., Sisle, E. C. and Holland, D. 2001. Characterization of an ethylene-induced esterase gene isolated from Citrus sinesis by competitive hybridization. Physiol. Plantarum 113: 267–274.

Zhou, N., Tootle, T. L., Tsui, F., Klessig, D. F., and Glazebrook, J., 1998. PAD4 functions upstream from salicylic acid to control defense responses in *Arabidopsis*. Plant Cell 10: 1021–1030.

Zhou, J-M., Trifa, Y., Silva, H., Pontier, D., Lam, E., Shah, J. and Klessig, D. F. 2000. NPR1 differentially interacts with members of the TGA/OBF family of transcription factors that bind an element of the PR-1 gene required for induction by salicylic acid. Mol. Plant-Microbe Interact. 13: 191–202.

Zuo, J., Niu, Q. -W. and Chua, N. -H. 2000. An estrogen receptor-based transactivator XVE mediates highly inducible gene expression in transgenic plants. Plant J. 24: 265–273.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. An isolated SABP2 nucleic acid molecule comprising a nucleotide sequence selected from the group consisting of:
   a) the nucleotide sequence of SEQ ID NO: 2; and
   b) a nucleotide sequence encoding the polypeptide of SEQ ID NO: 2.

2. The isolated nucleic acid molecule of claim 1, wherein said SABP2 nucleic acid molecule comprises SEQ ID NO: 1.

3. The isolated nucleic acid molecule of claim 1, wherein said SABP2 nucleic acid molecule comprises a NUCLE-OTIDE sequence encoding SEQ ID NO: 2.

4. The isolated nucleic acid molecule of claim 1, which is a DNA molecule.

5. An RNA molecule encoded by the SABP2 nucleic acid molecule of claim 1.

6. An expression vector comprising the nucleic acid molecule of claim 1.

7. The expression vector of claim 6 wherein said vector is selected from the group of vectors consisting of plasmid, cosmid, baculovirus, bacteria, yeast and viral vectors.

8. A host cell transformed with the expression vector of claim 6.

9. The host cell of claim 8, wherein said host cell is selected from the group consisting of a plant cell bacterial cell, yeast cell, and insect cell.

10. A method for enhancing resistance of a plant to a plant pathogen comprising transforming the plant with the nucleic acid molecule of claim 1.

11. The method of claim 10, wherein said nucleic acid molecule comprises SEQ ID NO: 1.

12. The method of claim 10, wherein the nucleic acid molecule encodes SEQ ID NO: 2.

13. A transgenic plant comprising the ISOLATED nucleic acid molecule of claim 1.

14. The transgenic plant of claim 13, wherein said plant is TOBACCO.

15. The transgenic plant of claim 13, wherein said plant has increased resistance to disease.

16. The transgenic plant of claim 13 wherein said nucleic acid molecule comprises SEQ ID NO: 1.

17. The transgenic plant of claim 13, wherein the nucleic acid molecule encodes SEQ ID NO: 2.

18. The method of claim 10, wherein said nucleic acid molecule is overexpressed in said plant, and wherein said overexpression enhances the resistance of said plant to a plant pathogen.

19. The host cell of claim 8, wherein said plant cell is from a plant selected from the group consisting of tobacco, *Arabidopsis*, rice, maize, wheat, soybean, tomato, potato, barley, and canola.

20. The method of claim 10, further comprising contacting said plant or a plant cell obtained therefrom with a pathogen responsive agent, and assaying SABP2 function in the presence or absence of said agent in said plant, plant cell or extracts thereof.

* * * * *

SEQUENCE LISTING

<160> NUMBER OF SEQ ID NOS: 58

<210> SEQ ID NO 1
<211> LENGTH: 1079
<212> TYPE: DNA
<213> ORGANISM: Nicotiana tabacum

<400> SEQUENCE: 1

| | | | | | |
|---|---|---|---|---|---|
| acgcggggaa | agaaaagaaa | ctaacaaggc | ataaaattca | aatgaaggaa ggaaaacact | 60 |
| ttgttttagt | acatggtgca | tgccatggag | gttggagttg | gtacaagcta aagccactgc | 120 |
| tagaagctgc | aggccataag | gttacagccc | ttgatttagc | agcttctggc actgatttga | 180 |
| gaaaaataga | ggagcttcgc | acactttatg | attatacttt | gccattgatg gagttgatgg | 240 |
| aatctctttc | agcagatgag | aaggttatat | tagtggggca | tagtcttggt ggtatgaatt | 300 |
| tgggacttgc | tatggaaaag | tatccacaaa | agatctatgc | tgctgttttc ttggctgctt | 360 |
| tcatgcctga | ttctgttcac | aactcctcct | ttgttttgga | acagtataat gagcggacgc | 420 |
| cagccgagaa | ttggttggat | actcagtttt | taccatatgg | ttcccctgaa gagccactga | 480 |
| catccatgtt | ttttggccca | agttcttgg | ctcacaagct | ctaccagcta tgctctcctg | 540 |
| aggatcttgc | attagcatca | tcattggtga | gaccaagctc | tttgtttatg aagacctat | 600 |
| cgaaggccaa | gtatttcaca | gatgaacggt | ttggatcagt | gaagagagtt tacattgtgt | 660 |
| gcactgagga | taaaggcata | ccagaagaat | tccagcgatg | gcaaattgac aacattggtg | 720 |
| tcactgaagc | aatagagatt | aaaggtgctg | atcacatggc | aatgctatgc gagccccaaa | 780 |
| aactttgcgc | ctctctcttg | gaaattgccc | ataaatacaa | ctgatctcta cattatgtct | 840 |
| tcgtctcatg | tcaagatttt | cagtgcatgc | tgtaattttt | ttctattttt cgaccggcgc | 900 |
| ataactgtct | ttgcctattt | taaggattgc | agtaatttca | ctcttctagt gtggaaggct | 960 |
| tccacataag | gattgttctg | tttctccatt | caagtgtgtg | ttatgttgag atacttaaac | 1020 |
| cgtatcaatt | cttgtaatga | aacttcttct | ttccttttg | aaaaaaaaaa aaaaaaaa | 1079 |

<210> SEQ ID NO 2
<211> LENGTH: 260
<212> TYPE: PRT
<213> ORGANISM: Nicotiana tabacum

<400> SEQUENCE: 2

Met Lys Glu Gly Lys His Phe Val Leu Val His Gly Ala Cys His Gly
 1               5                  10                  15

Gly Trp Ser Trp Tyr Lys Leu Lys Pro Leu Leu Glu Ala Ala Gly His
            20                  25                  30

Lys Val Thr Ala Leu Asp Leu Ala Ala Ser Gly Thr Asp Leu Arg Lys
        35                  40                  45

Ile Glu Glu Leu Arg Thr Leu Tyr Asp Tyr Thr Leu Pro Leu Met Glu
    50                  55                  60

Leu Met Glu Ser Leu Ser Ala Asp Glu Lys Val Ile Leu Val Gly His
65                  70                  75                  80

Ser Leu Gly Gly Met Asn Leu Gly Leu Ala Met Glu Lys Tyr Pro Gln
                85                  90                  95

Lys Ile Tyr Ala Ala Val Phe Leu Ala Ala Phe Met Pro Asp Ser Val
            100                 105                 110

His Asn Ser Ser Phe Val Leu Glu Gln Tyr Asn Glu Arg Thr Pro Ala
        115                 120                 125

```
Glu Asn Trp Leu Asp Thr Gln Phe Leu Pro Tyr Gly Ser Pro Glu
    130                 135                 140

Pro Leu Thr Ser Met Phe Phe Gly Pro Lys Phe Leu Ala His Lys Leu
145                 150                 155                 160

Tyr Gln Leu Cys Ser Pro Glu Asp Leu Ala Leu Ala Ser Ser Leu Val
                165                 170                 175

Arg Pro Ser Ser Leu Phe Met Glu Asp Leu Ser Lys Ala Lys Tyr Phe
            180                 185                 190

Thr Asp Glu Arg Phe Gly Ser Val Lys Arg Val Tyr Ile Val Cys Thr
        195                 200                 205

Glu Asp Lys Gly Ile Pro Glu Glu Phe Gln Arg Trp Gln Ile Asp Asn
    210                 215                 220

Ile Gly Val Thr Glu Ala Ile Glu Ile Lys Gly Ala Asp His Met Ala
225                 230                 235                 240

Met Leu Cys Glu Pro Gln Lys Leu Cys Ala Ser Leu Leu Glu Ile Ala
                245                 250                 255

His Lys Tyr Asn
            260

<210> SEQ ID NO 3
<211> LENGTH: 258
<212> TYPE: PRT
<213> ORGANISM: Manihot esculenta

<400> SEQUENCE: 3

Met Ala Val Val Asp Phe Val Leu Ile His Thr Ile Cys His Gly Ala
1               5                   10                  15

Trp Ile Trp Tyr Lys Leu Lys Pro Val Leu Glu Ala Ala Gly His Lys
            20                  25                  30

Val Thr Ala Leu Asp Leu Ala Ala Ser Gly Val Asp Pro Arg Gln Ile
        35                  40                  45

Glu Gln Ile Asn Ser Phe Asp Glu Tyr Ser Glu Pro Leu Leu Thr Phe
    50                  55                  60

Met Glu Ser Leu Pro Gln Gly Glu Lys Val Ile Leu Val Gly Glu Ser
65                  70                  75                  80

Cys Gly Gly Leu Asn Ile Ala Ile Ala Ala Asp Lys Tyr Pro Glu Lys
                85                  90                  95

Ile Ala Ala Ala Val Phe Gln Asn Ser Leu Leu Pro Asp Thr Lys His
            100                 105                 110

Lys Pro Ser Tyr Val Val Asp Lys Leu Met Glu Val Phe Pro Asp Trp
        115                 120                 125

Lys Asp Thr Glu Tyr Phe Glu Phe Ser Asn Ser Asn Gly Glu Thr Ile
    130                 135                 140

Thr Gly Met Val Leu Gly Leu Lys Leu Met Arg Glu Asn Leu Tyr Thr
145                 150                 155                 160

Ile Cys Pro Pro Glu Asp Tyr Glu Leu Ala Lys Met Leu Thr Arg Arg
                165                 170                 175

Gly Ser Leu Phe Gln Ser Ile Leu Ala Gln Arg Glu Lys Phe Thr Glu
            180                 185                 190

Lys Gly Tyr Gly Ser Ile Lys Lys Ile Tyr Val Trp Thr Gly Asp Asp
        195                 200                 205

Lys Ile Phe Leu Pro Glu Phe Gln Leu Trp Gln Ile Glu Asn Tyr Lys
    210                 215                 220

Pro Asp Leu Val Phe Arg Val Met Gly Gly Asp His Lys Leu Gln Leu
```

```
                225                 230                 235                 240
Thr Lys Thr Asn Glu Ile Ala Gly Ile Leu Gln Lys Val Ala Asp Ile
                    245                 250                 255

Tyr Ala

<210> SEQ ID NO 4
<211> LENGTH: 257
<212> TYPE: PRT
<213> ORGANISM: Hevea brasiliansis

<400> SEQUENCE: 4

Met Ala Phe Ala His Phe Val Leu Ile His Thr Ile Cys His Gly Ala
  1               5                  10                  15

Trp Ile Trp His Lys Leu Lys Pro Leu Leu Glu Ala Leu Gly His Lys
                 20                  25                  30

Val Thr Ala Leu Asp Leu Ala Ala Ser Gly Val Asp Pro Arg Gln Ile
             35                  40                  45

Glu Glu Ile Gly Ser Phe Asp Glu Tyr Ser Glu Pro Leu Leu Thr Phe
 50                  55                  60

Leu Glu Ala Leu Pro Pro Gly Glu Lys Val Ile Leu Val Gly Glu Ser
65                  70                  75                  80

Cys Gly Gly Leu Asn Ile Ala Ile Ala Ala Asp Lys Tyr Cys Glu Lys
                 85                  90                  95

Ile Ala Ala Ala Val Phe His Asn Ser Val Leu Pro Asp Thr Glu His
                100                 105                 110

Cys Pro Ser Tyr Val Val Asp Lys Leu Met Glu Val Phe Pro Asp Trp
            115                 120                 125

Lys Asp Thr Thr Tyr Phe Thr Tyr Thr Lys Asp Gly Lys Glu Ile Thr
        130                 135                 140

Gly Leu Lys Leu Gly Phe Thr Leu Leu Arg Glu Asn Leu Tyr Thr Leu
145                 150                 155                 160

Cys Gly Pro Glu Glu Tyr Glu Leu Ala Lys Met Leu Thr Arg Lys Gly
                165                 170                 175

Ser Leu Phe Gln Asn Ile Leu Ala Lys Arg Pro Phe Phe Thr Lys Glu
                180                 185                 190

Gly Tyr Gly Ser Ile Lys Lys Ile Tyr Val Trp Thr Asp Gln Asp Glu
            195                 200                 205

Ile Phe Leu Pro Glu Phe Gln Leu Trp Gln Ile Glu Asn Tyr Lys Pro
        210                 215                 220

Asp Lys Val Tyr Lys Val Glu Gly Gly Asp His Lys Leu Gln Leu Thr
225                 230                 235                 240

Lys Thr Lys Glu Ile Ala Glu Ile Leu Gln Glu Val Ala Asp Thr Tyr
                245                 250                 255

Asn

<210> SEQ ID NO 5
<211> LENGTH: 263
<212> TYPE: PRT
<213> ORGANISM: Arabidopsis thaliana

<400> SEQUENCE: 5

Met Ser Glu Glu Lys Arg Lys Gln His Phe Val Leu Val His Gly Ser
  1               5                  10                  15

Cys His Gly Ala Trp Cys Trp Tyr Lys Val Lys Pro Leu Leu Glu Ala
                 20                  25                  30
```

Val Gly His Arg Val Thr Ala Val Asp Leu Ala Ala Ser Gly Ile Asp
        35                  40                  45

Thr Thr Arg Ser Ile Thr Asp Ile Pro Thr Cys Glu Gln Tyr Ser Glu
 50                  55                  60

Pro Leu Thr Lys Leu Leu Thr Ser Leu Pro Asn Asp Glu Lys Val Val
 65                  70                  75                  80

Leu Val Gly His Ser Phe Gly Gly Leu Asn Leu Ala Ile Ala Met Glu
                 85                  90                  95

Lys Phe Pro Glu Lys Ile Ser Val Ala Val Phe Leu Thr Ala Phe Met
            100                 105                 110

Pro Asp Thr Glu His Ser Pro Ser Phe Val Leu Asp Lys Phe Gly Ser
            115                 120                 125

Asn Met Pro Gln Glu Ala Trp Met Gly Thr Glu Phe Glu Pro Tyr Gly
130                 135                 140

Ser Asp Asn Ser Gly Leu Ser Met Phe Phe Ser Pro Asp Phe Met Lys
145                 150                 155                 160

Leu Gly Leu Tyr Gln Leu Ser Pro Val Glu Asp Leu Glu Leu Gly Leu
                165                 170                 175

Leu Leu Met Arg Pro Gly Ser Leu Phe Ile Asn Asp Leu Ser Lys Met
            180                 185                 190

Lys Asn Phe Ser Asp Glu Gly Tyr Gly Ser Val Pro Arg Val Phe Ile
            195                 200                 205

Val Cys Lys Glu Asp Lys Ala Ile Pro Glu Glu Arg Gln Arg Trp Met
210                 215                 220

Ile Asp Asn Phe Pro Val Asn Leu Val Met Glu Met Glu Glu Thr Asp
225                 230                 235                 240

His Met Pro Met Phe Cys Lys Pro Gln Gln Leu Ser Asp Tyr Phe Leu
                245                 250                 255

Lys Ile Ala Asp Lys Phe Val
            260

<210> SEQ ID NO 6
<211> LENGTH: 268
<212> TYPE: PRT
<213> ORGANISM: Rice

<400> SEQUENCE: 6

Met Glu Ile Ser Ser Ser Ser Lys Lys His Phe Ile Leu Val His Gly
 1               5                  10                  15

Leu Cys His Gly Ala Trp Cys Trp Tyr Arg Val Val Ala Ala Leu Arg
                 20                  25                  30

Ala Ala Gly His Arg Ala Thr Ala Leu Asp Met Ala Ala Ser Gly Ala
            35                  40                  45

His Pro Ala Arg Val Asp Glu Val Gly Thr Phe Glu Glu Tyr Ser Arg
 50                  55                  60

Pro Leu Leu Asp Ala Val Ala Ala Ala Ala Pro Gly Glu Arg Leu
 65                  70                  75                  80

Val Leu Val Gly His Ser His Gly Gly Leu Ser Val Ala Leu Ala Met
                 85                  90                  95

Glu Arg Phe Pro Asp Lys Val Ala Ala Val Phe Val Ala Ala Ala
            100                 105                 110

Met Pro Cys Val Gly Lys His Met Gly Val Pro Thr Glu Glu Phe Met
            115                 120                 125

Arg Arg Thr Ala Pro Glu Gly Leu Leu Met Asp Cys Glu Met Val Ala
130                 135                 140

```
Ile Asn Asn Ser Gln Gly Ser Gly Val Ala Ile Asn Leu Gly Pro Thr
145                 150                 155                 160

Phe Leu Ala Gln Lys Tyr Tyr Gln Gln Ser Pro Ala Glu Asp Leu Ala
                165                 170                 175

Leu Ala Lys Met Leu Val Arg Pro Gly Asn Gln Phe Met Asp Asp Pro
            180                 185                 190

Val Met Lys Asp Glu Ser Leu Leu Thr Asn Gly Asn Tyr Gly Ser Val
        195                 200                 205

Lys Lys Val Tyr Val Ile Ala Lys Ala Asp Ser Ser Thr Glu Glu
    210                 215                 220

Met Gln Arg Trp Met Val Ala Met Ser Pro Gly Thr Asp Val Glu Glu
225                 230                 235                 240

Ile Ala Gly Ala Asp His Ala Val Met Asn Ser Lys Pro Arg Glu Leu
                245                 250                 255

Cys Asp Ile Leu Ile Lys Ile Ala Asn Lys Tyr Glu
            260                 265

<210> SEQ ID NO 7
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: variation
<222> LOCATION: (0)...(0)
<223> OTHER INFORMATION: n at position 3 is a or t, n at position 6 is a
      or g, n at position 9 is c or t, n at position 12 is a or g, n at
      position 15 is a or c or t, n at position 18 is c or t

<400> SEQUENCE: 7
acncanttnt tnccntangg                                              20

<210> SEQ ID NO 8
<211> LENGTH: 7
<212> TYPE: PRT
<213> ORGANISM: Artificial Sequence
<220> FEATURE:
<223> OTHER INFORMATION: Encoded by primer

<400> SEQUENCE: 8

Thr Gln Phe Leu Pro Tyr Gly
1               5

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
gactcgagtc gacatcga                                                18

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
agagatcagt tgtatttatg                                              20
```

-continued

```
<210> SEQ ID NO 11
<211> LENGTH: 14
<212> TYPE: PRT
<213> ORGANISM: Nicotiana Tabacum

<400> SEQUENCE: 11

Val Thr Ala Leu Asp Leu Ala Ala Ser Gly Thr Asp Leu Arg
 1               5                  10

<210> SEQ ID NO 12
<211> LENGTH: 12
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 1 can be any amino acid.

<400> SEQUENCE: 12

Xaa Thr Ala Leu Asp Leu Ala Ala Ser Gly Thr Asp
 1               5                  10

<210> SEQ ID NO 13
<211> LENGTH: 14
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 2 can be any amino acid.

<400> SEQUENCE: 13

Val Xaa Ala Leu Asp Leu Ala Ala Ser Gly Ile Asp Leu Arg
 1               5                  10

<210> SEQ ID NO 14
<211> LENGTH: 15
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 6 can be Tryptophan or
      Isoleucine.

<400> SEQUENCE: 14

Thr Pro Ala Glu Asn Xaa Leu Asp Thr Gln Phe Leu Pro Tyr Gly
 1               5                  10                  15

<210> SEQ ID NO 15
<211> LENGTH: 15
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 11 can be Phenylalanine or
      Glutamic Acid.
      Xaa at position 13 can be Methionine or Proline

<400> SEQUENCE: 15

Thr Pro Ala Glu Asn Thr Leu Asp Thr Gln Xaa Leu Xaa Tyr Gly
 1               5                  10                  15

<210> SEQ ID NO 16
<211> LENGTH: 14
<212> TYPE: PRT
```

```
<213> ORGANISM: Nicotiana Tabacum
<220> FEATURE:
<221> NAME/KEY: VARIANT
<222> LOCATION: (0)...(0)
<223> OTHER INFORMATION: Xaa at position 1 can be any amino acid.

<400> SEQUENCE: 16

Xaa Pro Ala Glu Asn Trp Leu Asp Thr Gln Phe Leu Pro Tyr
 1               5                  10

<210> SEQ ID NO 17
<211> LENGTH: 10
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 4 is preferably Glutamic Acid
      or Asparagine, but can be any amino acid.
<220> FEATURE:
<221> NAME/KEY: VARIANT
<222> LOCATION: (0)...(0)
<223> OTHER INFORMATION: Xaa at position 6 is preferably Leucine or
      Glycine, but can be any amino acid.
<220> FEATURE:
<221> NAME/KEY: VARIANT
<222> LOCATION: (0)...(0)
<223> OTHER INFORMATION: Xaa at position 8 is preferaly Serine or
      Threonine, but can be any amino acid.

<400> SEQUENCE: 17

Tyr Pro Glu Xaa Pro Xaa Thr Xaa Met Phe
 1               5                  10

<210> SEQ ID NO 18
<211> LENGTH: 11
<212> TYPE: PRT
<213> ORGANISM: Nicotiana Tabacum

<400> SEQUENCE: 18

His Tyr Ala Leu Phe Met Glu Asp Leu His Lys
 1               5                  10

<210> SEQ ID NO 19
<211> LENGTH: 8
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 2 can be Glutamine or Lysine.

<400> SEQUENCE: 19

Ala Xaa Tyr Phe Thr Asp Glu Arg
 1               5

<210> SEQ ID NO 20
<211> LENGTH: 6
<212> TYPE: PRT
<213> ORGANISM: Nicotiana Tabacum

<400> SEQUENCE: 20

Tyr Phe Gln Asp Glu Arg
 1               5

<210> SEQ ID NO 21
<211> LENGTH: 10
<212> TYPE: PRT
<213> ORGANISM: Nicotiana Tabacum
```

```
<400> SEQUENCE: 21

Leu Val Pro Val Asp Val Ser Ile Asp Pro
1               5                   10

<210> SEQ ID NO 22
<211> LENGTH: 10
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 1 is preferably Isoleucine or
      Tyrosine, but can be any amino acid.

<400> SEQUENCE: 22

Xaa His Phe Tyr Ile Tyr Pro Leu Asn Ser
1               5                   10

<210> SEQ ID NO 23
<211> LENGTH: 11
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 1 is preferably Phenylalnine or
      Tyrosine but can be any amino acid.
<220> FEATURE:
<221> NAME/KEY: VARIANT
<222> LOCATION: (0)...(0)
<223> OTHER INFORMATION: Xaa at position 2 is preferably Serine or
      Alanine but can be any amino acid.
<220> FEATURE:
<221> NAME/KEY: VARIANT
<222> LOCATION: (0)...(0)
<223> OTHER INFORMATION: Xaa at position 8 is preferably Aspartic Acid
      or Phenylalanine but can be any amino acid.
<220> FEATURE:
<221> NAME/KEY: VARIANT
<222> LOCATION: (0)...(0)
<223> OTHER INFORMATION: Xaa at position 9 is preferably Glycine or
      Phenylalnine but can be any amino acid.

<400> SEQUENCE: 23

Xaa Xaa Leu Tyr Asp Phe Val Xaa Xaa His Lys
1               5                   10

<210> SEQ ID NO 24
<211> LENGTH: 10
<212> TYPE: PRT
<213> ORGANISM: Nicotiana Tabacum

<400> SEQUENCE: 24

Tyr Val Thr Pro Glu Asn Asn Leu Tyr Phe
1               5                   10

<210> SEQ ID NO 25
<211> LENGTH: 10
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 1 is preferably Isoleucine or
      Serine but can be any amino acid.
<220> FEATURE:
<221> NAME/KEY: VARIANT
<222> LOCATION: (0)...(0)
<223> OTHER INFORMATION: Xaa at position 6 is preferably Serine or
      Glutamine but can be any amino acid.
```

```
<220> FEATURE:
<221> NAME/KEY: VARIANT
<222> LOCATION: (0)...(0)
<223> OTHER INFORMATION: Xaa at position 7 is preferably Phenylalnine or
      Isoleucine but can be any amino acid.

<400> SEQUENCE: 25

Xaa Asp Tyr His Ile Xaa Xaa Glu Glu Leu
  1               5                  10

<210> SEQ ID NO 26
<211> LENGTH: 11
<212> TYPE: PRT
<213> ORGANISM: Nicotiana Tabacum

<400> SEQUENCE: 26

Asn Ser Ile Gln Pro Asp Phe Tyr Ala Asn Lys
  1               5                  10

<210> SEQ ID NO 27
<211> LENGTH: 12
<212> TYPE: PRT
<213> ORGANISM: Nicotiana Tabacum

<400> SEQUENCE: 27

Asp Ile Asp Gly Val Pro Glu Thr Leu Asp Leu Arg
  1               5                  10

<210> SEQ ID NO 28
<211> LENGTH: 6
<212> TYPE: PRT
<213> ORGANISM: Nicotiana Tabacum

<400> SEQUENCE: 28

Gly Ala Cys His Gly Gly
  1               5

<210> SEQ ID NO 29
<211> LENGTH: 4
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at position 3 can be any amino acid.

<400> SEQUENCE: 29

Gly Ser Xaa Gly
  1

<210> SEQ ID NO 30
<211> LENGTH: 5
<212> TYPE: PRT
<213> ORGANISM: Nicotiana Tabacum
<220> FEATURE:
<221> NAME/KEY: VARIANT
<222> LOCATION: (0)...(0)
<223> OTHER INFORMATION: Xaa at positions 2 and 4 can be any amino acid.

<400> SEQUENCE: 30

Ala Xaa Ser Xaa Gly
  1               5

<210> SEQ ID NO 31
<211> LENGTH: 6901
<212> TYPE: DNA
<213> ORGANISM: Homo Sapien
```

<400> SEQUENCE: 31

| | | | | |
|---|---|---|---|---|
| ctgcagacat | ggagttcctc | gaggtgctga | ccgagggcct | tgagcgggtg | ctgttggtgc | 60 |
| gcggtggtgg | ccgtgaagtc | atcaccatct | actcctgagc | ccagtgtcat | cttgtggcct | 120 |
| ggagtcgagg | tcttggccag | gacataacaa | gctgtggtct | ggggtaacag | cctcttccca | 180 |
| gcacccacct | gccagccctg | cttgcctggc | cctgtcctgg | acccagcttt | gctaggtctc | 240 |
| cttggaaacc | aggcctgggc | tcaaaatgg | agatggatcc | caggtcttgt | gggaccctgg | 300 |
| gatgtttggg | gactttacta | tctagcaccc | cagtaggcct | gtcctggcca | gagaagactg | 360 |
| gtaggggccg | agtgggttt | aaggcagcc | ggcccggccc | agcccaggag | cgctatttat | 420 |
| tgcatattta | ttgtttggat | gtcaccatca | gagacgaagg | gaagggtagc | caggagggga | 480 |
| gtccagccca | gctgcctgca | ggaagatctg | gctcagtcta | ctatgggcag | ggccccccac | 540 |
| caagctgagc | cgaatggaga | cagctgagct | gaggcctgac | tttttcaata | aacattgtg | 600 |
| tagttctggg | cctcctgctg | ccccggctct | gtttcccctg | gcgccaagag | aagaaggcgg | 660 |
| aactgaaccc | aggcccagag | ccggctccct | gaggctgtgc | cccttccgg | caatctctgg | 720 |
| ccacaacccc | cactggccag | gccgtccctc | ccactggccc | tagggcccct | cccactccca | 780 |
| caccagataa | ggacagccca | gtgccgcttt | ctctggcagt | aggcaccagg | gctggaatgg | 840 |
| ggccgcccgg | ctccccatgg | cagtgggtga | cgctgctgct | ggggctgctg | ctccctcctg | 900 |
| ccgcccctt | ctggctcctc | aatgtgctct | tcccccgca | caccacgccc | aaggctgagc | 960 |
| tcagtaacca | cacacggccc | gtcatcctcg | gtaagccccc | accaggcccc | tgatgcacca | 1020 |
| cgccagaccc | tggggagcct | gggccccagc | ccctggcagc | tgacctggcc | aaagcccttc | 1080 |
| tgccctgcat | aagcccgac | ataagtacct | gccctggtgt | ggggagggc | caaaagcttg | 1140 |
| tcccttagag | gaatgacgtc | ccttctccca | ccacactgtg | actctcagtt | gtctaaccca | 1200 |
| ggggggcgga | gtgggggacg | gggtgtgcct | gaggtcttgg | ctggggcatc | acaagctgtg | 1260 |
| gtcagtcaca | gccacaccag | actctgggcc | aagcccacca | ctccttcctt | ggcccccacc | 1320 |
| caccaaggac | aagatgccca | gcccaggatc | ggtgagcagg | agaggcccat | ccatgcccgg | 1380 |
| cccctattag | gcccagcccc | catgccccca | gacctatctg | ttcccacctt | ggactttggc | 1440 |
| aataaaggag | cgccagactg | ggtgtttgct | ctgcagaggc | aggggtcagc | ggccttggcc | 1500 |
| tcagcacctc | agcgccttcc | cttcctcagg | gaagcctggg | ctttggctac | tgggggggaca | 1560 |
| gcagggagag | ggggtgtaag | caggggaggg | taagtgtgct | ttgtacctgg | gggttgaggg | 1620 |
| tatgggaggt | ggggggtggg | tctggtcact | gcagcatctg | gggtgacggg | ggtaagggtc | 1680 |
| acgggggaa | tccagagtcc | agagtgaggg | ctgctgctca | cagtgcccgg | ctgcctgggg | 1740 |
| aatcagctag | aagccaagct | ggacaaacca | gatgtggtga | actggatgtg | ctaccgcaag | 1800 |
| acagaggact | tcttcaccat | ctggctggat | ctcaacatgt | tcctacccct | tggggtagac | 1860 |
| tgctggatcg | ataacaccag | gtacagccat | gtgctccacc | ctagcccaa | cacgctgccc | 1920 |
| cttggctact | ggctgctgag | tggcaccccc | gcccgcagg | gttgtctaca | accggagctc | 1980 |
| tgggctcgtg | tccaacgccc | ctggtgtcca | gatccgcgtc | cctggctttg | gcaagaccta | 2040 |
| ctctgtggag | tacctggaca | gcagcaagct | ggcaggtttg | tgtcagaggg | cagggctggg | 2100 |
| gctccaggcc | tgggtgctgg | cccacagcag | gcatggccca | agccccggt | gctgctggtc | 2160 |
| cccccacagg | gtacctgcac | acactggtgc | agaacctggt | caacaatggc | tacgtgcggg | 2220 |
| acgagactgt | gcgcgccgcc | ccctatgact | ggcggctgga | gcccgtgag | tgtctctgcg | 2280 |

-continued

```
gatgaccggc ttggggtggg gcaggtgccc cagaccccag ctgccctgac cccttccacc    2340
cgctgcaggc cagcaggagg agtactaccg caagctcgca gggctggtgg aggagatgca    2400
cgctgcctat gggaagcctg tcttcctcat tggccacagc ctcggctgtc tacacttgct    2460
ctatttcctg ctgcgccagc cccaggcctg gaaggaccgc tttattgatg gcttcatctc    2520
tcttggggct ccctgggtg gctccatcaa gcccatgctg gtcttggcct caggtgagaa    2580
ggcctcgaac acttaggtcc agcgatgggt gagaccaagc tgatcctggg cctgccttca    2640
ttgcggctcc tgctcacagt ggcctctagg ggtgctatct accactcctg ggctggcatg    2700
cttgctgtca ctgcccccca gagcagtgac cctggcctga gcaattaggg tggctccttc    2760
cagagtctgt gtcagtgatg gcaaaggggc agtgaacaca gaaagtgaat cccagctatc    2820
tgctcccagg gtttgttctt gtagcccag agcctgcctg cccagccctt gcctgccttc    2880
cacttgctcg caggagtgcc tttgcccagg gatgtgcttc actgaggatg gatctgccag    2940
agctagggcc agaccccccg aggccccacc tgctcttccc tagggagtgg caccagggcc    3000
cagcactgac acagctacca cctactcccc accccctgta ccctgggagc tggtctggag    3060
agagaaacac agtctggaca agagaaacgc tcatcagaca ccaccaataa acatcaaaca    3120
gacaccatct tgtttccccc tttctggagc acaactctgt ggcccccatt gctgcataag    3180
ccacacaagg agcagaaaga cacatgcccg agggaggaca gccagcaccg cccccaccat    3240
ccccacacat cctgggcctc acccaccatc cccacacacc ctggtcctca ggaagccccg    3300
cctacttttt ttttttctttt tcagacaggg tcattctgtc gcccaggctg gagtgcagtg    3360
gcgtgatcat agccgcagtc tcaatctccc tggcccaagc aatcctcctg cctcagcctc    3420
ctggttagct gagactatag gcacacaaca ccacacctaa tttattttg tttttttagta    3480 gagatgaggt cttgctatgt tgcccaggct ggtctcaaac tcttcacctt aagtgatctt    3540
cctgcctcag cctcccgaag tgctgggatt acaggcgtga gctactgtgc tgggcctttt    3600
aaaaaatgtt tatttgttta tttatgtatt ttgagatgga gtctcgctct gtttcccagg    3660
ctggagtgca gtagtgcaat ctccactcac tgcaacctcc atctccccag ttcaagtgat    3720
tcttctgcct cagcctccct agtagctagg atcacaggca tgtgccacca cgcctggcta    3780 attttttatat ttttagtaga gattaggttt ccccatgttg gccaggctgg tctcgaactc    3840
ctgaccttaa gtcatctgcc tgcctcggcc tcccaaagtg ctaggattac aggtgtgagc    3900
caccgtaccc ggccctattt atttattttt taagctggaa tctcactgtg tcacccaggc    3960
tacagtgcag tggtgcgatc atagtttact gtaacctcaa attcctaggc tcaagcaatc    4020
ttcctgcctt tgcctcctga gtagctagga ctagaggtgc actccactaa gcccagctga    4080
tttttttttt ttttttttt gtagagacag ggtctcactg cattgcctag tctggtcacg    4140
gactcctggc ctcaagtgat cctcctgcct cagcctccca agtgttggg attacagggg    4200 tgagccatgg tgcctgtccc tgccatcctt ttgaagccct acagtccac caacagagg    4260 tcttatcagg gcttctcatt gagtaagctg acactgagca tcattgaata tcaggcctgc    4320
tcaagcctgt ggcttagagt ctgtgtctag attgggcagg acaagattg agcatctggc    4380 tgagcctaca ctcagcaggt tgtgggccag gggtagccag gcctggctcc ctgtcccacc    4440
ttgctccata tccacaggtg acaaccaggg catcccatc atgtccagca tcaagctgaa    4500
agaggagcag cgcataacca ccacctcccc ctggatgttt ccctctcgca tggcgtggcc    4560
tgaggaccac gtgttcattt ccacacccag cttcaactac acaggccgtg acttccaacg    4620 cttcttttgca gacctgcact ttgaggaagg ctggtacatg tggctgcagt cacgtgacct    4680
```

```
cctggcagga ctcccagcac ctggtgtgga agtatactgt ctttacggcg tgggcctgcc    4740
cacgccccgc acctacatct acgaccacgg cttccctac  acggaccctg tgggtgtgct    4800
ctatgaggat ggtgatgaca cggtggcgac ccgcagcacc gagctctgtg cctgtggca    4860
gggccgccag ccacagcctg tgcacctgct gcccctgcac gggatacagc atctcaacat    4920
ggtcttcagc aacctgaccc tggagcacat caatgccatc ctgctgggtg cctaccgcca    4980
gggtcccccct gcatccccga ctgccagccc agagcccccg cctcctgaat aaagaccttc   5040
ctttgctacc gtaagccctg atggctatgt ttcaggttga agggaggcac tagagtccca    5100
cactaggttt cactcctcac cagccacagg ctcagtgctg tgtgcagtga ggcaagatgg    5160
gctctgctga ggcctgggac tgagctgggc accctagatg tacagctgcc cactctcctg    5220
gtcgagctgt tgaggcagtg tgcaccgtgc ctgcctctgt gctgggcgcg gggactggag    5280
ctggctccac ccacagccct gtcagaggag cacggggcgg tgggggggcg gtgacaattt    5340
gagctgtctc tcccagctcc caaaagggca ggtgagacga ccttttgagt gctgggtgaa    5400
tgacagggcc acaagtgttt agaggccggg cacggtggct cacgcctgta atcctggcac    5460
tttgggagac cgaggcaggc ggatcacctg aactcaggag tttgagacca gccaggccaa    5520
catggcagaa accccgtct ctactaaaat acaaaatatt tgccaggcgt ggtggcatgc     5580
atctgtcgtc ccagctactc aggaggctga ggcacgagaa tcatttgaac ctgggaggtg    5640
aggtcactgt gagccgagat cacgtcgttg cactccagac tgggcggcag aatgagactg    5700
tctcaaaaaa aaagagactg ggtctcaaaa aaaaaaaaa aaaaaaagt tagaattaaa       5760
atctgggagt gacaaccatt aatcagatca tttcactaat ggaagtttaa ttactaatga    5820
agctaaatgc tctgagaaaa gcttaggaag cacaagaggc tgagcctttc aggtcagcaa    5880
agacttccca gaggaggcag tgcctacact gaggtcagag tgacaagaag agtaatggac    5940
cactgtaaag acttgggttc ggccgggcgc ggtggctcac gcctgtaatc ccagcacttt    6000
gggaggccga ggcgggtgga tcatgaggtc aggagatcga gaccatcctg gctaacaagg    6060
tgaaaccccg tctctactaa aaatacagaa aattagccgg gcgcggtggc gggcgcctgt    6120
ggtcccagct actcgggagg ctgaggcagg agaatggcgt gaacccggga gcggagctt    6180
gcagtgagcc gagattgcgc cactgcagtc cgcagtccgg cctgggcgac agagcgagac    6240
tccgtctcaa aaaaaaaaa  agacttgggt tgacttgat  tgagcccagg agttcgagac    6300
aagcctgggc aatatagtga gacctcatct ctacaaaat  tttaaaaatt agccggtgc     6360
ggtggctcat gcctgtaatc ccagcactct gggaggccga ggtgggcgga tcacttgagg    6420
tcagaagttt gagaccaccc tgaccaacat ggagaaaccc cgtctctact aaaaatacaa    6480
aattagccgg gcatggtggc gcatgcctgt aatcccagct actcgggagg ctgaggcagg    6540
agaattgttt gaacctggga ggtggacgtt gcggtgagcc aagatcacac tattgcactc    6600
cagcctgggc aacaagagca aaactccgtc tcaaaaaaaa aaatttattt ttaaattagc    6660
caggtgtagc cacagctgta gtcaaatcta ctaggcaggc tgaggtggga ggattgcttg    6720
aacctgggag gcagaggttg cagtgagcca agatggtgcc acggcattcc agcctgagca    6780
acagcaagac cctgtgtcca aaaaaaaaa  aaaaaaaac  cgtaaaatag gccaggcaca    6840
gtggttcatg gttataagcc tagcactttg gaaggctgag gagggtggat cgcctgagct    6900
c                                                                    6901
```

<210> SEQ ID NO 32

<211> LENGTH: 989
<212> TYPE: DNA
<213> ORGANISM: Arabidopsis Thaliana

<400> SEQUENCE: 32

| | |
|---|---:|
| aagcgacaat tatttttttc cagaacattt acctataaaa tctttctact tatatttgtc | 60 |
| tgcgtgtgac ttttaggaga gtaagaaaat atcgaaggtc agaagaatga gtgaggaaaa | 120 |
| gaggaaacaa cattttgtac tagtacatgg ttcgtgccat ggcgcgtggt gctggtacaa | 180 |
| ggttaagccg ctgctagagg cggtgggcca ccgcgtaact gctgtggact tagctgcctc | 240 |
| cggaatagac acaacgaggt cgatcactga catccccaca tgcgaacaat actcggagcc | 300 |
| attgacgaag ctcctgacct cattgccaaa tgatgaaaag gttgtgctcg ttggtcacag | 360 |
| ctttggtggc ttgaacttag ccatagccat ggaaaagttt cccgaaaaaa tctctgtcgc | 420 |
| tgtattcttg actgctttca tgccggacac cgaacactca ccatccttcg tcttggacaa | 480 |
| gtttggaagc aacatgcctc aagaagcatg gatgggcacc gaattcgaac cttatggttc | 540 |
| agacaattcc ggactgagta tgttttttag ccctgacttc atgaagttgg gtctctacca | 600 |
| gctttctcca gttgaggatc ttgaactggg attactttta atgaggccag gatcgttatt | 660 |
| tattaacgat ttatcgaaga tgaaaaactt ctcggatgaa ggatatgggt ctgttcctcg | 720 |
| agttttcata gtgtgtaaag aggacaaagc aattccagaa gaacgccaga gatggatgat | 780 |
| tgataatttt ccggtgaatt tagtgatgga gatggaggag acagatcata tgccaatgtt | 840 |
| ctgcaagcct cagcaactca gtgattactt cctgaaaatc gcggacaaat tcgtttaatc | 900 |
| aaatcttcat gaaactgtat tggatttgat ataataaagg tttgttgcaa atgaattaat | 960 |
| aatgatgaat atttttaaat ttcaggctt | 989 |

<210> SEQ ID NO 33
<211> LENGTH: 870
<212> TYPE: DNA
<213> ORGANISM: Arabidopsis Thaliana

<400> SEQUENCE: 33

| | |
|---|---:|
| aaaaagtacg aaaggaaaat atgagtgagg agaagaggaa gcaacacttc gtgctagtac | 60 |
| atggtgcgtg ccacggcgca tggtgctggt acaaggttaa gcctcttctc gaggctttgg | 120 |
| gccatcgtgt aaccgcctta gacctagctg cttccggtat agacacaacc aggtcaatca | 180 |
| ctgacatttc tacatgtgaa caatattctg agccattgat gcagctaatg acttcattgc | 240 |
| cgaatgatga gaaggttgta ctcgttggtc atagctttgg aggtttgagt ttagccttag | 300 |
| ccatggataa gtttcccgat aaaatctctg tctctgtctt cgtgactgca ttcatgcccg | 360 |
| acaccaaaca ctcaccatcg ttcgtcgagg aaaagtttgc aagcagcatg acaccagaag | 420 |
| gatggatggg ctctgagctc gagacatatg gttcagataa ttccggcttg tctgtgttct | 480 |
| tcagcaccga cttcatgaag caccgtctct accaactttc tcctgtggag gatcttgagc | 540 |
| ttggattgct tctaaagagg cctagttcat tgtttattaa tgaattatcg aagatggaga | 600 |
| acttttctga gaaagggtat ggatctgttc ctcgagctta cattgtgtgc aaagaggaca | 660 |
| acattatctc ggaagaccat caacgatgga tgatccataa ttatccggcg aatttagtga | 720 |
| ttgagatgga agagactgat catatgccaa tgttttgcaa acctcaacta ctaagtgacc | 780 |
| atctattggc aatcgctgac aatttctgtt aaataatatt ttgatgaaaa tgtatttgga | 840 |
| gtggatacaa tcaaacgtgt tctaaaatgg | 870 |

<210> SEQ ID NO 34
<211> LENGTH: 837
<212> TYPE: DNA
<213> ORGANISM: Arabidopsis Thaliana

<400> SEQUENCE: 34

| | | | | | | |
|---|---|---|---|---|---|---|
| tgaagagtaa | gaagtcgaga | gacaaagtta | aagtagaga | agaaaatgag | tgaggaggag | 60 |
| aggaagcaac | acgtcgttct | agtacatggt | gcttgccatg | gcgcctggtg | ctggtacaag | 120 |
| gttaagccgc | agctcgaggc | ttctggccac | cgcgtaaccg | ccgtagatct | agctgcctcc | 180 |
| ggtatagaca | tgaccaggtc | aatcacagat | atatccacat | gcgaacaata | ctcagagcca | 240 |
| ttgatgcagc | taatgacctc | actaccagat | gatgagaagg | ttgtgcttgt | tggtcatagc | 300 |
| ttaggaggtt | tgagtttagc | tatggccatg | gatatgtttc | cgaccaaaat | ctctgtttct | 360 |
| gtctttgtga | ctgctatgat | gccagacacc | aaacactcac | catccttcgt | atgggataag | 420 |
| ctaagaaaag | aaacttcacg | agaggaatgg | ttagacaccg | tgtttacgag | cgagaaacct | 480 |
| gattttccta | gcgagttttg | gattttgga | ccagaattca | tggccaagaa | cttgtatcag | 540 |
| ttgtctccag | tccaagatct | tgaattggcg | aaaatgttgg | tgagggcaaa | cccattgatt | 600 |
| aagaaagata | tggcagagag | aagaagcttc | agtgaggaag | gatacggatc | cgttacacgt | 660 |
| atatttattg | tatgcggaaa | ggatcttgtg | tcacccgaag | attaccagcg | atcgatgatc | 720 |
| agcaactttc | ccccaaaaga | agtaatggag | atcaaagacg | cagatcatat | gccaatgttc | 780 |
| tccaagcctc | aacaactatg | tgctcttctc | ttggagattg | caaataaata | tgcctaa | 837 |

<210> SEQ ID NO 35
<211> LENGTH: 792
<212> TYPE: DNA
<213> ORGANISM: Arabidopsis Thaliana

<400> SEQUENCE: 35

| | | | | | | |
|---|---|---|---|---|---|---|
| atggagaaga | acaacaagaa | gcggtttgtc | ctcgtccatg | ggctgtgcca | cggcgcttgg | 60 |
| tgttggtaca | aggtgaaaac | gcatctggag | gctgtaggtc | actgtgtgac | cgcggtggat | 120 |
| ctagctgcat | ccggtataaa | tatgactaga | ttggaagaga | ttcagacttt | gaaggattac | 180 |
| tgcaaacctt | tgcttgagtt | actgaactca | cttggctcgg | atgacgataa | ggtgattctt | 240 |
| gttgcgcata | gtatgggagg | aatacctgct | gctctcgctt | ctgacatatt | ccctagtaag | 300 |
| attgctacta | ttgttttctt | gacagctttt | atgcccgaca | caagaaacct | acctgcttat | 360 |
| gtttaccaaa | agctaatcag | aagcgttcca | caagaaggat | ggttggacac | cgtgtttgga | 420 |
| acgtatggga | acatgaatg | tcctctagag | tttgctcttt | ttggaccaaa | gttcatggcc | 480 |
| aagaatttgt | atcaactctc | tccggtccaa | gatcttgaat | tggcgaaaat | gttggtgaga | 540 |
| gtaaacccca | tcattacaaa | taatctggca | gggacaagaa | gctttagtga | ggaagggtac | 600 |
| ggtaccgtta | cacgtatata | tattgtatgt | ggagaggaca | tggcggtacc | cgaggattac | 660 |
| cagtggtgga | tgatcaagaa | ctttccgcca | aagaagtaa | tggagatcaa | atgtgcagat | 720 |
| catatggcaa | tgttctccaa | gcctcacaaa | ctatgtgctc | ttctcgtgga | gattgcatgt | 780 |
| aaatatgcct | aa | | | | | 792 |

<210> SEQ ID NO 36
<211> LENGTH: 912
<212> TYPE: DNA
<213> ORGANISM: Arabidopsis Thaliana

<400> SEQUENCE: 36

```
atcacgctat tctcaaacaa gcaaagaacc ttaaccaaaa agaaaacgtc tacggagaca         60
tatggagagg aaacatcact tcgtgttagt tcacaacgct tatcatggag cctggatctg        120
gtacaagctc aagcccctcc ttgaatcagc cggccaccgc gttactgctg tcgaactcgc        180
cgcctccggg atcgacccac gaccaatcca ggccgttgaa accgtcgacg aatactccaa        240
accgttgatc gaaaccctca aatctcttcc agagaacgaa gaggtaattc tggttggatt        300
cagcttcgga ggcatcaaca tcgctctcgc cgccgacata tttccggcga agattaaggt        360
tcttgtgttc ctcaacgcct tcttgcccga cacaacccac gtgccttctc acgttctgga        420
caagtatatg gagatgcctg gaggtttggg agattgtgag ttttcatctc atgaaacaag        480
aaatgggacg atgagtttat tgaagatggg accaaaattc atgaaggcac gtctttacca        540
aaattgtccc atagaggatt acgagctggc aaaaatgttg cataggcaag ggtcattttt        600
cacagaggat ctatcaaaga agaaaagtt tagcgaggaa ggatatggtt cggtgcaacg        660
agtttacgta atgagtagtg aagacaaagc catcccctgc gatttcattc gttggatgat        720
tgataatttc aacgtctcga aagtctacga atcgatggc ggagatcaca tggtgatgct        780
ctccaaaccc caaaaactct tgactctct ctctgctatt gccaccgatt atatgtaata        840
atcttaagtc cgttttactt ttttctcatc gttactaata aaacaaaccc cttttccgg         900 gcaactttca tc                                                             912

<210> SEQ ID NO 37
<211> LENGTH: 819
<212> TYPE: DNA
<213> ORGANISM: Arabidopsis Thaliana

<400> SEQUENCE: 37
atgctgagag taagaaaggc aatggagaat aagaaccaga agcggtttgt gctcatccat         60
ggggtgtgcc acggggcatg gacttgggac aaggtgaaaa cgcagctgga ggttgcaggt        120
cactgtgtga cggcagtgga tcttgctgca tcaggtataa acatgaccaa agtggaagag        180
attcagactc tgaacgatta ctgcaaacca ttgcttgagt ttctgagctc gcttggctca        240
gatgacggta aggtgattgt tgttgctcat agcatgggag gaatatccgc tgcacttgct        300
gctgacagct tcgcttgtaa gattgccgct attgtctttt tgacagcttt catgcccgac        360
acaataaacc cacctgctta tgtttacgaa agctgctca gaagcattcc acaagaggaa        420
tggttggaca ccacgtgtgt gaactacggg aaacctgatt ttcctctaca gtatactctt        480
ttgggaccaa agtttatggc caagaaaatg tatcaaaact ctccagttca agatcttgaa        540
gtggtgaaga cattagtgag ggaaaacccg ttagttacaa acaatctggc agggacaaga        600
agctttagtg aggaaaggta cggatccgtt acacgtatat atattgtatg cagagaggat        660
cttgtggaag tcgaagatta ccagcgttgg atgattagca actttccacc aaaagaagta        720
atggagatca aatgtgcaga tcatatgcca atgttctcca agcctcaaga agtttgtgct        780
cttctcctgg agattgcaaa taaatattgc aaaaattaa                                819

<210> SEQ ID NO 38
<211> LENGTH: 783
<212> TYPE: DNA
<213> ORGANISM: Arabidopsis Thaliana

<400> SEQUENCE: 38
atggataaga ataaccagaa gaagtttgtg cttgtacatg gaatctgcca tggagcttgg         60
tgttggtaca aggtgaaagc ccagctggag gctgctggtc attctgtgac cgcagttgat        120
```

-continued

```
ctagctgcat ctggtgtaaa catgactagc ctggatgaga ttcagacttt gaaggattac      180
tgcaaaccgc tgctcgagtt tctgagctca cttggctcgg atgacgataa ggtgattctt      240
gttgctcata gcatgggagg aatatcagct tcacttgctg ctgatatctt ccctagtaaa      300
gttgctgcta ttgtctttgt ggcagctttt atgcccgaca taagcaaccc gcctgcttac      360
gttttccaaa agctggtcaa agacgttaca caagaggtat ggatggatac tgtgtttggg      420
aaacctgatc gtcctctaga gtttgctctt tttggaccag agttcatggc caagtatttg      480
tataacctat ctccccctcca agattttgaa ttggcgaaaa tgtcggtgag gtaagcccg      540 ttcatgacaa acaacctggc agggacaata agcttcagtg aggacaggta cggatccgtt      600
acacgtatat atatcgtatg cggagaggac gttgcggtac ctgtggatta ccagcgtggg      660
atgatcaatg acttcccggt gaaggaagta ctggagatca aagatgcaga tcatatgcca      720
atgttctcta agcctcaaga actctgtgct cttctcttgg agattgcaga taaatacgcc      780
taa                                                                   783

<210> SEQ ID NO 39
<211> LENGTH: 834
<212> TYPE: DNA
<213> ORGANISM: Arabidopsis Thaliana

<400> SEQUENCE: 39
agaagagtaa gaaaaatgta tgaaaacggg ataagcttta taatctcttt acttatatgt      60
ggatgtgtga agagtgagga gatgatgaag caacatttcg tgctagtaca tggttcgtgc      120
ctcggcgcgt ggtgctggta caaggtgaag ccgctgctcg aggcttcggg ccatcgtgta      180
accgccttag acctagctgc ttgtggtata gacacaaggt cgatcactga catttccaca      240
tgcgaacaat attctgagcc gttgattcag ctaatgactt cattgccgaa tgatgagaag      300
gttgtgctcg tgggtcatag ctatggaggt ttgactttag ccatagccat ggataagttt      360
cccgacaaaa tctctgtctc tgtcttcgta acttctttca tgcccgacac caaaaactca      420
ccatcgttcg tcctggaaaa gtttgcaagc accatgacac cagaagattg gatgggctct      480
gagctcgagc cgtatgtggt cttcagcgct gagttcacga agcaccgtat cctccaactt      540
tctcctattg aagatcttga gcttagattg cttctaaaga ggcctggttc attatttctt      600
aatgatttat cgaggatgaa gaacttttct gaaaagggt atggatctgt tcctcgagct      660
tacattgtga gcaaagatga ccacaccatc tcggaagaat atcaacgatg gatgatcgat      720
aactatccgc cgaatttagt gatagagatg gaagggacgg atcatttgcc attgttttgc      780
aaacctcaac tactaagtga ccatctattg gcaatcgccg acaaattctc ttaa           834

<210> SEQ ID NO 40
<211> LENGTH: 771
<212> TYPE: DNA
<213> ORGANISM: Arabidopsis Thaliana

<400> SEQUENCE: 40
atgaagcatt atgtgctagt tcacggaggc tgccacggtg cgtggtgttg gtacaaggtg      60
aagccgatgc ttgaacattc cggccaccgt gtcacggttt tgatcttac ggcgcatggt      120 gtgaacatga gcagagtaga agatattcag actttggagg atttcgctaa gccgttgctt      180
gaggttcttg agtcttttgg ctcggatgat aaagtagtcc tcgtcgcgca tagcctcggt      240
ggaataccgg ctgctcttgc agccgacatg tttcctagta aaatctctgt tgctgtcttc      300
```

| | |
|---|---:|
| gttacttctt ttatgcccga cacaacgaat ccaccttctt acgtgttcga aagtttctc | 360 |
| ggaagcatta cagaagaaga acgtatggac ttcgagttag ggagctatgg aacagatgac | 420 |
| catccactaa agactgcttt tcttggacct aactacttga agaatatgta tctactttct | 480 |
| cctatcgaag attatgaatt ggccaaaatg ttgatgagag tcacaccggc tattactagt | 540 |
| aatctgacgg ggactaaaag cttaacggca caaggatatg gatcgattag tcgtgtgtat | 600 |
| atcgtatgcg gagaagataa gggtatacgt gtagatttcc aacgatggat gattgagaac | 660 |
| tctccggtta aagaagtgat ggagatcaaa gatgcagatc atatgcctat gttttccaag | 720 |
| cctcatgaac tctgtgatcg tcttctaaag attgctgata aatatcccta a | 771 |

<210> SEQ ID NO 41
<211> LENGTH: 901
<212> TYPE: DNA
<213> ORGANISM: Arabidopsis Thaliana

<400> SEQUENCE: 41

| | |
|---|---:|
| accaaaagca ataccaaatg caaacacacc acatgcagca acaacaactc catcacttcg | 60 |
| tctttgtcca cggctcatgt catggagcat ggtgctggtt caaactagct gcaaagctca | 120 |
| agctcgatgg tcaccgtgtg acagctatcg accttggtgg ctccggtgtc gacacgaggc | 180 |
| agctccatga ggttcgtttg tgtcggcgt atctagagcc tttgatgagt ttcatggagt | 240 |
| ctctccctga aaacgagaaa gtggttcttg ttggtcatag ctatggtggc attggaactt | 300 |
| ctcttgctat ggaaaggttt ccgaccaaag tctctgtcgg aatcttcctc tctgcttaca | 360 |
| tgccgcacca tgactctcct ccggcggttt tgattcaaga gtattttacg agactaccag | 420 |
| agggtttcgc tatggactgt gagtttacat tcgaggaagg attagaacac ccaccaagtt | 480 |
| cagttttgtt cggtactagt ttcttgaagg agaaggcata tagtaattgc cagttagagg | 540 |
| atctagaatt agccatggcg ttgatgaaac caagctggtt atacactaag gaaatgggag | 600 |
| gtgaagatct gataacaaag gagaggtatg gatctgggaa gagagtgttt attgtctgtg | 660 |
| aaggcgacaa tgtggttcca gaggagattc agaagtggat gattagtaac tacgagcctc | 720 |
| acgaagttaa gcggattgaa gaagctggtc acatggctat gctcactaag cctcatgaac | 780 |
| tttctcaact gctacaagaa atagcagcga aatataacta aatgtaaaat gatgacacct | 840 |
| gtgtatgatt tgggctcagt tacatctatg atatgaataa gagagtttca atatttgtga | 900 |
| t | 901 |

<210> SEQ ID NO 42
<211> LENGTH: 1173
<212> TYPE: DNA
<213> ORGANISM: Arabidopsis Thaliana

<400> SEQUENCE: 42

| | |
|---|---:|
| atgggaaacc tctgttcttt gtttactccg ccaaaacccg tgaagaaaag aaaacccatc | 60 |
| acaaaaagac aatcttctat cggagcttct tcttccgggt cgggtcttaa tagtaaccgt | 120 |
| tggaacaacg gggtcagatc atcttcttct agaagagaca acaagttcga agatgctttg | 180 |
| attcaagaac atgctcttgc tgctgctgct gttttgttcc gacagcaaaa cggtggtgga | 240 |
| ggatcgttgc cgtttgatcg gtcggcttca caacgttatc aaggttcttg ttcgaagaag | 300 |
| aaccagttgc ctcgaagctc gagttcgagg tcaaggtctt ctacagatcc tctgttacaa | 360 |
| cctcatcagt ttcttaatca gggtataaag ctagatgact tggaaacaaa ccattttgtc | 420 |
| cttgttcatg gaggtagttt tggcgcttgg tgttggtata aaccattgc acttcttgag | 480 |

```
gaagatggtt ttaaagttac cgctatagac ttagcaggtt gcggtattaa ctcgattaat      540
ataaatggca tcgctagttt gtcacaatat gtcaagccac ttaccgatat tcttgaaaag      600
cttcccatag gagagaaggt gatattggtc ggtcacgatt ttggtggagc atgtatatct      660
tatgctatgg aactctttcc ttcaaagatt tcgaaagcgg ttttcctcgc tgcagcgatg      720
ttaacaaatg gtcaaagtac actcgatatg ttctccttga aggccggtca gaacgattta      780
atgagaaaag ctcagatatt tatctacaca aatggtaatg aaaaccctcc aaccgcaatt      840
gacttagaca atctcttct caaagacctt tgttcaacc aaagcccttc gaaggacgtt       900
gcattggctt ctgtatcaat gaggtcaatt ccatttgcgc cggttcttga aaaactctct      960
ctttcggatg ctaactacgg atcagttaga cggtactata tagagacgtt agaagacaat      020
gctataccag tgactcttca agaaaacatg atcaatagta gtcctcctga aaaggtttat     080
cggttaaaag gcgccgacca tgctcctttc ttttccaaac cacaagcttt gcataaactt     140
ctgcttgaga tcgccagaat tagccctgct taa                                  173

<210> SEQ ID NO 43
<211> LENGTH: 771
<212> TYPE: DNA
<213> ORGANISM: Arabidopsis Thaliana

<400> SEQUENCE: 43
atgctagtta agaaattcgt tttggtgcat ggtgaagggt ttggggcatg gtgttggtac       60
aaaactattg cgtcattgga ggagtctgga ctgtctcctg ttacggttga cctcgctgga      120
tctggattta atatgacaga cgcaaatagt gtttccacct tagaagaata ttcaaaaccg      180
ttgatcgagc tcattcaaaa tcttcctgct gaagaaaagg tgattctggt aggtcacagt      240
actggagggg catgtgtttc atatgcgtta gagcggtttc cagagaaaat ctcaaaagct      300
atattcattt gtgcaactat ggttactgat ggacaaagac ccttcgatgt cttcgctgat      360
gagcttggtt ctgcagaacg gttcatgaaa gagtcacagt tcttgatcta tggaaacggc      420
aaggacaacc ccgcgacagg gttcatgttc gagaaacaac acatgaaagg cttgtacttc      480
aatcagtcac caaataagga cattgcattg tcaatgatct cgatgcggcc tgtaccatta      540
ggtcccatga tggagaagtt gtcacttagt gcagaaagat atgggaaagg tcggagattc      600
tatgtccaga cgctcgatga cttggctctt tcaccggacg ttcaagagaa actggttcga      660
gagaatagtc ccgaagcagt ttttaagatc aaaggaagtg atcattgccc attcttctct      720
aaacctcagt ctcttcacaa gatccttctt gaaatagcac agattcctta a               771

<210> SEQ ID NO 44
<211> LENGTH: 1665
<212> TYPE: DNA
<213> ORGANISM: Arabidopsis Thaliana

<400> SEQUENCE: 44
atggggaact cgttcacatg catatctcac gagcaggaac aacgtcccaa gaaatcttcc       60
ggcggaggag gaaataactc cgggaaatac aaatacgtgc gtcgtctgtc gctgatgcct      120
tcatttagaa ggaggacgct acttcctccg ctctcctgct ctggatcatc atccacttcg      180
tcttccaaga aaggcgggat caaagcaaag acgaagaaga taagagagag acatcatcat      240
catcatcaag accacgaaaa agactctcat ataattcaag agcagacact agcagccact      300
aatctcctct tcaaccaaac ccctcgtaac agcaactctg ttgttcctcc tagtttcaga      360
```

-continued

```
cgctccacct ctgttgtata tccctctgct cagccatcgg gtaccagctc aggacccgtt    420
tcagccgtcc agactcctaa gaagtcaagc gcgggattcg taagaagctc tagctctagg    480
caaaggtcca gtaccgatcc catgatcaag cctaaccagc tcgagctaaa taaggtggaa    540
ggttcggaga cgaagcggtt tgtgctggtt catggtggtg ggttcggagc ttggtgttgg    600
tacaaaacca taactctttt agagaagcat ggtttccaag tcgatgctgt tgagttgacc    660
ggttcaggtg tgagctcgat tgacacaaac aacatcacca gcctcgctca ctactccaag    720
cctctcctcc atttcttcga atccctcaaa cccaccgaga aggtgatact ggtgggacat    780
gattttggag gagcttgtat gtcctatgcg atggagatgt tcctacaaa gatcgccaaa    840 gctgtcttta tctctgctgc tatgttggct aatggccaaa gcactcttga tctctttaat    900
caacagctgg ggtcaaatga tctgatgcaa caagcacaga tatttctgta cgccaacggc    960
aaaaagaatc ctccaactgc cgttgatttt gacagatctt tgcttagaga ctttctcttt   1020
aatcaaagcc ctcaaaagga cctcgcattg gcatcggtat ccattagacc gatcccattc   1080
gcaccggtca gcgaaaaggt tcacgtgtcg gagaaaaact acggttctat ccgacggttc   1140
tacatcaaaa ccatggaaga ttacgctgta ccggttcttc tccaggaagc aatgatcaaa   1200
ttgaacccac cggaacaagt ttttcagctc aaaggctccg atcacgcacc gttcttctct   1260
cggcctcagt ccttgaacaa aatcctcgtc gagatatctc aaataccagg aacaggaaat   1320
cgaatgggtc gtggagtgag cgtaggtggt gggcaaagtt ctttagggta tctttttggt   1380
agcggagaag ctccaaagcc agccattaac aatgctcctg caccatcatc tgaaactctg   1440
cctataagtg ctgatccttc accaaaacat gttgctgctc agacggttaa tgttaccaag   1500
caaatacctg ctggtatcaa taatcctct acaaacaact acattcgagc agatggacag   1560
aacacaggca acttccttac ggaccggcca tcgaccaagg ttcatgcagc ccctggaggc   1620
ggctcatctc tggattacct cttcggtggt ggcggaagca actag                    1665
```

<210> SEQ ID NO 45
<211> LENGTH: 1272
<212> TYPE: DNA
<213> ORGANISM: Arabidopsis Thaliana

<400> SEQUENCE: 45

```
aaacaagcct atatgctgct gatcccatct aggggccaag cctctcttct ttaaaaactt     60
ttgacttcca ttttcttgag aattcccctt tctgggttct tgatttgaa agatgggtaa    120 caagataatc tcaatgatga agaaagatag caaagatgga ggaggaggag gatctaagag    180
caagagaatg aatcggtctc agaggaaatt acttgctgat gaagagatgt tgcatcgtcg    240 agctcttttcc atggcgattc atcaagctca gctttctcag agatttgatg gatctatgtc    300
tagacgggtc ggtctacta gtactaggaa acgtactctc tctgacccgt tttctaatgg    360
caagcaggta cctgattttt cagagagctt gatagtgaag aaatttgttc tggtgcacgg    420
tgaaggattt gggcatggt gttggtacaa aatggttgct tcattggaag agtcaggact    480
gtctcctgtt acagttgacc tcactgggtg tggatttaat atgactgaca caaatactgt    540
ctctaccttg gaggaatatt caaaaccgtt gatcgatctc ctcgaaaatc tccccgaaga    600
agagaaggtt attctagtgg gtcacagtac tggaggtgct tccatttcat atgcgttaga    660
gaggtttcca gagaaaatct ctaaagctat attcgtatgt gcaacaatgg tttctgatgg    720
ccaaagacct tttgatgttt tctctgaaga gcttggttcc gcagagcggt tcatgaagaa    780
gtcgcagttc ttgatttatg ggaacggtaa agacaagcct cctacggggt tcatgtttga    840
```

```
gaagccacat atgaaaggct tgtatttcaa tcaatcaccc aacaaggata tagcattggc      900
gatgatctca atgagacctg taccactcgg accaatgatg agaaagtat  ctctaaccgc      960 agaaagatat gggaagggaa gaagattcta cgtccagacg ctagatgacc gtgcactttc     1020
accagatgtt caagagaagt tagtgagaga aacagccct  gaaggagtct tcaagatcaa     1080
aggaagtgat cattgccctt tcttctcaaa gcctcaatct ctccacaaaa tccttctgga     1140
gattgcacag attccttaac aaagctctga gattattata cttttgaaaa cgagaataca     1200
ctttccattt aatcctcaaa acatcttttg tatgcaattc tagaatcaat gatacaagat     1260
cgtatttata cc                                                         1272
```

```
<210> SEQ ID NO 46
<211> LENGTH: 1371
<212> TYPE: DNA
<213> ORGANISM: Arabidopsis Thaliana

<400> SEQUENCE: 46 atgggaaaact ctttaagatg catatcacaa gaacaagatc caaaccagaa gaaacctagc      60
tccgtcgtca acggtaatag ctccgagaaa cacgttcgga ggctgtcttt gataccatct     120
ttccgacgcc ggacattact accatctctc tcttgctccg gatcctcaac ttcgtctacg     180
tccaagaaag gagggatcaa gacaaaaaag aagataagag aaagacacca ccaagagcaa     240
catcatcatg atcatgagaa agactctctt attcaagacc aaacattagc tgccactaat     300
attctcttta gtcaaacgcc tcgtaacagc aactctgctc ctccttccg  acgctccacc     360 tccgtcgttt acactcagcc acctaccgcc gctgtagccg cctccgtagg ttctgtttcc     420
ggcgccttga ctcctaagaa atccactta  ggatacgtta aagttctag  caataggcag     480 agatcaagca ctgatcctgt tcttaaaccc aatcagcttc tagacaaggc aagcaaattt     540
aatttgccta tctcccacaa taatgagcta aaggtcgaag gtgcggagac aaagcggttc     600
gtgctggttc atggaggagg gttttggtgca tggtgttggt acaaaaccat aacgctctta     660
gagaaacatg gtttccaagt agacgccgtt gacttgaccg gttccggtgt cagctctttt     720
gacacaaaca acatcactag cctcgctcaa tacgtcaaac cactcctcca tttctttgac     780 acccttaaaac ccaccgagaa ggtgatatta gtggggcatg attttggagg agcttgtatg     840
tcttatgcca tggagatgta cccttctaag atcgctaagg ctattttcat atctgctgct     900
atgttggcta atgcccaaag cactctcgat ctctttaacc aacagcctga ctcaaattat     960
gatctgatgg aacaagtcca tctatttctg tacgccaacg gcaaaagaa  ccctccaaca    1020 gccgttgatt tcgacagatc attgcttaga gatttttttct ttaatcagag ccctccaaag    1080
gacgttgcat tagcgtcggt atcgatgaga ccaatcccgt tcgcaccagt ggtcgaaaag    1140
ctccacgtgt cggagaaaaa ttacggttca atccgacggt tctacatcaa aaccatggag    1200
gatgattacg ctgtaccggt ttctctccaa gatgcaatga tcaaatcaaa ccctccagaa    1260 caagttttc atctcaaagg ctctgaccat gcacctttct tctctcgtcc tcagtctttg    1320
aaccggatac tcgttgagat ttctcaatta cctcccaaga aatcttcttg a             1371
```

```
<210> SEQ ID NO 47
<211> LENGTH: 934
<212> TYPE: DNA
<213> ORGANISM: Arabidopsis Thaliana

<400> SEQUENCE: 47
```

```
gttaaaaggt gagatagtgt aaaagcattg atcaagattc atgcaatggg aggagaaggt      60
ggtgctgagc ccgtaattca ctttgtgttt gttcatggag ccagtcacgg agcttggtgt     120
tggtataaac tcaccactct tctcgacgcc gccgggttca aatcaacctc cgtagatctc     180
accggcgctg gcatcagcct catagactct aacatcgtct tcgactccga ccaatataac     240
cgtcctctct tctctctctt gtccgatctc cctcctcacc acaaagtcat actcgttgga     300
catagcatcg gtggaggaag tgtcaccgaa gctctttgca agttcactga caaaatctcc     360
atggccattt acctcgcggc ttccatggtt caacccggat ccatcccttc tccgcatctt     420
tcaaacatac atgtgggaga agaagatata tgggagtaca catatggtga aggtaccgat     480
aaaccaccca ccggagtcct catgaaaccg agtttatac  gccattatta ctatagccaa     540
agccctcttg aggacgtaac tttgtcatct aagctgttgc gtcctgctcc tatgagggcc     600
tttcaagatc ttgataagct acctccaaat cccgaggccg agaaagttcc tcgagtttac     660
atcaagactg ctaaggataa tctatttgat tctgtgcgtc aagacctttt ggtggagaat     720
tggccaccct ctcagctgta tgtcttggag gatagtgacc attctgcttt cttctctgtc     780
ccaactacct tattcgcgta tctcctccgt gcggtttctt ttcttcaacg ataaacttca     840
acttatcctt catacattcc gatctagata acaaactaat gggaataat  tagatgattt     900 gtttggaagg tgattgatat gatattatga ttct                                 934

<210> SEQ ID NO 48
<211> LENGTH: 831
<212> TYPE: DNA
<213> ORGANISM: Arabidopsis Thaliana

<400> SEQUENCE: 48
atggcggagg agaatcaaga agaaaccta  gaactcaaac caagtagaaa accaccacac      60
tttgtgctaa tacatggcat gagcttagga tcatggtgct ggtacaagat caaatgtctc     120
atggaagtct ctggcttcac cgtcacttgc atcgacctca atcctccgg  catcgattct     180 tcatccgtgg attcactcac taccttcgac caatacaacc aaccactcat cgacttcctc     240
tcctctttcc ccgaacaaga acaggtgata cttgtgggtc acagtgcagg agggcttagc     300
ctaacgagtg cgatacagag attccctaag aagatctgtc tcgctgtttt tattggagct     360
tcgatgctca aaaacgggct tcagacagat gaagatatga aagatggagt gcctgatcta     420
tcagaacatg gtgatgtcta cgagcttggt tttggtctag accgggagaa tcctcccacc     480
agtgctatta tcaaacctga ataccgacga aaactacttt accacatgag tcctcaacag     540
gaatgttcct tggctgcatt aatgatgaga ccagcaccaa ttttggcgtt aacgacagca     600
aaactggaag aagaggaaaa agaaaaagga caagaggagc aagtgccgcg cgtgtacatc     660
aagacgttac tcgaccgggt catgaaaccg gagcagcaag acgcgatgat aagacggtgg     720
ccacctagcc aagtttacga attggagagc gaccattctc ctttcttctc taacccttt    t  780 gttctctttg gtttactcat caaagctgcc gtttccgtcg gttctatcta a              831

<210> SEQ ID NO 49
<211> LENGTH: 910
<212> TYPE: DNA
<213> ORGANISM: Arabidopsis Thaliana

<400> SEQUENCE: 49
attacagcca tacagaaata tcacactaac tacaaaagat agtgcaagga atgtgatgta      60
cgagaagagg attaaagatg agtgagcatc attttgtgtt tgtgcatggt gcagggcatg     120
```

| | |
|---|---|
| gaggatggtg ttggtacaag ctggctaatt cactgaggga taatggacat aaggctacat | 180 |
| gtatagacct caagggtgct ggtatcaacc caactgatcc aaacactgtc tcttctttgg | 240 |
| atgactacga cgagcctctc tatgccttcc tctcccaact tcccaacgat caaaaggtca | 300 |
| ttcttgtgag ccacagcgtt ggaggaggga gcatgacggc tgccatgtgc ctctttcctt | 360 |
| ccaaagtttc cttggcggtt tacgtcgcag cagccatggt caaacctggt accttgattc | 420 |
| ctgaaagact caaaaatgta atgaagatat gttcaggatt gatagaggag gaaactgaga | 480 |
| agatatggga ctttactttc ggaaatggac cacaaaatct cccaacaagc atcatgatga | 540 |
| aacctgagta tgttcgggac aagttttaca acgagagccc catggaggat tacacactgg | 600 |
| caaccacact tctgcgtccg gcccctgtca tggcattcat aggcataatg gatattccgg | 660 |
| gagctccaga gactgacaaa atcccaagag tgtacgtgaa acaggcaag gaccatttgt | 720 |
| tcgaaccagt tcttcaagag gtaatgttgg ccctgtggcc tcctgctcac accttccttc | 780 |
| ttccggacag tgaccactct gctttttct cccaacctca agaactctat caattcctcc | 840 |
| ttcaagcagc ctcatctctt tctccctgat atttatgtct ctctggaact cttttaaatc | 900 |
| catcttttgg | 910 |

<210> SEQ ID NO 50
<211> LENGTH: 4
<212> TYPE: PRT
<213> ORGANISM: Nicotiana tabacum

<400> SEQUENCE: 50

Asn Ser Ser Phe
 1

<210> SEQ ID NO 51
<211> LENGTH: 31
<212> TYPE: DNA
<213> ORGANISM: Artificial Sequence
<220> FEATURE:
<223> OTHER INFORMATION: primer

<400> SEQUENCE: 51

| cgcggatcca tgaaggaagg aaaacacttt g | 31 |
|---|---|

<210> SEQ ID NO 52
<211> LENGTH: 30
<212> TYPE: DNA
<213> ORGANISM: Artificial Sequence
<220> FEATURE:
<223> OTHER INFORMATION: primer

<400> SEQUENCE: 52

| gcgggatcca gatcagttgt atttatgggc | 30 |
|---|---|

<210> SEQ ID NO 53
<211> LENGTH: 30
<212> TYPE: DNA
<213> ORGANISM: Artificial Sequence
<220> FEATURE:
<223> OTHER INFORMATION: primer

<400> SEQUENCE: 53

| ccgctcgaga tgaaggaagg aaaacacttg | 30 |
|---|---|

<210> SEQ ID NO 54
<211> LENGTH: 29

```
<210> SEQ ID NO 54
<211> LENGTH: 29
<212> TYPE: DNA
<213> ORGANISM: Artificial Sequence
<220> FEATURE:
<223> OTHER INFORMATION: primer

<400> SEQUENCE: 54
ggggtaccag atcagttgta tttatgggc                                          29

<210> SEQ ID NO 55
<211> LENGTH: 32
<212> TYPE: DNA
<213> ORGANISM: Artificial Sequence
<220> FEATURE:
<223> OTHER INFORMATION: primer

<400> SEQUENCE: 55
gcgggatccc tgagtatcca accaattctc gg                                      32

<210> SEQ ID NO 56
<211> LENGTH: 18
<212> TYPE: DNA
<213> ORGANISM: Artificial Sequence
<220> FEATURE:
<223> OTHER INFORMATION: primer

<400> SEQUENCE: 56
tggcccaaag ttcttggc                                                      18

<210> SEQ ID NO 57
<211> LENGTH: 25
<212> TYPE: DNA
<213> ORGANISM: Artificial Sequence
<220> FEATURE:
<223> OTHER INFORMATION: primer

<400> SEQUENCE: 57
tcacatcaac attgtggtca ttggc                                              25

<210> SEQ ID NO 58
<211> LENGTH: 23
<212> TYPE: DNA
<213> ORGANISM: Artificial Sequence
<220> FEATURE:
<223> OTHER INFORMATION: primer

<400> SEQUENCE: 58
ttgatctggt caagagcctc aag                                                23
```